US012240834B2

United States Patent
Bird et al.

(10) Patent No.: US 12,240,834 B2
(45) Date of Patent: Mar. 4, 2025

(54) POLYMORPHS OF [2-(1H-INDOL-3-YL)-1H-IMIDAZOL-4-YL] (3,4,5-TRIMETHOXYPHENYL)METHANONE AND ITS SALTS

(71) Applicant: VERU INC., Miami, FL (US)

(72) Inventors: Thomas Gary Bird, Eads, TN (US); Kester Gary Barnette, Denver, NC (US); Mitchell S. Steiner, Germantown, TN (US)

(73) Assignee: VERU INC., Miami, FL (US)

( * ) Notice: Subject to any disclaimer, the term of this patent is extended or adjusted under 35 U.S.C. 154(b) by 0 days.

(21) Appl. No.: 18/140,576

(22) Filed: Apr. 27, 2023

(65) Prior Publication Data

US 2023/0348433 A1    Nov. 2, 2023

Related U.S. Application Data

(60) Provisional application No. 63/336,198, filed on Apr. 28, 2022, provisional application No. 63/336,193, filed on Apr. 28, 2022.

(51) Int. Cl.
*C07D 403/04* (2006.01)

(52) U.S. Cl.
CPC ........ *C07D 403/04* (2013.01); *C07B 2200/13* (2013.01)

(58) Field of Classification Search
CPC ........................... C07D 403/04; C07B 2200/13
See application file for complete search history.

(56) References Cited

U.S. PATENT DOCUMENTS

2019/0374512 A1*  12/2019  Li .......................... A61P 35/00

FOREIGN PATENT DOCUMENTS

WO    WO-2022067185 A1 *  3/2022

OTHER PUBLICATIONS

Deng S., et al., "An orally available tubulin inhibitor, VERU-111, suppresses triple-negative breast cancer tumor growth and metastasis and bypasses taxane resistance", Mol. Cancer Ther. 2020, 19(2): pp. 348-363.
Grodowska K. et al., "Organic Solvents in the Pharmaceutical Industry", Acta Poloniae Pharmaceutica-Drug Research 2010, vol. 67, No. 1, pp. 3-12.
Wang Q. et al., "Structural Modification of the 3,4,5-Trimethoxyphenyl Moiety in the Tubulin Inhibitor VERU-111 Leads to Improved Antiproliferative Activities", J. Med. Chem. 2018, 13; 61(17): pp. 7877-7891.
International Search Report dated Sep. 28, 2023 in respect of International Application No. PCT/US23/20284.

* cited by examiner

*Primary Examiner* — Clinton A Brooks
*Assistant Examiner* — Izabela Schmidt
(74) *Attorney, Agent, or Firm* — Mark S. Cohen; PEARL COHEN ZEDEK LATZER BARATZ LLP

(57) ABSTRACT

The invention encompasses polymorphs of [2-(1H-indol-3-yl)-1H-imidazol-4-yl](3,4,5-trimethoxyphenyl)methanone and salts thereof. These polymorphs are characterized by their x-ray diffraction pattern and DSC thermograms, among other methods. The polymorphs are used in the preparation of pharmaceutical compositions and products.

12 Claims, 48 Drawing Sheets

POLYMORPHS OF [2-(1H-INDOL-3-YL)-1H-IMIDAZOL-4-YL] (3,4,5-TRIMETHOXYPHENYL)METHANONE AND ITS SALTS

CROSS REFERENCE TO RELATED APPLICATIONS

This application claims the benefit of priority of U.S. Provisional Application No. 63/336,193, filed on Apr. 28, 2022 and 63/336,198, filed on Apr. 28, 2022, hereby incorporated by reference.

BACKGROUND OF THE INVENTION

Discovery of novel polymorphs can help lessen the limitations in preclinical or clinical research, and pharmaceutical manufacturing processes due to poor or limited solubility drugs, which is often a challenge in drug development. The polymorph can provide a stable, easily manipulated form of the drug that can ease processing and administration. Finding an adequate polymorph, however, can be a time consuming and difficult task, when considering the wide variety of novel polymorphic forms that a compound or its pharmaceutically acceptable salts or solvates may exhibit. The availability of multiple polymorphs to select from allows the physicochemical properties of a compound to be modulated by the choice of a polymorph that facilitates the manufacture of a commercial drug product from the compound. Improvements in physicochemical properties can be achieved by altering the physical forms of a given compound. Common physical forms include amorphous (non-crystalline forms that lack long range order) or crystalline (ordered arrangements of molecules in a packing array) polymorphs. Without loss of pharmaceutical activity, it is possible to screen for polymorphs of the unmodified compound or solvates, salts, hydrates, etc., thereof. The latter three physical forms differ in chemical composition and so technically these are pseudopolymorphs. Once polymorphism or pseudopolymorphism is established, the alternate forms may also be characterized in order to reveal those with favorable properties. Properties that vary across different polymorphic forms include thermodynamic properties such as melting and sublimation temperatures and vapor pressures, enthalpy, entropy, heat capacity, free energy, chemical potential, and solubility; kinetic properties such as dissolution rates, rates of solid state reaction, physical/chemical stability, rates of nucleation/crystal growth; packing properties such as molar volume and density, conductivity (electrical or thermal), refractive index, particle morphology, hygroscopicity or color; surface properties such as surface free energy or interfacial tensions; or mechanical properties such as hardness, tensile strength, compactibility and tableting, handling, filtration, flow and blending.

The most important properties during drug discovery and development include solubility, dissolution rates, bioavailability, and physical/chemical stability. Other favorable differences in physicochemical properties may include higher melting point, more favorable powder characteristics, etc. that result from employing the optimal polymorph in formulations with greater stability to storage, e.g., at higher temperatures and/or higher relative humidity, or easier or cheaper manufacturing and/or distribution procedures. In many known cases, several polymorphs exist and can crystallize concomitantly. However, the system tends to move toward the thermodynamically equilibrated state. In other words, the metastable forms in any system eventually transform to the most stable form. Accordingly, the solid dosage form should employ the most stable form to avoid changes in their physicochemical properties. However, the routes to the final state depend on kinetics as well as other factors requiring extensive testing of all metastable forms discovered and their specific conditions that cause the process of interconversion to other, more thermodynamically stable forms.

In some cases, certain stable crystalline polymorphs are discovered initially because the energetic barriers to nucleation of these less stable polymorphs are relatively low compared to the most stable form. However, much later these polymorphs may be discovered to convert to the thermodynamically most stable polymorph. Though the conversion of less stable forms to the most stable at ambient conditions may be too slow of a process to employ commercially, the process to obtain the pure thermodynamically most stable polymorph can be accelerated by addition of a small amount of the most stable polymorph during the crystallization process. This type of process, known as crystal seeding or seeding, removes the relatively high energetic barrier to nucleation of most stable polymorph, resulting in a process to directly and rapidly make pure preparations of the most thermodynamically stable polymorph.

Polymorphs are discovered by recrystallization out of a single solvent or mixtures of solvents, heating to induce transitions (e.g., a monotropic polymorph does not change to another form over the entire temperature range), slurry experiments, and other methods known to the skilled artisan. The most thermodynamically stable polymorph form is required for formulations of the active pharmaceutical ingredient (API) as the less stable forms are susceptible to transforming to thermodynamically stable form, e.g. during compression or storage, causing intolerable variations over time in properties of the drug product which can result in withdrawal of the drug product by the FDA.

Tubulin inhibitors exhibit high potency and have been approved by the FDA for the treatment of various cancers. New tubulin inhibitors that bind to the colchicine binding site have shown great potential as therapeutic agents. However, none of these colchicine binding site inhibitors have been approved for oncology or virology indications, whereas colchicine has been approved for anti-inflammatory uses such as gout and familial Mediterranean fever (FMF). [2-(1H-Indol-3-yl)-1H-imidazol-4-yl](3,4,5-trimethoxyphenyl)methanone is one such tubulin inhibitor compound with applications for treating cancer (WO2012/027481), viral infections such as severe acute respiratory syndrome coronavirus 2 (SARS-CoV-2) (WO2021/203100) and influenza (PCT/US23/17943), and anti-inflammatory diseases (WO2022/216308) such as acute respiratory distress syndrome (ARDS). The compound and its activities were disclosed in PCT publications WO2010/74776; WO2011/109059; WO2012/027481; WO2021/203100, and WO2022/216308, hereby incorporated by reference.

Creating a stable polymorphic form of [2-(1H-indol-3-yl)-1H-imidazol-4-yl](3,4,5-trimethoxyphenyl)methanone or its pharmaceutically acceptable salts or solvates would be advantageous at least for synthesizing, handling, and making formulations of the compound.

SUMMARY OF THE INVENTION

One embodiment of the invention encompasses a crystalline polymorph Form A of the [2-(1H-indol-3-yl)-1H-imidazol-4-yl](3,4,5-trimethoxyphenyl)methanone hydrochloride salt characterized by an XRD pattern substantially as depicted in FIG. 35. In one aspect of this embodiment, Form A is characterized by an XRD pattern having peaks at about 9.6, 12.0, 19.2, 23.6, and 24.4 2θ±0.2 2θ. In another aspect of this embodiment, Form A is characterized by an XRD pattern having peaks at about 16.3, 18.1, and 28.9 2θ±0.2 2θ.

One embodiment of the invention encompasses a crystalline polymorphic form of the [2-(1H-indol-3-yl)-1H-imidazol-4-yl](3,4,5-trimethoxyphenyl)methanone hydrochloride salt known as Form B characterized (in Example 3) by an XRD pattern having peaks at 9.5, 12.1, 18.0, 18.9, and 23.0 2θ±0.2 2θ. The crystalline polymorph Form B of [2-(1H-indol-3-yl)-1H-imidazol-4-yl](3,4,5-trimethoxyphenyl)methanone hydrochloride may be further characterized by an XRD pattern substantially as depicted in FIG. 18. Alternatively, the crystalline polymorph Form B of [2-(1H-indol-3-yl)-1H-imidazol-4-yl](3,4,5-trimethoxyphenyl)methanone may be further characterized by XRD peaks at 19.2, 28.5, 29.5, and 31.8 2θ±0.2 2θ. The crystalline polymorph Form B of the [2-(1H-indol-3-yl)-1H-imidazol-4-yl](3,4,5-trimethoxyphenyl)methanone hydrochloride salt is prepared as in Example 3.

Another embodiment of the invention is directed to crystalline polymorph Form $C_H$ of the [2-(1H-indol-3-yl)-1H-imidazol-4-yl](3,4,5-trimethoxyphenyl)methanone hydrochloride salt characterized by an XRD pattern substantially as depicted in FIG. 22. In one aspect of this embodiment, Form $C_H$ is characterized by an XRD pattern having peaks at about 5.1, 13.1, 16.6, 22.5, and 25.7 2θ±0.2 2θ. In another aspect of this embodiment, Form $C_H$ is characterized by an XRD pattern having peaks at about 10.3, 18.0, 23.7, 28.7, and 29.7 2θ±0.2 2θ.

Another embodiment of the invention is directed to crystalline polymorph Form D of the [2-(1H-indol-3-yl)-1H-imidazol-4-yl](3,4,5-trimethoxyphenyl)methanone hydrochloride salt characterized by an XRD pattern substantially as depicted in FIG. 25. In one aspect of this embodiment, Form D is characterized by an XRD pattern having peaks at about 9.4, 15.1, 17.3, 22.1, and 23.2 2θ±0.2 2θ. In another aspect of this embodiment, Form D is characterized by an XRD pattern having peaks at about 10.5, 18.1, 22.8, 24.8, and 30.3 2θ±0.2 2θ.

Another embodiment of the invention encompasses a crystalline polymorphic form of the [2-(1H-indol-3-yl)-1H-imidazol-4-yl](3,4,5-trimethoxyphenyl)methanone hydrochloride salt known as Form E characterized by an X-ray powder diffraction (XRD) pattern having peaks at 9.4, 17.3, 22.1, 23.4, and 24.8 2θ±0.2 2θ. The crystalline polymorph Form E of the [2-(1H-indol-3-yl)-1H-imidazol-4-yl](3,4,5-trimethoxyphenyl)methanone hydrochloride salt may be further characterized by an XRD pattern substantially as depicted in FIG. 29. Alternatively, the crystalline polymorph Form E of the [2-(1H-indol-3-yl)-1H-imidazol-4-yl](3,4,5-trimethoxyphenyl)methanone hydrochloride salt may be further characterized by XRD peaks at 12.9, 15.0, 18.1, 21.0, and 30.3 2θ±0.2 2θ. The crystalline polymorph Form E of the [2-(1H-indol-3-yl)-1H-imidazol-4-yl](3,4,5-trimethoxyphenyl)methanone hydrochloride salt was formed by the processes as described in Examples 4 and 5. One embodiment is directed to a process to make Form E. In one aspect of this embodiment, Form E was made by recrystallization from 2-propanol, 1-propanol/1-dioxane mixture, or ethanol. In one aspect of this embodiment, Form E was made by recrystallization of the [2-(1H-indol-3-yl)-1H-imidazol-4-yl](3,4,5-trimethoxyphenyl)methanone hydrochloride salt that was added to 2-propanol at saturating concentrations at 25° C., heated to 45-50° C. to dissolve solids, and fast evaporated under 1.5 psi of $N_2$ flow at ambient temperature to produce solid Form E. In another aspect of this embodiment, Form E was made by recrystallization of the [2-(1H-indol-3-yl)-1H-imidazol-4-yl](3,4,5-trimethoxyphenyl)methanone hydrochloride salt that was added to 1-propanol/1-dioxane mixture at saturating concentrations at 25° C., and solvent was slowly evaporated at ambient temperature to produce solid Form E. In another embodiment, Form E was made by recrystallization of the [2-(1H-indol-3-yl)-1H-imidazol-4-yl](3,4,5-trimethoxyphenyl)methanone hydrochloride salt that was added to ethanol at saturating concentrations at 25° C., heated to 45-50° C. to dissolve any solids, and solvent was fast evaporated under 1.5 psi of $N_2$ flow at 40° C. to produce Form E.

Yet another embodiment of the invention encompasses a crystalline polymorphic form of the [2-(1H-indol-3-yl)-1H-imidazol-4-yl](3,4,5-trimethoxyphenyl)methanone hydrochloride salt known as Form E1 characterized by an X-ray powder diffraction (XRD) pattern having peaks at 9.4, 17.3, 22.1, 23.4, and 24.8 2θ±0.2 2θ. The crystalline polymorph Form E1 of the [2-(1H-indol-3-yl)-1H-imidazol-4-yl](3,4,5-trimethoxyphenyl)methanone hydrochloride salt may be further characterized by an XRD pattern substantially as depicted in FIG. 30. Alternatively, the crystalline polymorph Form E1 of the [2-(1H-indol-3-yl)-1H-imidazol-4-yl](3,4,5-trimethoxyphenyl)methanone hydrochloride salt may be further characterized by XRD peaks at 13.0, 15.1, 18.1, 20.9, and 24.8 2θ±0.2 2θ. The crystalline polymorph Form E1 of the [2-(1H-indol-3-yl)-1H-imidazol-4-yl](3,4,5-trimethoxyphenyl)methanone hydrochloride salt was formed by the processes as described in Examples 4 and 5. One embodiment is directed to a process to make Form E1. In one aspect of this embodiment, Form E1 was made by recrystallization from 2-propanol/dichloromethane or 2-propanol/trichloromethane. In one aspect of this embodiment, Form E1 was made by recrystallization of the [2-(1H-indol-3-yl)-1H-imidazol-4-yl](3,4,5-trimethoxyphenyl)methanone hydrochloride salt that was added to 2-propanol/dichloromethane binary solvent mixture at saturating concentrations at 25° C., heated to 45-50° C. to dissolve solids, and fast evaporated under 1.5 psi of $N_2$ flow at 40° C., to produce solid Form E1. In another aspect of this embodiment, Form E1 was made by recrystallization of the [2-(1H-indol-3-yl)-1H-imidazol-4-yl](3,4,5-trimethoxyphenyl)methanone hydrochloride salt that was added to 2-propanol/trichloromethane binary solvent mixture at saturating concentrations at 25° C., heated to 45-50° C. to dissolve solids, and fast evaporated under 1.5 psi of $N_2$ flow at 40° C. to produce solid Form E1.

Another embodiment of the invention encompasses a crystalline polymorphic form of the [2-(1H-indol-3-yl)-1H-imidazol-4-yl](3,4,5-trimethoxyphenyl)methanone hydrochloride salt known as Form $F_H$ characterized by an X-ray powder diffraction (XRD) pattern having peaks at 9.06, 10.4, 18.85, 25.48, and 27.97 2θ±0.2 2θ. The crystalline polymorphic Form $F_H$ of the [2-(1H-indol-3-yl)-1H-imidazol-4-yl](3,4,5-trimethoxyphenyl)methanone hydrochloride salt may further be characterized by XRD peaks at 12.9, 20.9, and 26.14 2θ±0.2 2θ. Alternatively, the crystalline polymorphic Form $F_H$ of the [2-(1H-indol-3-yl)-1H-imidazol-4-yl](3,4,5-trimethoxyphenyl)methanone hydrochloride salt may be further characterized by an XRD pattern substantially as depicted in FIG. 38. The crystalline polymorphic Form $F_H$ of the [2-(1H-indol-3-yl)-1H-imidazol-4-yl](3,4,5-trimethoxyphenyl)methanone hydrochloride salt has a differential scanning calorimetry (DSC) thermogram exhibiting a large split endotherm with an onset of approximately 90.8° C. and peak maxima of 99.7° C. substantially as depicted in FIG. 39.

In another embodiment, the invention encompasses a crystalline polymorphic form of the [2-(1H-indol-3-yl)-1H-imidazol-4-yl](3,4,5-trimethoxyphenyl)methanone hydrochloride salt, known as Form $G_H$, characterized by an X-ray powder diffraction (XRD) pattern having peaks at 11.8, 14.5, 16.8, 23.1, and 28.5 2θ±0.2 2θ. The crystalline polymorphic Form $G_H$ of the [2-(1H-indol-3-yl)-1H-imidazol-4-yl](3,4,5-trimethoxyphenyl)methanone hydrochloride salt may be further characterized by XRD peaks at 10.4, 22.3, 24.7, and 25.3 2θ±0.2 2θ. Alternatively, the crystalline polymorphic Form $G_H$ of the [2-(1H-indol-3-yl)-1H-imidazol-4-yl](3,4,5-trimethoxyphenyl)methanone hydrochloride salt may be further characterized by an XRD pattern substantially as depicted in FIG. 40. The crystalline polymorphic Form $G_H$ of the [2-(1H-indol-3-yl)-1H-imidazol-4-yl](3,4,5-trimethoxyphenyl)methanone hydrochloride salt has a thermogravimetric analysis (TGA) thermogram with an average value of 4.8% weight loss at 150° C. (FIG. 41). The crystalline polymorphic Form $G_H$ of the [2-(1H-indol-3-yl)-1H-imidazol-4-yl](3,4,5-trimethoxyphenyl)methanone hydrochloride salt has a differential scanning calorimetry (DSC) thermogram with two endotherms with extrapolated onsets of 140.5° C. and 246.5° C. (FIG. 42).

In yet another embodiment, the invention encompasses a crystalline polymorphic form of the [2-(1H-indol-3-yl)-1H-imidazol-4-yl](3,4,5-trimethoxyphenyl)methanone hydrochloride salt known as Form H characterized by an X-ray powder diffraction (XRD) pattern having peaks at 11.8, 20.1, 23.6, 25.0, and 26.5 2θ±0.2 2θ. The crystalline polymorphic Form H of the [2-(1H-indol-3-yl)-1H-imidazol-4-yl](3,4,5-trimethoxyphenyl)methanone hydrochloride salt may be further characterized by XRD peaks at 8.6, 12.5, 18.6, 21.2, and 28.1 2θ±0.2 2θ. Alternatively, the crystalline polymorphic Form H of the [2-(1H-indol-3-yl)-1H-imidazol-4-yl](3,4,5-trimethoxyphenyl)methanone hydrochloride salt may be further characterized by an XRD pattern substantially as depicted in FIG. 43. The crystalline polymorphic Form H of the [2-(1H-indol-3-yl)-1H-imidazol-4-yl](3,4,5-trimethoxyphenyl)methanone hydrochloride salt has a thermogravimetric analysis (TGA) thermogram with an average value of 0.03% weight loss at 150° C. as depicted in FIG. 44. The crystalline polymorphic Form H of the [2-(1H-indol-3-yl)-1H-imidazol-4-yl](3,4,5-trimethoxyphenyl)methanone hydrochloride salt has a differential scanning calorimetry (DSC) thermogram with a melting onset endotherm with an onset of 247.5° C. with a peak maximum of 250.1° C. as depicted in FIG. 45. In one embodiment, Form H was made under ambient conditions. In some embodiments, Form H was made from Form E under ambient conditions. In some embodiments, Form H was made from Form E1 under ambient conditions. In some embodiment, Form H was made from other polymorphic forms under ambient conditions. In one embodiment, Form H was made by one of two competitive slurry experiments in which Form E and Form H were slurried in 2-butanol or 2-propanol for 1 day. In these embodiments, to avoid possible desolvation or physical change after isolation, the samples were not further dried before X-ray analysis. In one embodiment, a process to make Form H involved Form E and Form H co-incubated in 2-butanol for 1 day. In this embodiment, Form E and Form H were added to neat 2-butanol until saturated, the resulting suspension was agitated for 1 day at ambient temperature, and the solids were vacuum filtered and analyzed by XRD to determine the resulting form as Form H. In another embodiment, a process to make Form H involved Form E and Form H co-incubated in 2-propanol for 1 day. In this embodiment, Form E and Form H were added to neat 2-propanol until saturated, the resulting suspension was agitated for 1 day at ambient temperature, and the solids were vacuum filtered and analyzed by XRD to determine the resulting form as Form H.

In one embodiment, the invention encompasses a crystalline polymorphic form of the [2-(1H-indol-3-yl)-1H-imidazol-4-yl](3,4,5-trimethoxyphenyl)methanone hydrochloride salt known as Form I characterized by an X-ray powder diffraction (XRD) pattern having peaks at 10.0, 10.6, 16.6, 23.7, and 25.7 2θ±0.2 2θ. The crystalline polymorphic Form I of the [2-(1H-indol-3-yl)-1H-imidazol-4-yl](3,4,5-trimethoxyphenyl)methanone hydrochloride salt may be further characterized by XRD peaks at 11.8, 15.9, 26.7, and 27.6 2θ±0.2 2θ. Alternatively, the crystalline polymorphic Form I of the [2-(1H-indol-3-yl)-1H-imidazol-4-yl](3,4,5-trimethoxyphenyl)methanone hydrochloride salt may be further characterized by an XRD pattern substantially as depicted in FIG. 46.

In another embodiment, the invention encompasses the hydrochloride salt of [2-(1H-indol-3-yl)-1H-imidazol-4-yl](3,4,5-trimethoxyphenyl)methanone as characterized by at least the polymorphs Form A, Form B, Form $C_H$, Form D, Form E, Form E1, Form $F_H$, Form $G_H$, Form H and Form I as characterized by the X-ray powder diffraction (XRD) patterns as described herein and illustrated in FIG. 47.

One embodiment of the invention encompasses a crystalline form of the free base of [2-(1H-indol-3-yl)-1H-imidazol-4-yl](3,4,5-trimethoxyphenyl)methanone, known as Form II, characterized by an X-ray powder diffraction (XRD) pattern having peaks at 10.8, 15.3, 15.9, 18.6, and 25.9 2θ±0.2 2θ. The crystalline polymorphic Form II of the free base of [2-(1H-indol-3-yl)-1H-imidazol-4-yl](3,4,5-trimethoxyphenyl)methanone may be further characterized by an XRD pattern substantially as depicted in FIG. 1. Alternatively, the crystalline polymorphic Form II of the free base of [2-(1H-indol-3-yl)-1H-imidazol-4-yl](3,4,5-trimethoxyphenyl)methanone may be further characterized by XRD peaks at 14.4, 17.8, 20.0, 24.7, and 26.8 2θ±0.2 2θ.

Another embodiment of the invention encompasses a crystalline polymorphic form of the [2-(1H-indol-3-yl)-1H-imidazol-4-yl](3,4,5-trimethoxyphenyl)methanone hydrochloride salt characterized by an X-ray powder diffraction (XRD) pattern having peaks at 10.8, 13.3, 21.5, 23.1, and 35.2 2θ±0.2 2θ. This crystalline polymorphic form of the [2-(1H-indol-3-yl)-1H-imidazol-4-yl](3,4,5-trimethoxyphenyl)methanone hydrochloride salt may be further characterized by an XRD pattern substantially as depicted in FIG. 5. Alternatively, this crystalline polymorphic form of the [2-(1H-indol-3-yl)-1H-imidazol-4-yl](3,4,5-trimethoxyphenyl)methanone hydrochloride salt may be further characterized by XRD peaks at 10.5, 14.1, 16.1, and 26.2 2θ±0.2 2θ. This crystalline polymorphic form of the [2-(1H-indol-3-yl)-1H-imidazol-4-yl](3,4,5-trimethoxyphenyl)methanone hydrochloride salt was prepared according to Examples 1 and 2.

Yet another embodiment of the invention encompasses a crystalline polymorphic form of the [2-(1H-indol-3-yl)-1H-imidazol-4-yl](3,4,5-trimethoxyphenyl)methanone mesylate salt characterized by an X-ray powder diffraction (XRD) pattern having peaks at 8.3, 9.9, 10.9, 17.5, and 19.9 2θ±0.2 2θ. The crystalline polymorphic form of the [2-(1H-indol-3-yl)-1H-imidazol-4-yl](3,4,5-trimethoxyphenyl)methanone mesylate salt may be further characterized by an XRD pattern substantially as depicted in FIG. 15. Alternatively, the crystalline polymorphic form of the [2-(1H-indol-3-yl)-

1H-imidazol-4-yl](3,4,5-trimethoxyphenyl)methanone mesylate salt may be further characterized by XRD peaks at 12.1, 18.8, 21.9, 24.5, and 28.2 2θ±0.2 2θ. This crystalline polymorphic form of the [2-(1H-indol-3-yl)-1H-imidazol-4-yl](3,4,5-trimethoxyphenyl)methanone mesylate salt was prepared according to Examples 1 and 2.

In another embodiment of the invention, a polymorph of this invention is used to treat disease. Some of these embodiments encompass the use of a polymorph of this invention for the treatment of cancer. In some of these embodiments, the cancer is cancer of the prostate, breast, skin, or other organ, as is known by the skilled artisan. Some of these embodiments encompass the use of a polymorph of this invention for the treatment of a viral infection. In some of these embodiments, the viral infection is severe acute respiratory syndrome coronavirus 2 (SARS-CoV-2) or influenza. Some of these embodiments encompass the use of a polymorph of this invention for the treatment of an inflammatory disease. In some of these embodiments, the inflammatory disease affects the lungs. In other of these embodiments, the inflammatory disease is an infection. In some embodiments, the inflammatory disease has caused acute respiratory distress syndrome (ARDS). In some of these embodiments, the use of a polymorph of this invention for diseases includes any one of Form E, Form E1, or Form H of the [2-(1H-indol-3-yl)-1H-imidazol-4-yl](3,4,5-trimethoxyphenyl)methanone hydrochloride salt.

DETAILED DESCRIPTION OF THE INVENTION

Polymorphism is the ability of a chemical entity to exist in different three-dimensional arrangements in the solid state. Different polymorphic forms of a compound can have different physicochemical properties. [2-(1H-Indol-3-yl)-1H-imidazol-4-yl](3,4,5-trimethoxyphenyl)methanone is a tubulin inhibitor compound with applications for treating cancer, viral infections such as severe acute respiratory syndrome coronavirus 2 (SARS-CoV-2) and influenza, and anti-inflammatory diseases such as acute respiratory distress syndrome (ARDS). The invention is directed to the synthesis (methods or processes to make) and composition of matter of stable polymorphic forms of the compound [2-(1H-indol-3-yl)-1H-imidazol-4-yl](3,4,5-trimethoxyphenyl)methanone and its pharmaceutically acceptable salts and solvates, and their methods of use. Particular emphasis is given to the characterization of the [2-(1H-indol-3-yl)-1H-imidazol-4-yl](3,4,5-trimethoxyphenyl)methanone hydrochloride salt and its hydrates. Not to be limited by theory, but it is believed that a stable polymorphic form would be helpful during transportation and formulation of the compound, as well as obtaining a generally pure compound. The most desirable form is the most thermodynamically stable polymorphic form. To determine the most thermodynamically stable compounds and polymorphs thereof, samples of the free base, and its pharmaceutically acceptable salts, solvates, and hydrates of [2-(1H-indol-3-yl)-1H-imidazol-4-yl](3,4,5-trimethoxyphenyl)methanone were synthesized by methods described herein and characterized using X-ray powder diffraction (XRD), differential scanning calorimetry (DSC), thermogravimetric analysis (TGA), and other methods as described herein. Further, the skilled artisan would know that these compounds and their novel polymorphs may possess advantages in terms of their use to treat cancer, viral infections, and inflammatory diseases such as increased solubility or bioavailability of the API, or increased stability of the pharmaceutical product containing the API.

Figure 1:
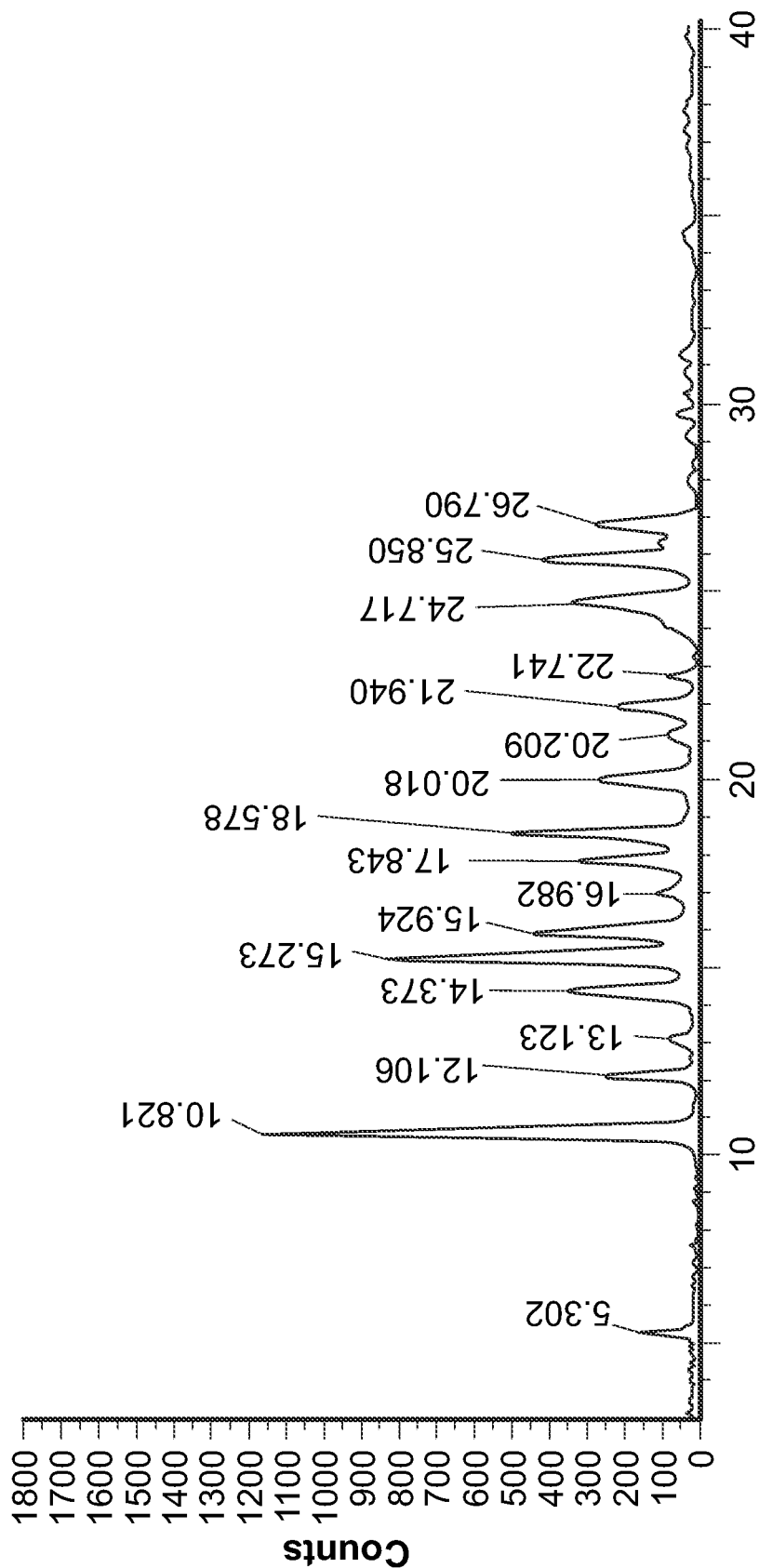
FIG. 1 illustrates the X-ray powder diffraction (XRD) pattern for polymorphic crystalline Form II of the [2-(1H-indol-3-yl)-1H-imidazol-4-yl](3,4,5-trimethoxyphenyl)methanone free base (Form II).
Figure 4:
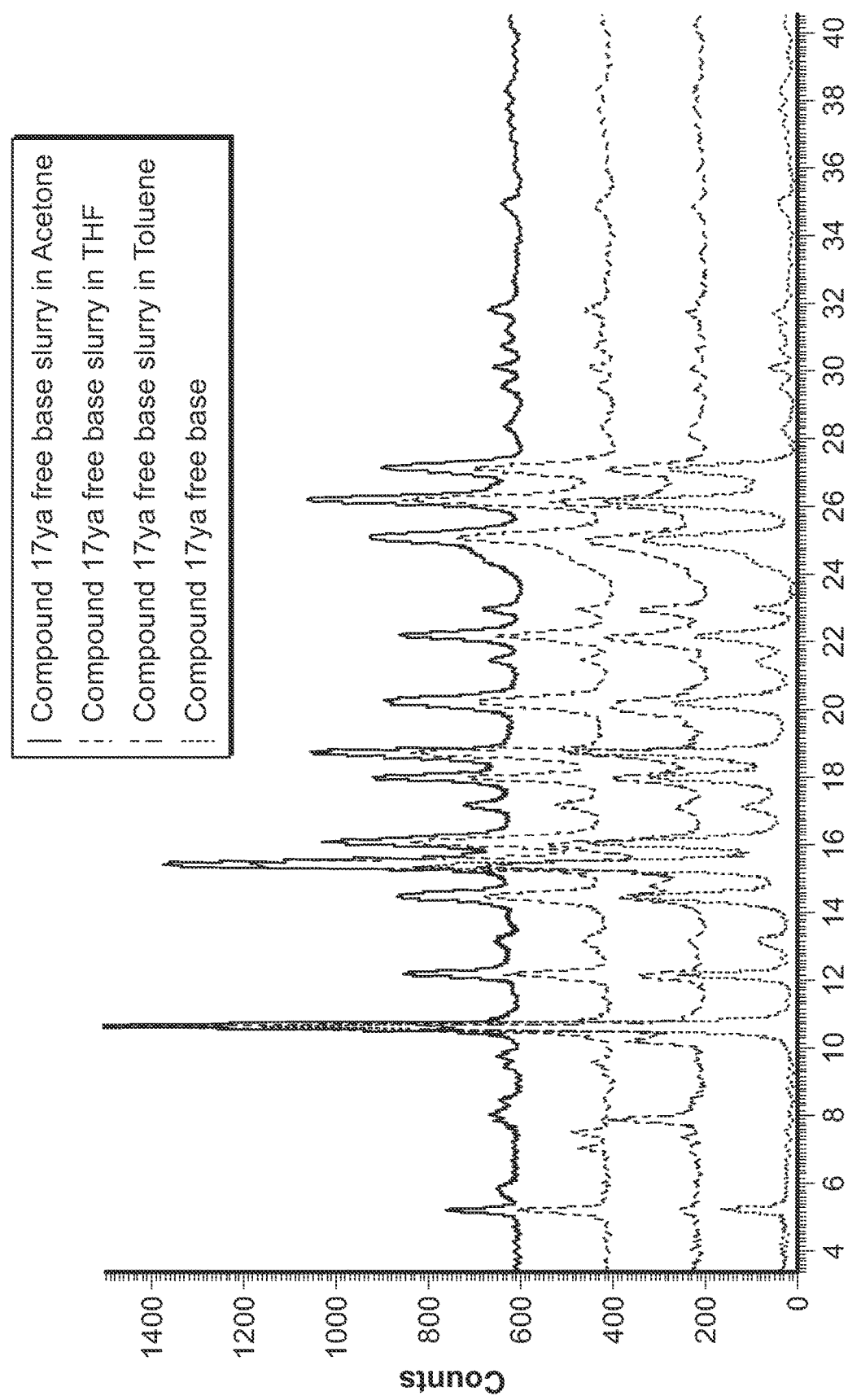
FIG. 4 illustrates [2-(1H-indol-3-yl)-1H-imidazol-4-yl](3,4,5-trimethoxyphenyl)methanone free base samples slurried in acetone (top spectrum), THF (second spectrum down), and toluene (third spectrum down) that yielded similar X-ray powder diffraction (XRD) patterns that were the same as Form II of FIG. 1, an indication that the XRD pattern of Form II represented the stable form of the free base of [2-(1H-indol-3-yl)-1H-imidazol-4-yl](3,4,5-trimethoxyphenyl)methanone.

Characterization of the Free Base of [2-(1H-indol-3-yl)-1H-imidazol-4-yl](3,4,5-trimethoxyphenyl)methanone (Example 1): A process to make a crystalline polymorphic Form II of [2-(1H-indol-3-yl)-1H-imidazol-4-yl](3,4,5-trimethoxyphenyl)methanone free base (Form II) was by recrystallization of an amorphous form (Form I) of the free base (FIG. 1). Other processes to make Form II of the free base included non-competitive single solvent slurry experiments performed by the process described in Example 4 using the amorphous form of [2-(1H-indol-3-yl)-1H-imidazol-4-yl](3,4,5-trimethoxyphenyl)methanone free base (Form I). An excess amount of free base (Form I) was slurried in methanol, ethanol, acetone, acetonitrile, ethyl acetate, THF or toluene. The suspensions were slurried for several days at ambient temperature. The solids were collected by filtration and analyzed by XRD. Samples slurried in acetone, THF and toluene yielded Form II of the free base as shown by the superimposition of XRD spectra from these experiments (FIG. 4). FIG. 1 illustrates the X-ray powder diffraction (XRD) pattern for Form II of the free base. Form II of the free base was characterized by an XRD pattern having peaks at about 10.8, 15.3, 15.9, 18.6, and 25.9 2θ±0.2.

Form II of the free base was further characterized by an XRD pattern having peaks at 14.4, 17.8, 20.0, 24.7, and 26.8 2θ±0.2 2θ.

Figure 2:
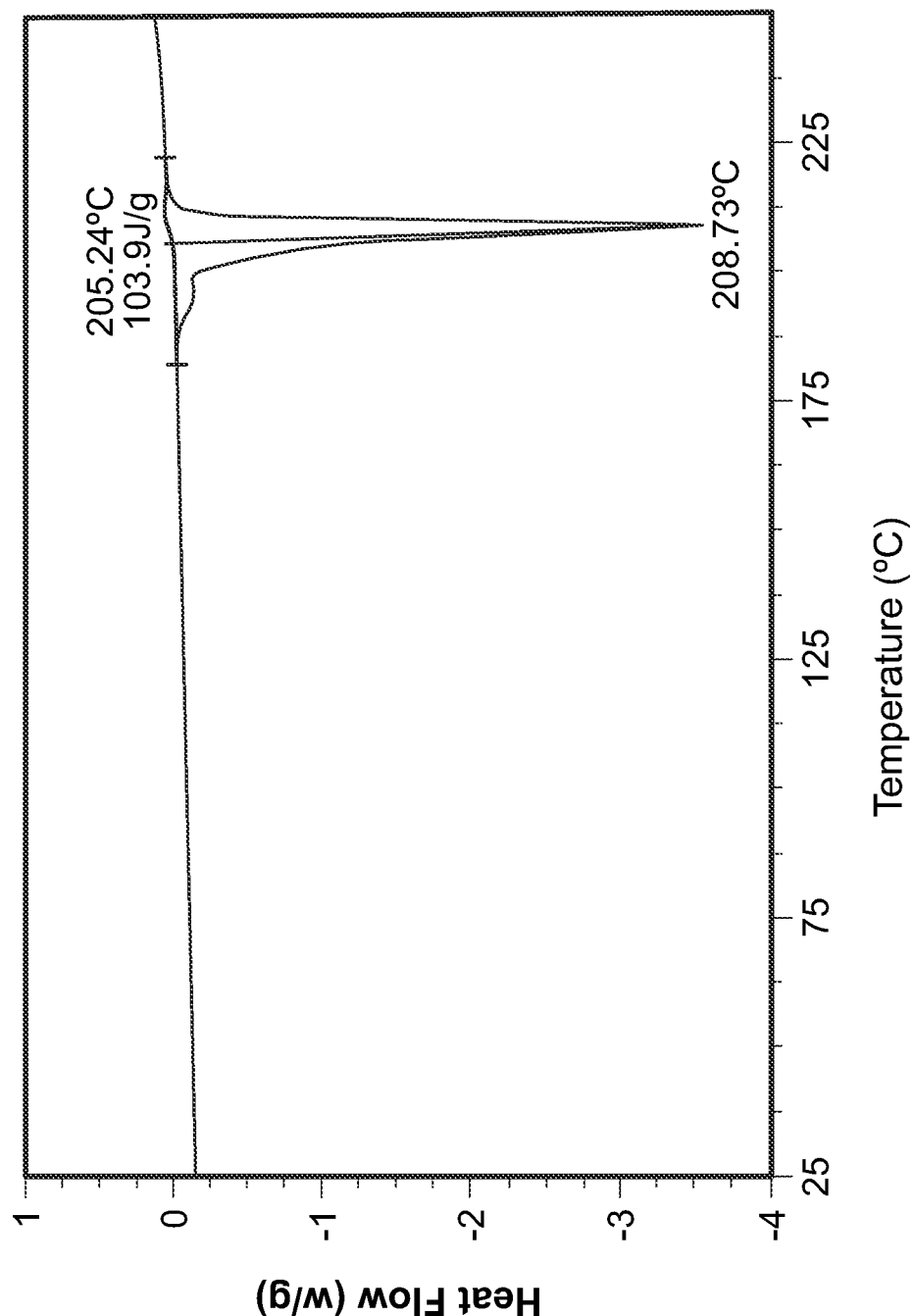
FIG. 2 illustrates the differential scanning calorimetry (DSC) thermogram for Form II.
Figure 3:
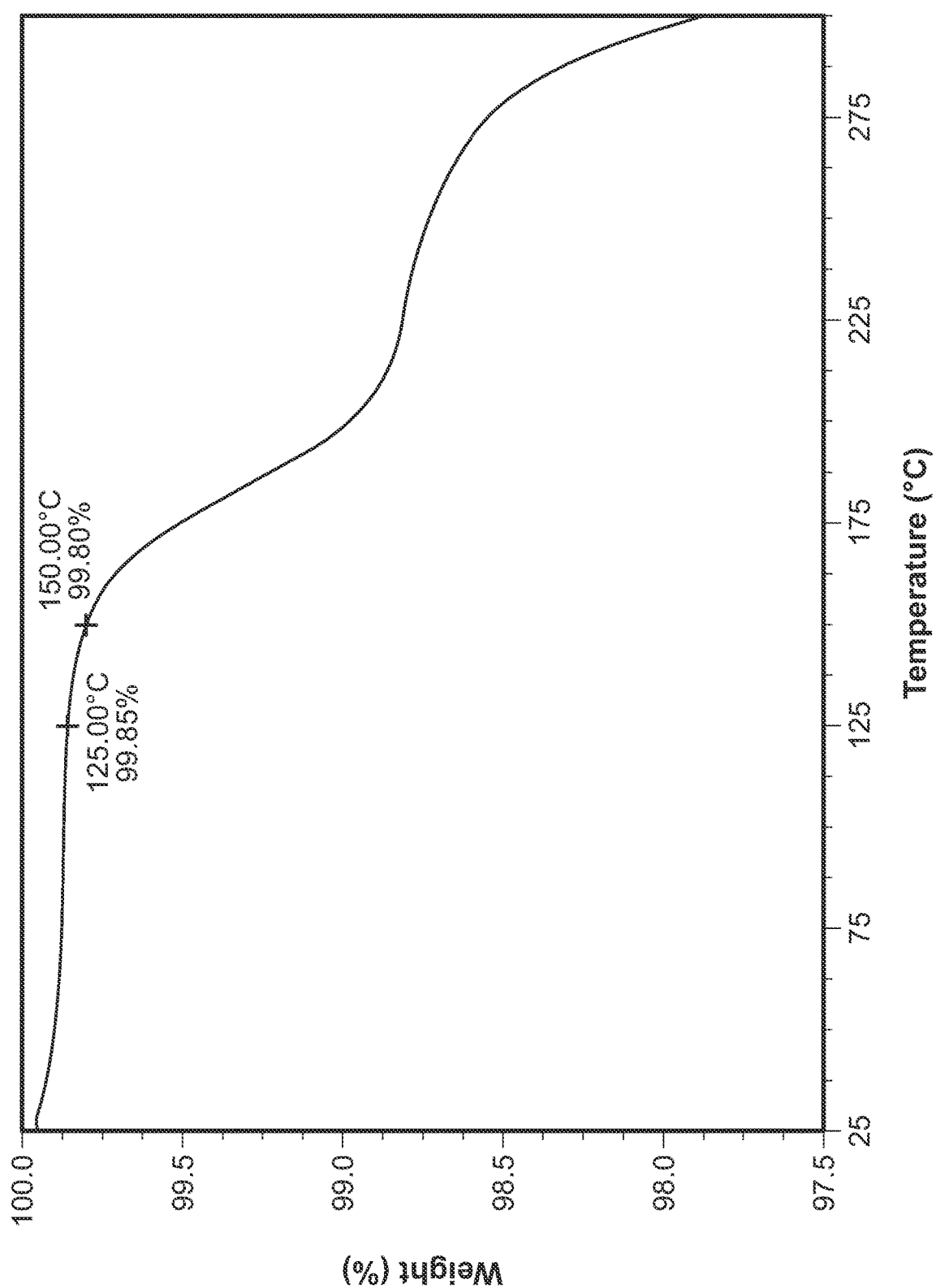
FIG. 3 illustrates the thermogravimetric analysis (TGA) thermogram for Form II.

As illustrated in FIG. 2, the DSC thermogram for Form II of [2-(1H-indol-3-yl)-1H-imidazol-4-yl](3,4,5-trimethoxyphenyl)methanone free base showed a sharp melting endotherm with an extrapolated onset temperature of 205.2° C., with a peak temperature 208.7° C. The DSC indicated an enthalpy value of 103.9 J/g. A small endothermic dip observed at 190° C. could indicate a phase transformation. The TGA thermogram indicated that [2-(1H-indol-3-yl)-1H-imidazol-4-yl](3,4,5-trimethoxyphenyl)methanone free base Form II had about 0.2 wt % loss at 150° C. and continued to lose weight as shown in FIG. 3. As mentioned above, [2-(1H-indol-3-yl)-1H-imidazol-4-yl](3,4,5-trimethoxyphenyl)methanone free base samples of Form I slurried (as described in Example 4) in acetone, THF, or toluene yielded XRD patterns similar to FIG. 1, an indication that the XRD pattern of Form II represented the stable form of the free base (FIG. 4). This also indicates that slurry processes to make Form II of the free base from the amorphous Form I of the free base can be achieved using, alternatively, acetone, THF, or toluene.

Salt Screening of the free base [2-(1H-indol-3-yl)-1H-imidazol-4-yl](3,4,5-trimethoxyphenyl)methanone (Example 1): A salt screening study was performed to identify suitable polymorphic salts formed by reaction with from a library of salt forming acids with [2-(1H-indol-3-yl)-1H-imidazol-4-yl](3,4,5-trimethoxyphenyl)methanone free base. Originally, the characterization of salts was done at a small scale (40 mg) with four salts and deemed to produce desirable polymorphs. The small scale synthesis and characterization were performed as described in Example 1. The preferred salts were the hydrochloride, citrate, phosphate, and mesylate salts of [2-(1H-indol-3-yl)-1H-imidazol-4-yl](3,4,5-trimethoxyphenyl)methanone. Each salt was scaled up and analyzed for crystallinity, thermal properties, aqueous solubility and hygroscopicity. All polymorphs or salts were contemplated for processability, therapeutic use, and other factors. The scale-up salt syntheses were described in Example 2 and Table 1 (in Example 2).

Scale-up of the hydrochloride, citrate, phosphate, and mesylate salts (Example 2): The monohydrochloride (HCl), citrate, monophosphate (phosphate), and mesylate polymorphic salts were selected for scale-up. The salts were prepared at 200-500 mg scale to facilitate additional testing and determine reproducibility. Typical procedures are found in Table 1 of Example 2. The solids were collected by evaporation at ambient condition with nitrogen purge at ~2 psi. All solids yielded the same XRD patterns as seen in the earlier experiments at small scale and were reproducible.

A salt screening study was performed to identify suitable polymorphic salts formed by reaction of a library of salt forming acids with [2-(1H-indol-3-yl)-1H-imidazol-4-yl](3,4,5-trimethoxyphenyl)methanone free base, as described in Examples 1 and 2. Originally, the characterization of salts was done at a small scale (40 mg) with four salts and deemed to produce desirable polymorphs. The small-scale synthesis and characterization were performed as described in Example 1. The preferred salts from Example 1 were the hydrochloride, citrate, phosphate, and mesylate salts of [2-(1H-indol-3-yl)-1H-imidazol-4-yl](3,4,5-trimethoxyphenyl)methanone. Each salt was scaled up and analyzed for crystallinity, thermal properties, aqueous solubility and hygroscopicity. All polymorphs or salts were contemplated for processability, therapeutic use, and other factors. The scale-up salt syntheses were described in this example and Table 1.

One embodiment of this invention is directed to a hydrochloride salt of [2-(1H-indol-3-yl)-1H-imidazol-4-yl](3,4,5-trimethoxyphenyl)methanone. Another embodiment of this invention is directed to any of the polymorphs of the hydrochloride salt of [2-(1H-indol-3-yl)-1H-imidazol-4-yl](3,4,5-trimethoxyphenyl)methanone, as characterized herein. The polymorphic forms of the hydrochloride salt of [2-(1H-indol-3-yl)-1H-imidazol-4-yl](3,4,5-trimethoxyphenyl)methanone were differentiated by X-ray powder diffraction (XRD) spectra and further characterized by DSC, TGA, DVS, and other methods as described herein. Some embodiments of the invention encompass the processes by which a particular polymorph may be synthesized. In some embodiments, a polymorph of interest may be synthesized by one or more of recrystallization processes, or non-competitive or competitive slurry processes as described herein for each polymorph. In another embodiment of the invention, a particular polymorph is used in a pharmaceutical product used to treat disease In some embodiments, a particular polymorph is used in a pharmaceutical product used for treatment of cancer. In some embodiments, the cancer is cancer of the prostate, breast, skin such as melanoma, or other organ, as is known by the skilled artisan. In some embodiments, a particular polymorph is used in a pharmaceutical product used for treatment of a viral infection. In some embodiments, the viral infection is severe acute respiratory syndrome coronavirus 2 (SARS-CoV-2) or influenza. In some embodiments, a particular polymorph is used in a pharmaceutical product used for the treatment of an inflammatory disease. In some embodiments, the inflammatory disease affects the lungs. In some embodiments, the inflammatory disease is an infection. In some embodiments, the inflammatory disease has caused acute respiratory distress syndrome (ARDS).

As used herein, "pharmaceutical product" means therapeutically effective amounts of a specific polymorph of the [2-(1H-indol-3-yl)-1H-imidazol-4-yl](3,4,5-trimethoxyphenyl)methanone hydrochloride salt together with various excipients such as suitable diluents, preservatives, solubilizers, emulsifiers, adjuvant and/or carriers.

Figure 5:
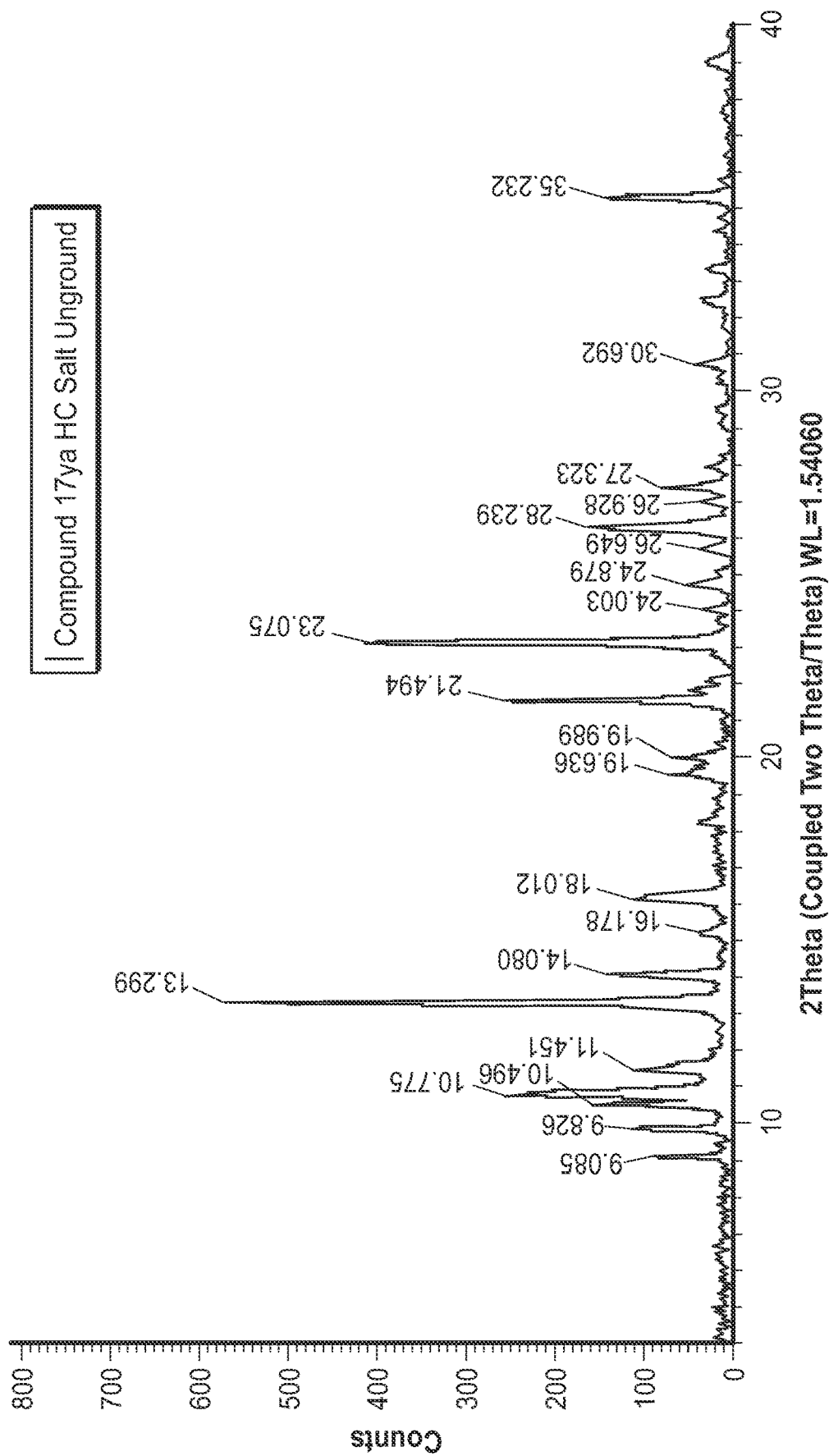
FIG. 5 illustrates the XRD pattern of a polymorphic form of the [2-(1H-indol-3-yl)-1H-imidazol-4-yl](3,4,5-trimethoxyphenyl)methanone hydrochloride salt indicating the salt form was crystalline. This unnamed crystalline polymorphic form of the hydrochloride salt was produced by the processes of Examples 1 or 2 (small scale synthesis and scale-up of the hydrochloride salt).

One embodiment of the invention is directed to a polymorph of the hydrochloride salt of [2-(1H-indol-3-yl)-1H-imidazol-4-yl](3,4,5-trimethoxyphenyl)methanone characterized by an XRD pattern substantially as depicted in FIG. 5. In another embodiment, this crystalline polymorphic form of [2-(1H-indol-3-yl)-1H-imidazol-4-yl](3,4,5-trimethoxyphenyl)methanone hydrochloride salt was characterized by an XRD pattern having peaks at about 10.8, 13.3, 21.5, 23.1, and 35.2 2θ±0.2 2θ. In another embodiment, this crystalline polymorphic form of the [2-(1H-indol-3-yl)-1H-imidazol-4-yl](3,4,5-trimethoxyphenyl)methanone hydrochloride salt was further characterized by an XRD pattern having peaks at 10.5, 14.1, 16.1, and 26.2 2θ±0.2 2θ.

Figure 35:
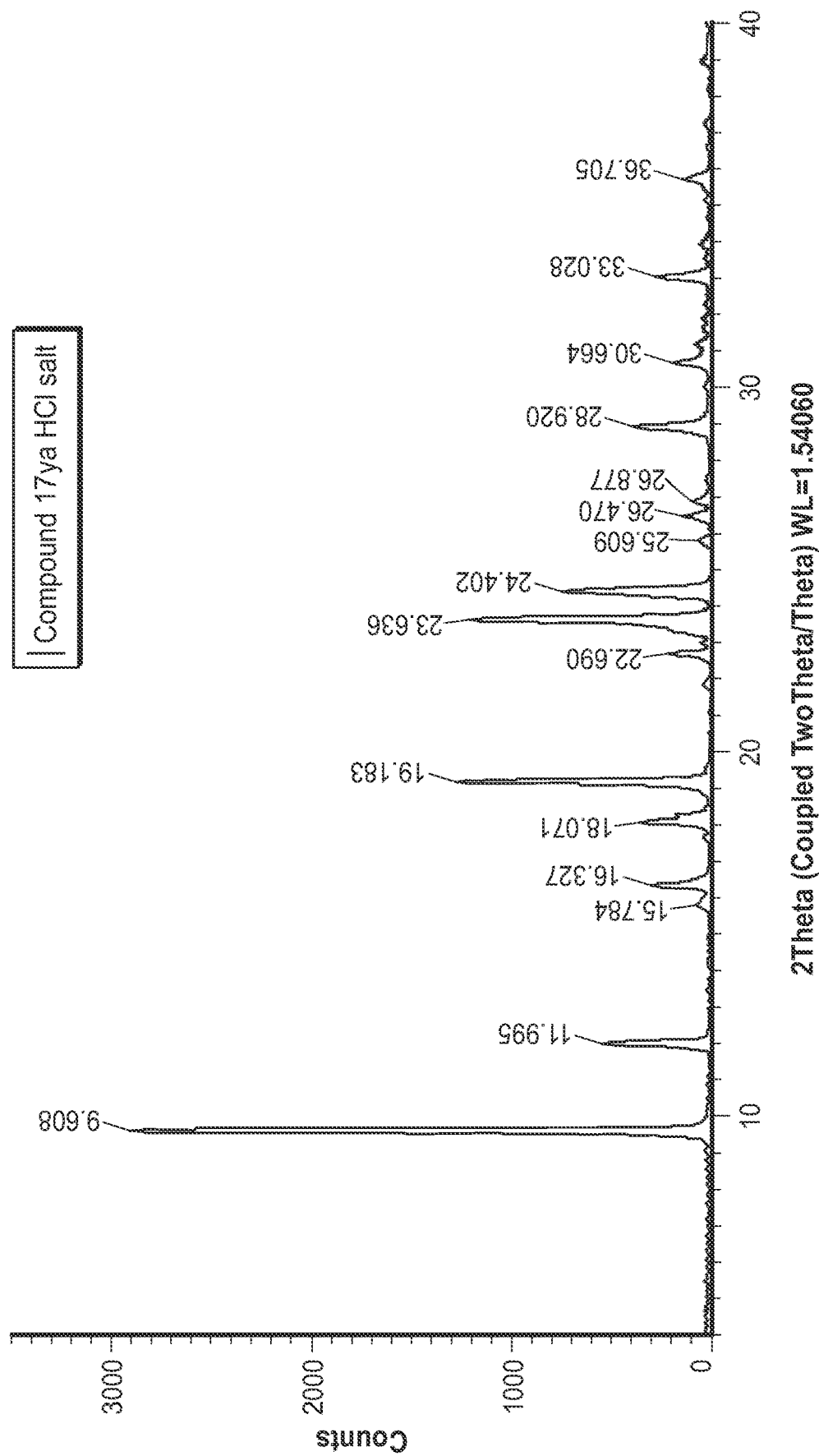
FIG. 35 illustrates the XRD pattern of the polymorphic Form A of the [2-(1H-indol-3-yl)-1H-imidazol-4-yl](3,4,5-trimethoxyphenyl)methanone hydrochloride salt that was prepared in Example 3 (Form A) via recrystallization from 1-propanol/nitromethane, as described therein.

Another embodiment of the invention is directed to a crystalline polymorph Form A of the [2-(1H-indol-3-yl)-1H- imidazol-4-yl](3,4,5-trimethoxyphenyl)methanone hydrochloride salt characterized by an XRD pattern substantially as depicted in FIG. 35. In one aspect of this embodiment, Form A was characterized by an XRD pattern having peaks at about 9.6, 12.0, 19.2, 23.6, and 24.4 2θ±0.2 2θ. In another aspect of this embodiment, Form A was characterized by an XRD pattern having peaks at about 16.3, 18.1, and 28.9 2θ±0.2 2θ. One embodiment is directed to a process to make Form A. In one aspect of this embodiment, Form A was made by recrystallization from a 1-propanol/nitromethane binary solvent mixture. In another aspect of this embodiment, Form A was made from [2-(1H-indol-3-yl)-1H-imidazol-4-yl](3,4,5-trimethoxyphenyl)methanone hydrochloride salt that was added to 1-propanol/nitromethane at saturating concentrations at 25° C., heated to 45-50° C. to dissolve solids, and fast evaporated under 1.5 psi of $N_2$ flow at 40° C. to produce solid Form A. In another embodiment of the invention, Form A is used in a pharmaceutical product used to treat disease. Some of these embodiments encompass the use of Form A in a pharmaceutical product used for the treatment of cancer. In some of these embodiments, the cancer is cancer of the prostate, breast, skin, or other organ, as is known by the skilled artisan. Some of these embodiments encompass the use of Form A in a pharmaceutical product used for the treatment of a viral infection. In some of these embodiments, the viral infection is severe acute respiratory syndrome coronavirus 2 (SARS-CoV-2) or influenza. Some of these embodiments encompass the use of Form A in a pharmaceutical product used for the treatment of an inflammatory disease. In some of these embodiments, the inflammatory disease affects the lungs. In other of these embodiments, the inflammatory disease is an infection. In some embodiments, the inflammatory disease has caused acute respiratory distress syndrome (ARDS).

Figure 18:
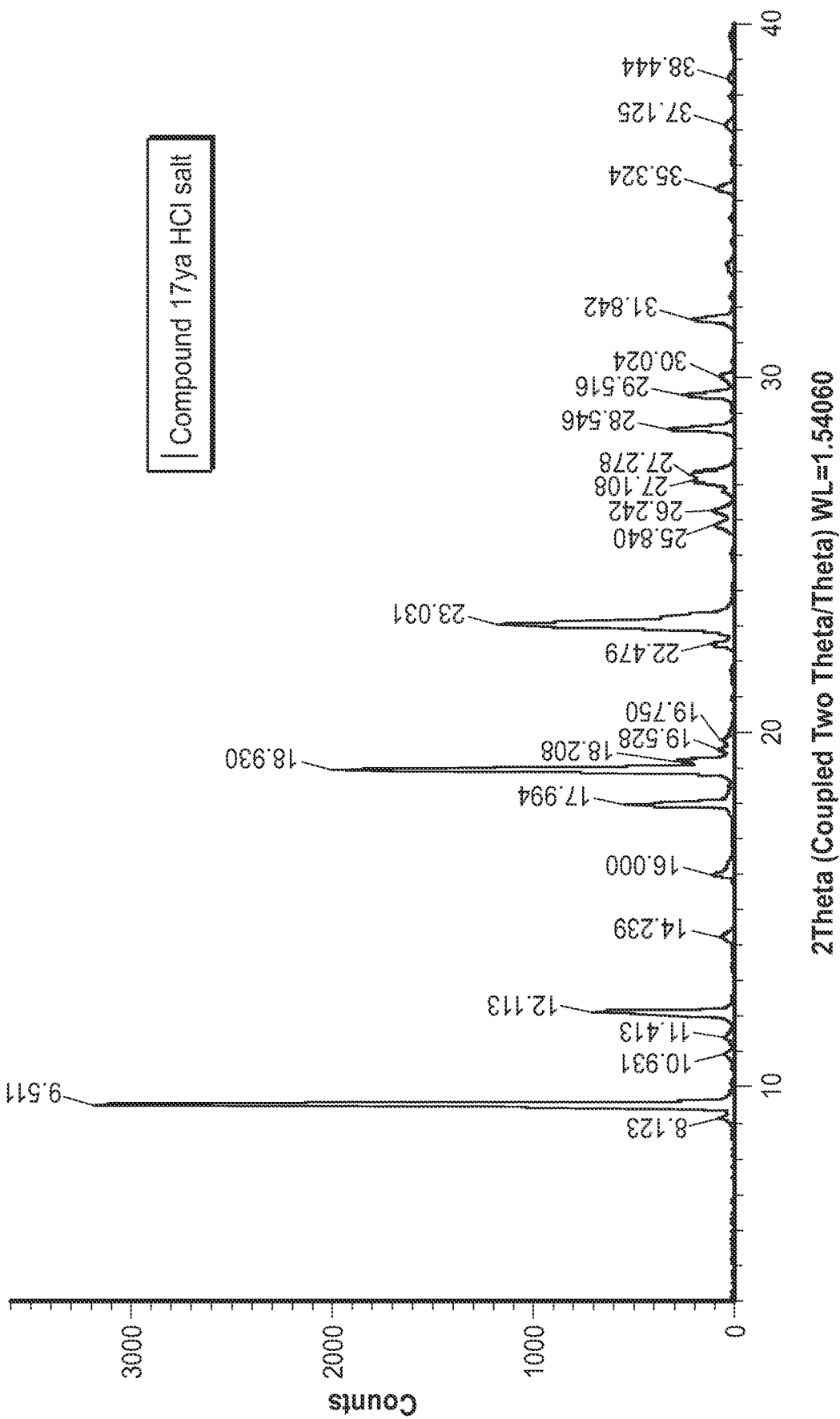
FIG. 18 illustrates the XRD pattern of the polymorphic Form B of the [2-(1H-indol-3-yl)-1H-imidazol-4-yl](3,4,5-trimethoxyphenyl)methanone hydrochloride salt which was made as described in Example 3 via recrystallization from methanol/acetonitrile binary solvent mixture (Form B).

Another embodiment of the invention is directed to a crystalline polymorph Form B of the [2-(1H-indol-3-yl)-1H-imidazol-4-yl](3,4,5-trimethoxyphenyl)methanone hydrochloride salt characterized by an XRD pattern substantially as depicted in FIG. 18. In one aspect of this embodiment, Form B was characterized by an XRD pattern having peaks at about 9.5, 12.1, 18.0, 18.9, and 23.0 2θ±0.2 2θ. In another aspect of this embodiment, Form B was characterized by an XRD pattern having peaks at about 19.2, 28.5, 29.5, and 31.8 2θ±0.2 2θ. One embodiment is directed to the preparation of Form B. In one aspect of this embodiment, Form B was made by recrystallization from a methanol/acetonitrile binary solvent mixture. In another aspect of this embodiment, Form B was made from [2-(1H-indol-3-yl)-1H-imidazol-4-yl](3,4,5-trimethoxyphenyl)methanone hydrochloride salt that was added to methanol/acetonitrile at saturating concentrations at 25° C., heated to 45-50° C. to dissolve solids, and fast evaporated under 1.5 psi of $N_2$ flow at 40° C. to produce solid Form B. In another aspect of this embodiment, Form B was made by competitive slurry of Form $C_H$ and Form B in ethyl acetate. In this embodiment, Form B was made by addition of excess of Form $C_H$ and Form B to neat ethyl acetate until saturated, the resulting suspension was agitated for about two weeks at ambient temperature, and the solids were vacuum filtered and analyzed by XRD to determine the resulting form as Form B. In another embodiment of the invention, Form B is used in a pharmaceutical product used to treat disease. Some of these embodiments encompass the use of Form B in a pharmaceutical product used for the treatment of cancer. In some of these embodiments, the cancer is cancer of the prostate, breast, skin, or other organ, as is known by the skilled artisan. Some of these embodiments encompass the use of Form B in a pharmaceutical product used for the treatment of a viral infection. In some of these embodiments, the viral infection is severe acute respiratory syndrome coronavirus 2 (SARS-CoV-2) or influenza. Some of these embodiments encompass the use of Form B in a pharmaceutical product used for the treatment of an inflammatory disease. In some of these embodiments, the inflammatory disease affects the lungs. In other of these embodiments, the inflammatory disease is an infection. In some embodiments, the inflammatory disease has caused acute respiratory distress syndrome (ARDS).

Figure 22:
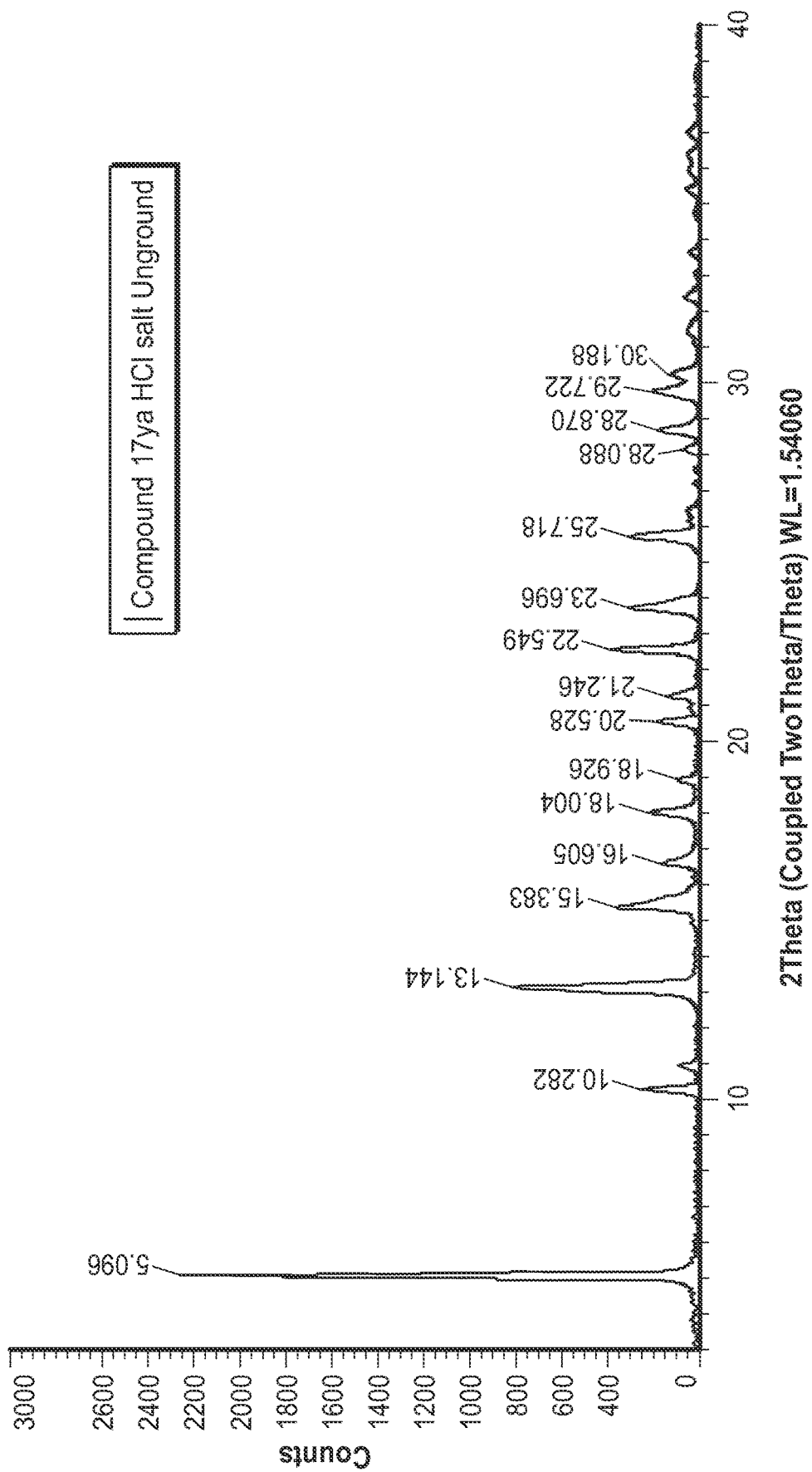
FIG. 22 illustrates the XRD pattern of the polymorphic Form $C_H$ of the [2-(1H-indol-3-yl)-1H-imidazol-4-yl](3,4,5-trimethoxyphenyl)methanone hydrochloride salt which was made as described in Example 6 (Form $C_H$); which was a hydrate.

Another embodiment of the invention is directed to a crystalline polymorph Form $C_H$ of the [2-(1H-indol-3-yl)-1H-imidazol-4-yl](3,4,5-trimethoxyphenyl)methanone hydrochloride salt characterized by an XRD pattern substantially as depicted in FIG. 22. In one aspect of this embodiment, Form $C_H$ was characterized by an XRD pattern having peaks at about 5.1, 13.1, 16.6, 22.5, and 25.7 2θ±0.2 2θ. In another aspect of this embodiment, Form $C_H$ was characterized by an XRD pattern having peaks at about 10.3, 18.0, 23.7, 28.7, and 29.7 2θ±0.2 2θ. In another embodiment of the invention, Form $C_H$ is used in a pharmaceutical product used to treat disease. Some of these embodiments encompass the use of Form $C_H$ in a pharmaceutical product used for the treatment of cancer. In some of these embodiments, the cancer is cancer of the prostate, breast, skin, or other organ, as is known by the skilled artisan. Some of these embodiments encompass the use of Form $C_H$ in a pharmaceutical product used for the treatment of a viral infection. In some of these embodiments, the viral infection is severe acute respiratory syndrome coronavirus 2 (SARS-CoV-2) or influenza. Some of these embodiments encompass the use of Form $C_H$ in a pharmaceutical product used for the treatment of an inflammatory disease. In some of these embodiments, the inflammatory disease affects the lungs. In other of these embodiments, the inflammatory disease is an infection. In some embodiments, the inflammatory disease has caused acute respiratory distress syndrome (ARDS).

Figure 25:
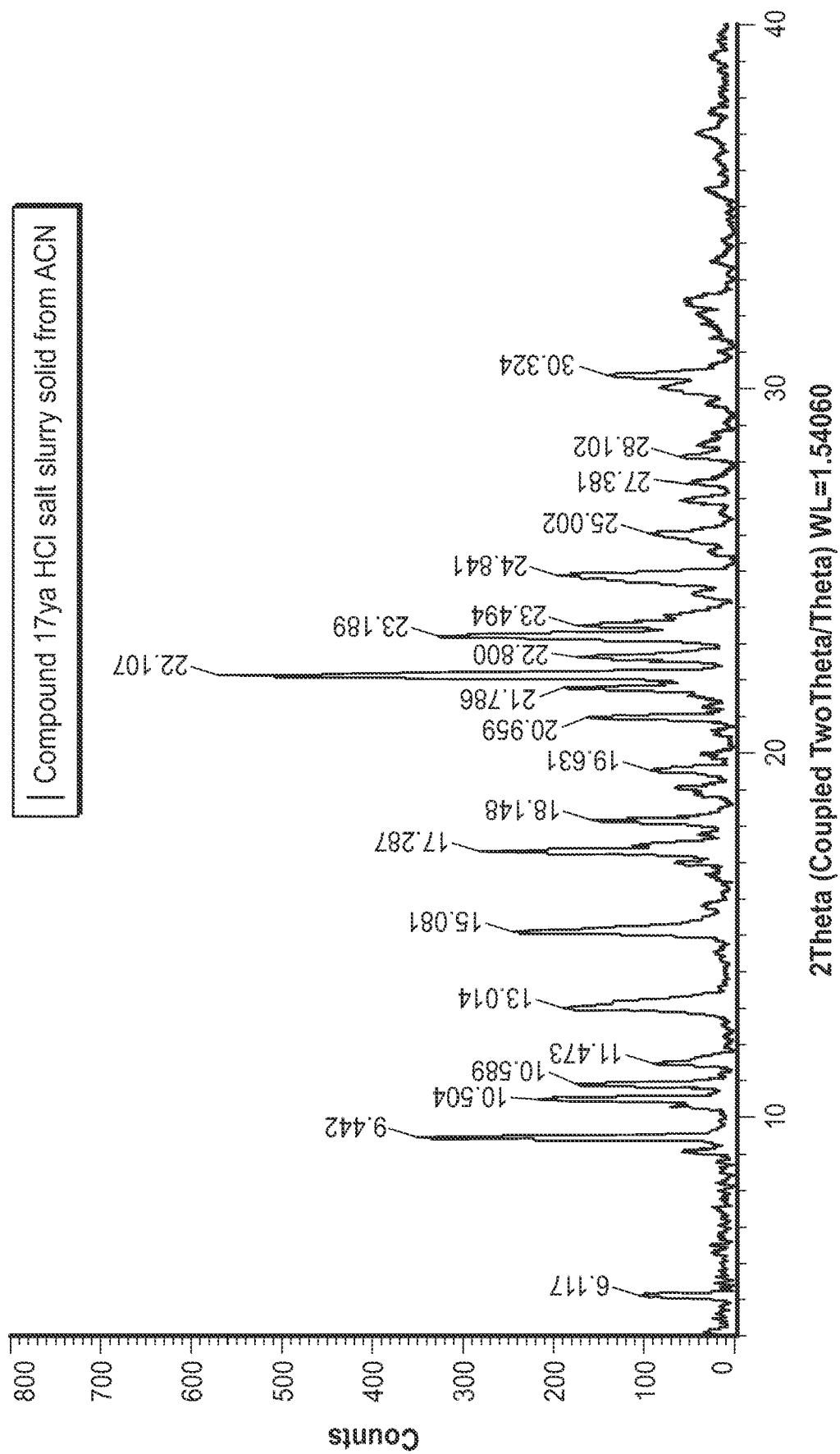
FIG. 25 illustrates the XRD pattern of the polymorphic Form D of the [2-(1H-indol-3-yl)-1H-imidazol-4-yl](3,4,5-trimethoxyphenyl)methanone hydrochloride salt which was made by the non-competitive slurry processes described in Example 4 (Form D).

Another embodiment of the invention is directed to a crystalline polymorph Form D of the [2-(1H-indol-3-yl)-1H-imidazol-4-yl](3,4,5-trimethoxyphenyl)methanone hydrochloride salt characterized by an XRD pattern substantially as depicted in FIG. 25. In one aspect of this embodiment, Form D was characterized by an XRD pattern having peaks at about 9.4, 15.1, 17.3, 22.1, and 23.2 2θ±0.2 2θ. In another aspect of this embodiment, Form D was characterized by an XRD pattern having peaks at about 10.5, 18.1, 22.8, 24.8, and 30.3 2θ±0.2 2θ. One embodiment is directed to the preparation of Form D. In one aspect of this embodiment, Form D was made by non-competitive slurry experiments in which Form B was slurried in either of the non-aqueous solvents acetone or acetonitrile for 14 days. In one embodiment, a process to make Form D involved non-competitive slurry of Form B in acetone for 14 days. In this embodiment, excess of Form B was added to neat acetone until saturated, the resulting suspension was agitated for fourteen days at ambient temperature, and the solids were vacuum filtered and analyzed by XRD to determine the resulting form as Form D. In another embodiment, a process to make Form D involved non-competitive slurry of Form B in acetonitrile for 14 days. In this embodiment, excess of Form B was added to neat acetonitrile until saturated, the resulting suspension was agitated for fourteen days at ambient temperature, and the solids were vacuum filtered and analyzed by XRD to determine the resulting form as Form D. In another embodiment of the invention, Form D is used in a pharmaceutical product used to treat disease. Some of these embodiments encompass the use of Form D in a pharmaceutical product used for the treatment of cancer. In some of these embodiments, the cancer is cancer of the prostate, breast, skin, or other organ, as is known by the skilled artisan. Some of these embodiments encompass the use of Form D in a pharmaceutical product used for the treatment of a viral infection. In some of these embodiments, the viral infection is severe acute respiratory syndrome coronavirus 2 (SARS-CoV-2) or influenza. Some of these embodiments encompass the use of Form D in a pharmaceutical product used for the treatment of an inflammatory disease. In some of these embodiments, the inflammatory disease affects the lungs. In other of these embodiments, the inflammatory disease is an infection. In some embodiments, the inflammatory disease has caused acute respiratory distress syndrome (ARDS).

Figure 29:
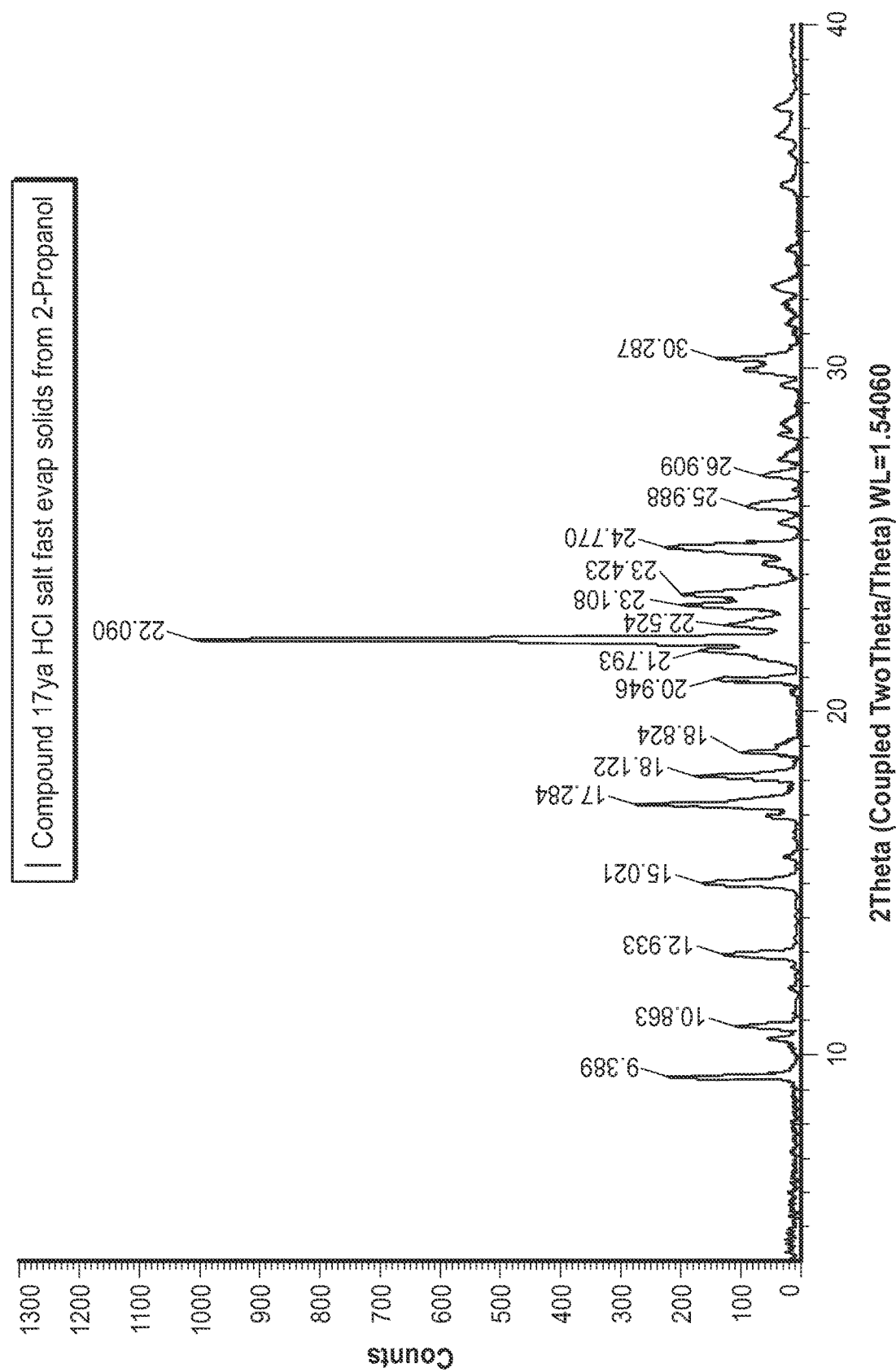
FIG. 29 illustrates the XRD pattern of the polymorphic Form E of the [2-(1H-indol-3-yl)-1H-imidazol-4-yl](3,4,5-trimethoxyphenyl)methanone hydrochloride salt which was made as the result of multiple processes described in Examples 3 and 5 (Form E).

Another embodiment of the invention is directed to a crystalline polymorph Form E of the [2-(1H-indol-3-yl)-1H-imidazol-4-yl](3,4,5-trimethoxyphenyl)methanone hydrochloride salt characterized by an XRD pattern substantially as depicted in FIG. 29. In one aspect of this embodiment, Form E was characterized by an XRD pattern having peaks at about 9.4, 17.3, 22.1, 23.4, and 24.8 2θ±0.2 2θ. In another aspect of this embodiment, Form E was characterized by an XRD pattern having peaks at about 12.9, 15.0, 18.1, 21.0, and 30.3 2θ±0.2 2θ. The two diffraction patterns of Form E and Form E1 appear to be very similar except for minor differences between the two patterns in the 10-12° 2θ region.

One embodiment is directed to the preparation of Form E. In one aspect of this embodiment, Form E was made by recrystallization from 2-propanol, 1-propanol/1-dioxane mixture, or ethanol. In one aspect of this embodiment, Form E was made by recrystallization of the [2-(1H-indol-3-yl)-1H-imidazol-4-yl](3,4,5-trimethoxyphenyl)methanone hydrochloride salt that was added to 2-propanol at saturating concentrations at 25° C., heated to 45-50° C. to dissolve solids, and fast evaporated under 1.5 psi of $N_2$ flow at ambient temperature to produce solid Form E. In another aspect of this embodiment, Form E was made by recrystallization of the [2-(1H-indol-3-yl)-1H-imidazol-4-yl](3,4,5-trimethoxyphenyl)methanone hydrochloride salt that was added to 1-propanol/1-dioxane mixture at saturating concentrations at 25° C., and solvent was slowly evaporated at ambient temperature to produce solid Form E. In another embodiment, Form E was made by recrystallization of the [2-(1H-indol-3-yl)-1H-imidazol-4-yl](3,4,5-trimethoxyphenyl)methanone hydrochloride salt that was added to ethanol at saturating concentrations at 25° C., heated to 45-50° C. to dissolve any solids, and solvent was fast evaporated under 1.5 psi of $N_2$ flow at 40° C. to produce Form E. In one embodiment, Form E was made by competitive slurry experiments in which binary combinations of Form A, Form B, and Form D were slurried in 1-propanol for about two weeks. In one aspect of this embodiment, a process to make Form E involved Form B and Form D co-incubated in 1-propanol for about 2 weeks. In this aspect of the embodiment, Form B and Form D were added to neat 1-propanol until saturated, the resulting suspension was agitated for about two weeks at ambient temperature, and the solids were vacuum filtered and analyzed by XRD to determine the resulting form as Form E. In another embodiment, a process to make Form E involved Form A and Form B co-incubated in 1-propanol for about 2 weeks. In this aspect of the embodiment, Form A and Form B were added to neat 1-propanol until saturated, the resulting suspension was agitated for about two weeks at ambient temperature, and the solids were vacuum filtered and analyzed by XRD to determine the resulting form as Form E. In another embodiment of the invention, Form E is used in a pharmaceutical product used to treat disease. Some of these embodiments encompass the use of Form E in a pharmaceutical product used for the treatment of cancer. In some of these embodiments, the cancer is cancer of the prostate, breast, skin, or other organ, as is known by the skilled artisan. Some of these embodiments encompass the use of Form E in a pharmaceutical product used for the treatment of a viral infection. In some of these embodiments, the viral infection is severe acute respiratory syndrome coronavirus 2 (SARS-CoV-2) or influenza. Some of these embodiments encompass the use of Form E in a pharmaceutical product used for the treatment of an inflammatory disease. In some of these embodiments, the inflammatory disease affects the lungs. In other of these embodiments, the inflammatory disease is an infection. In some embodiments, the inflammatory disease has caused acute respiratory distress syndrome (ARDS).

Figure 30:
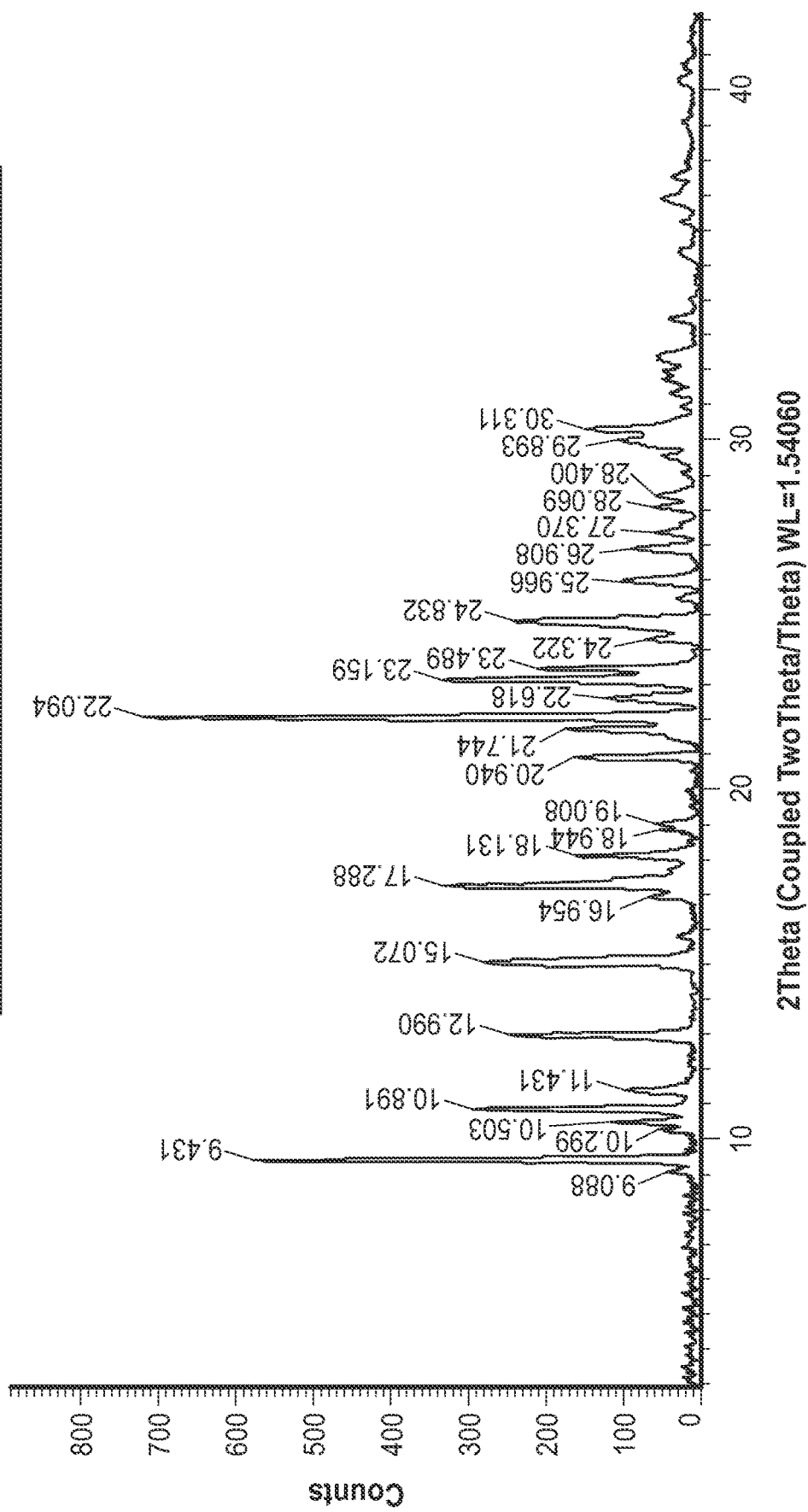
FIG. 30 illustrates the XRD pattern of the polymorphic Form E1 of the [2-(1H-indol-3-yl)-1H-imidazol-4-yl](3,4,5-trimethoxyphenyl)methanone hydrochloride salt which was made as the result of multiple processes described in Examples 3-5 (Form E1).

Another embodiment of the invention is directed to a crystalline polymorph Form E1 of the [2-(1H-indol-3-yl)-1H-imidazol-4-yl](3,4,5-trimethoxyphenyl)methanone hydrochloride salt characterized by an XRD pattern substantially as depicted in FIG. 30. In one aspect of this embodiment, Form E1 was characterized by an XRD pattern having peaks at about 9.4, 10.9, 17.3, 22.1, and 23.2 2θ±0.2 2θ. In another aspect of this embodiment, Form E1 was characterized by an XRD pattern having peaks at about 13.0, 15.1, 18.1, 20.9, and 24.8 2θ±0.2 2θ. The two diffraction patterns of Form E and Form E1 appear to be very similar except for minor differences between the two patterns in the 10-12° 2θ region.

One embodiment is directed to the preparation of Form E1. In one aspect of this embodiment, Form E1 was made by recrystallization from 2-propanol/dichloromethane or 2-propanol/trichloromethane. In one aspect of this embodiment, Form E1 was made by recrystallization of the [2-(1H-indol-3-yl)-1H-imidazol-4-yl](3,4,5-trimethoxyphenyl)methanone hydrochloride salt that was added to 2-propanol/dichloromethane binary solvent mixture at saturating concentrations at 25° C., heated to 45-50° C. to dissolve solids, and fast evaporated under 1.5 psi of $N_2$ flow at 40° C. to produce solid Form E1. In another aspect of this embodiment, Form E1 was made by recrystallization of the [2-(1H-indol-3-yl)-1H-imidazol-4-yl](3,4,5-trimethoxyphenyl) methanone hydrochloride salt that was added to 2-propanol/trichloromethane binary solvent mixture at saturating concentrations at 25° C., heated to 45-50° C. to dissolve solids, and fast evaporated under 1.5 psi of $N_2$ flow at 40° C. to produce solid Form E1.

One embodiment is directed to the preparation of Form E1. In one aspect of this embodiment, a process to make Form E1 involved non-competitive slurry of Form B in any one of five binary solvent mixtures including ethanol/toluene, acetonitrile (ACN)/acetone, ethanol/acetonitrile, 1-propanol/ethyl acetate (EtOAc) or 2-propanol/tetrahydrofuran (THF) for 11 days. In these embodiments, to avoid possible desolvation or physical change after isolation, the samples were not further dried before X-ray analysis. In this embodiment, a process to make Form E1 involved non-competitive slurry of Form B in the non-aqueous binary solvent system of ethanol/toluene for 11 days. In this embodiment, excess Form B was added to ethanol/toluene mixture until saturated, the resulting suspension was agitated for eleven days at ambient temperature, and the solids were vacuum filtered and analyzed by XRD to determine the resulting form as Form E1. In another embodiment, a process to make Form E1 involved non-competitive slurry of Form B in the non-aqueous binary solvent system of acetonitrile (ACN)/acetone for 11 days. In this embodiment, excess Form B was added to an acetonitrile (ACN)/acetone mixture until saturated, the resulting suspension was agitated for eleven days at ambient temperature, and the solids were vacuum filtered and analyzed by XRD to determine the resulting form as Form E1. In another embodiment, a process to make Form E1 involved non-competitive slurry of Form B in a non-aqueous binary solvent system of ethanol/acetonitrile for 11 days. In this embodiment, excess Form B was added to an ethanol/acetonitrile mixture until saturated, the resulting suspension was agitated for eleven days at ambient temperature, and the solids were vacuum filtered and analyzed by XRD to determine the resulting form as Form E1. In another embodiment, a process to make Form E1 involved non-competitive slurry of Form B in the non-aqueous binary solvent system of 1-propanol/ethyl acetate (EtOAc) for 11 days. In this embodiment, excess Form B was added to a 1-propanol/ethyl acetate (EtOAc) mixture until saturated, the resulting suspension was agitated for eleven days at ambient temperature, and the solids were vacuum filtered and analyzed by XRD to determine the resulting form as Form E1. In another embodiment, a process to make Form E1 involved non-competitive slurry of Form B in the non-aqueous binary solvent system of 2-propanol/tetrahydrofuran (THF) for 11 days. In this embodiment, excess Form B was added to a 2-propanol/tetrahydrofuran (THF) mixture until saturated, the resulting suspension was agitated for eleven days at ambient temperature, and the solids were vacuum filtered and analyzed by XRD to determine the resulting form as Form E1.

In one embodiment, Form E1 is prepared by any one of four competitive slurry experiments in which binary combinations of Form A, Form B, Form $C_H$, Form D, and Form E were slurried in 1-propanol for about two weeks. In these embodiments, to avoid possible desolvation or physical change after isolation, the samples were not further dried before X-ray analysis. In one embodiment, a process to make Form E1 involved Form $C_H$ and Form B co-incubated in 1-propanol for about 2 weeks. In this embodiment, Form $C_H$ and Form B were added to neat 1-propanol until saturated, the resulting suspension was agitated for about two weeks at ambient temperature, and the solids were vacuum filtered and analyzed by XRD to determine the resulting form as Form E1. In another embodiment, a process to make Form E1 involved Form A and Form D co-incubated in 1-propanol for about 2 weeks. In this embodiment, Form A and Form D were added to neat 1-propanol until saturated, the resulting suspension was agitated for about two weeks at ambient temperature, and the solids were vacuum filtered and analyzed by XRD to determine the resulting form as Form E1. In another embodiment, a process to make Form E1 involved Form B and Form E co-incubated in 1-propanol for about 2 weeks. In this embodiment, Form B and Form E were added to neat 1-propanol until saturated, the resulting suspension was agitated for about two weeks at ambient temperature, and the solids were vacuum filtered and analyzed by XRD to determine the resulting form as Form E1. In another embodiment, a process to make Form E1 involved Form D and Form E co-incubated in 1-propanol for about 2 weeks. In this embodiment, Form D and Form E were added to neat 1-propanol until saturated, the resulting suspension was agitated for about two weeks at ambient temperature, and the solids were vacuum filtered and analyzed by XRD to determine the resulting form as Form E1. In another embodiment of the invention, Form E1 is used in a pharmaceutical product used to treat disease. Some of these embodiments encompass the use of Form E1 in a pharmaceutical product used for the treatment of cancer. In some of these embodiments, the cancer is cancer of the prostate, breast, skin, or other organ, as is known by the skilled artisan. Some of these embodiments encompass the use of Form E1 in a pharmaceutical product used for the treatment of a viral infection. In some of these embodiments, the viral infection is severe acute respiratory syndrome coronavirus 2 (SARS-CoV-2) or influenza. Some of these embodiments encompass the use of Form E1 in a pharmaceutical product used for the treatment of an inflammatory disease. In some of these embodiments, the inflammatory disease affects the lungs. In other of these embodiments, the inflammatory disease is an infection. In some embodiments, the inflammatory disease has caused acute respiratory distress syndrome (ARDS).

Figure 38:
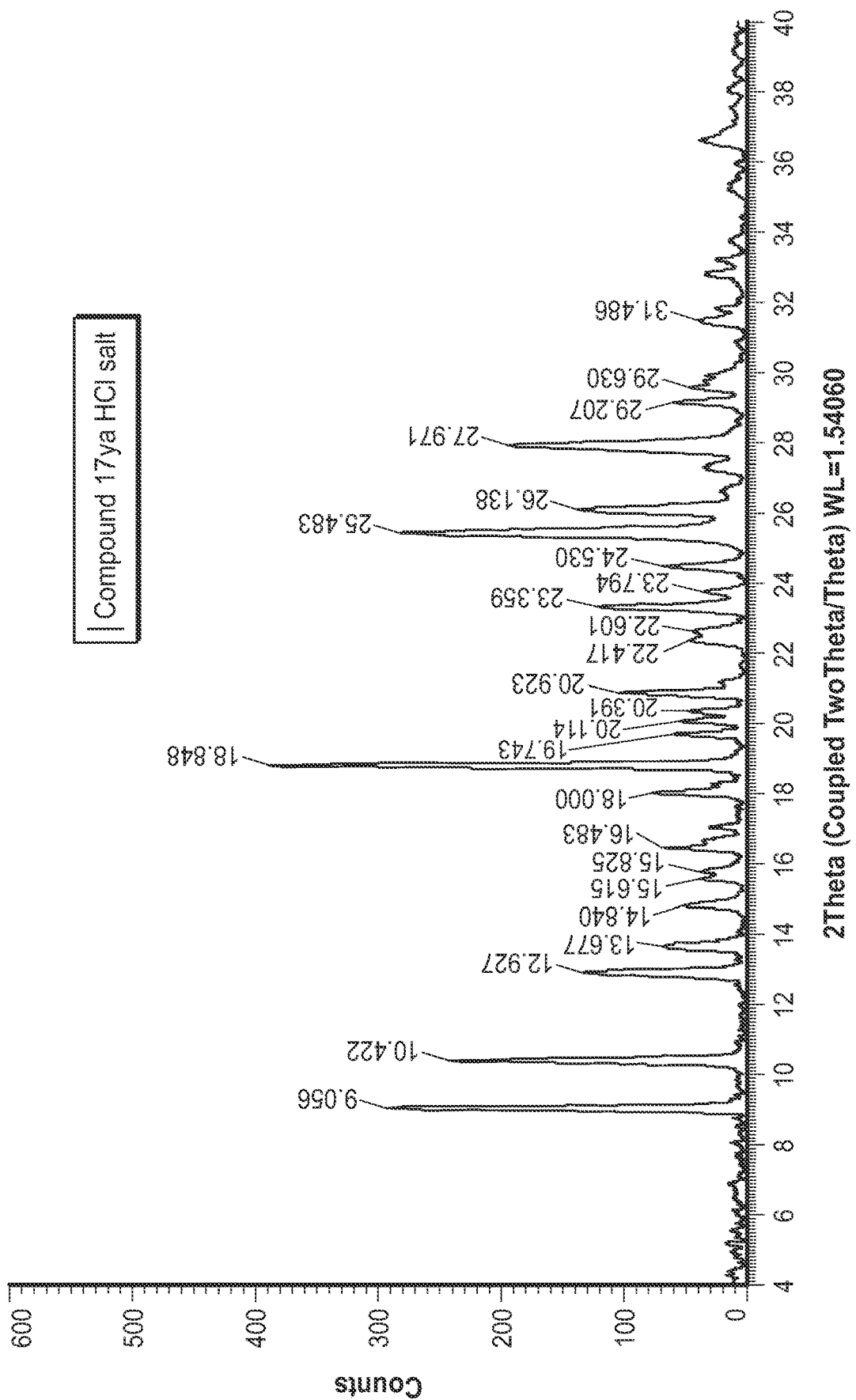
FIG. 38 illustrates the XRD pattern of the polymorphic Form $F_H$ of the [2-(1H-indol-3-yl)-1H-imidazol-4-yl](3,4,5-trimethoxyphenyl)methanone hydrochloride salt prepared according to Example 6 (Form $F_H$).
Figure 39:
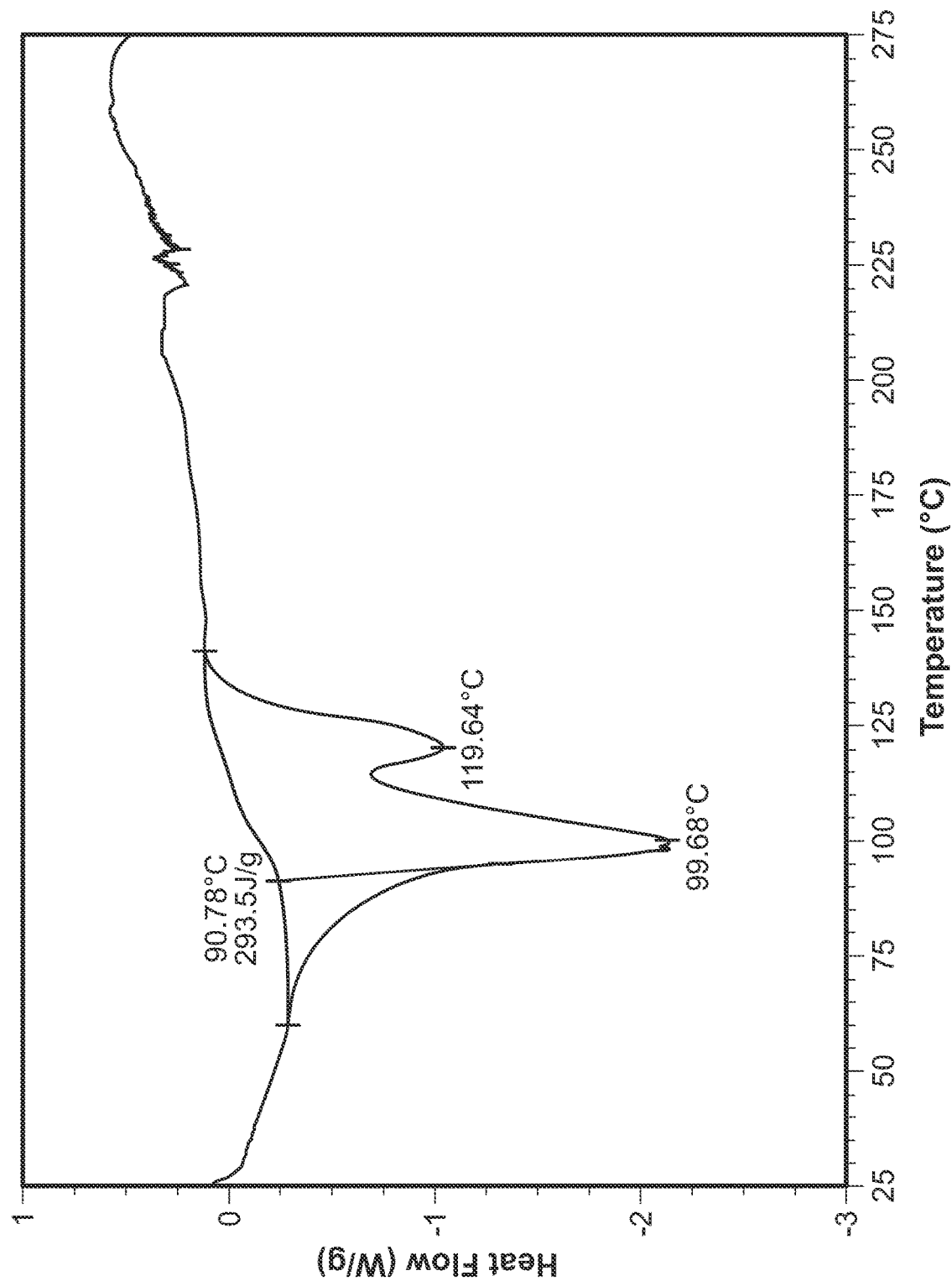
FIG. 39 illustrates the DSC thermogram of Form $F_H$ that exhibited large split endotherm with an onset of approximately 90.8° C. and peak maxima of 99.7° C. and 119.6° C. The Karl Fischer (KF) moisture content was 14% by weight.

Another embodiment of the invention is directed to a crystalline polymorph Form $F_H$ of the [2-(1H-indol-3-yl)-1H-imidazol-4-yl](3,4,5-trimethoxyphenyl)methanone hydrochloride salt characterized by an XRD pattern substantially as depicted in FIG. 38. In one aspect of this embodiment, Form $F_H$ was characterized by an XRD pattern having peaks at about 9.06, 10.4, 18.85, 25.48, and 27.97 2θ±0.2 2θ. In another aspect of this embodiment, Form $F_H$ was characterized by an XRD pattern having peaks at about 12.9, 20.9, and 26.14 2θ±0.2 2θ. One embodiment is directed to the preparation of Form $F_H$ from Form E or Form E1 stored at ambient conditions. In another embodiment of the invention, Form $F_H$ is used in a pharmaceutical product used to treat disease. Some of these embodiments encompass the use of Form $F_H$ in a pharmaceutical product used for the treatment of cancer. In some of these embodiments, the cancer is cancer of the prostate, breast, skin, or other organ, as is known by the skilled artisan. Some of these embodiments encompass the use of Form $F_H$ in a pharmaceutical product used for the treatment of a viral infection. In some of these embodiments, the viral infection is severe acute respiratory syndrome coronavirus 2 (SARS-CoV-2) or influenza. Some of these embodiments encompass the use of Form $F_H$ in a pharmaceutical product used for the treatment of an inflammatory disease. In some of these embodiments, the inflammatory disease affects the lungs. In other of these embodiments, the inflammatory disease is an infection. In some embodiments, the inflammatory disease has caused acute respiratory distress syndrome (ARDS).

Figure 40:
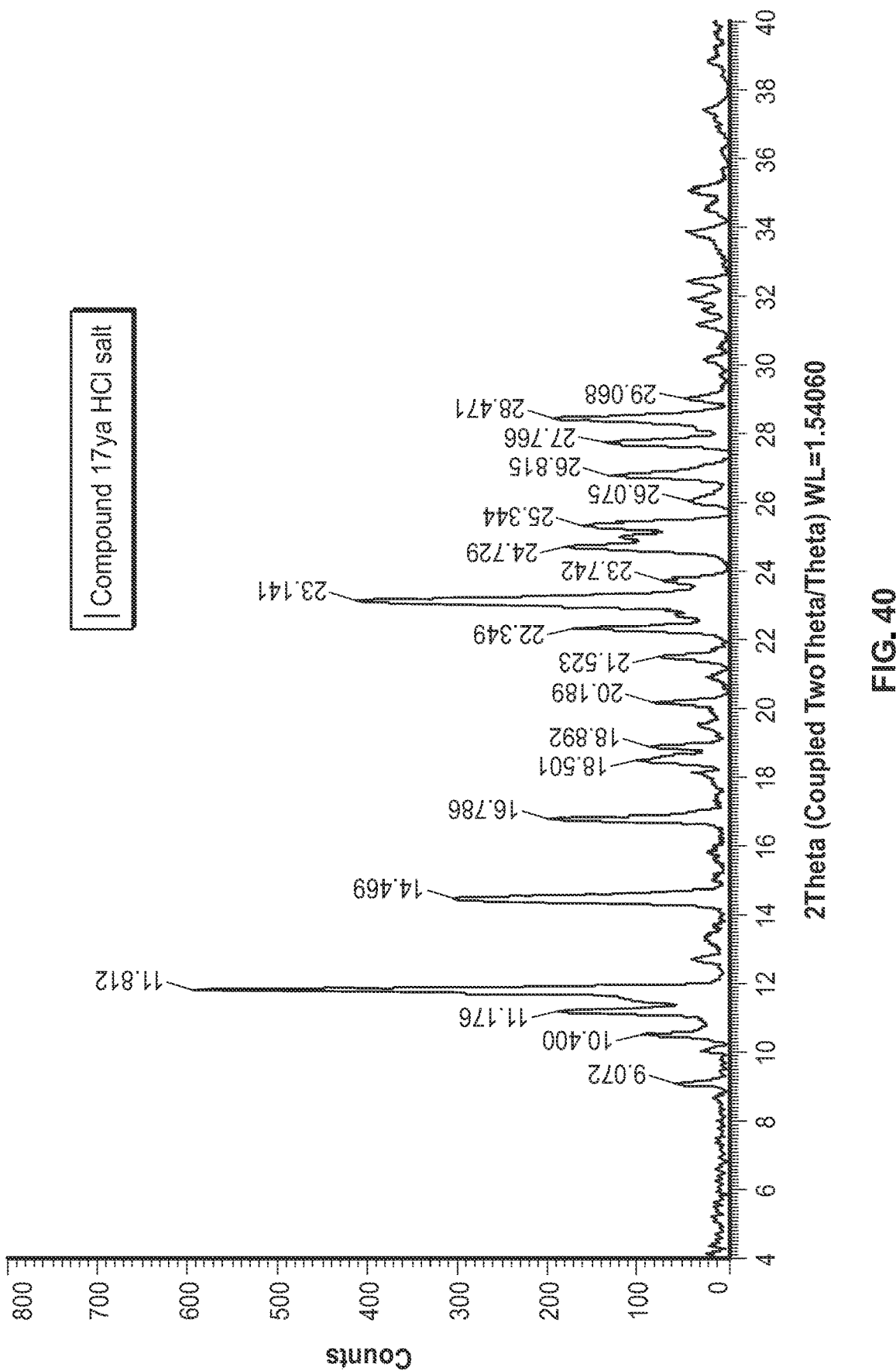
FIG. 40 illustrates the XRD pattern of the polymorphic Form $G_H$ of the [2-(1H-indol-3-yl)-1H-imidazol-4-yl](3,4,5-trimethoxyphenyl)methanone hydrochloride salt prepared according to Example 6 (Form $G_H$).

Another embodiment of the invention is directed to a crystalline polymorph Form $G_H$ of the [2-(1H-indol-3-yl)-1H-imidazol-4-yl](3,4,5-trimethoxyphenyl)methanone hydrochloride salt characterized by an XRD pattern substantially as depicted in FIG. 40. In one aspect of this embodiment, Form $G_H$ was characterized by an XRD pattern having peaks at about 11.8, 14.5, 16.8, 23.1, and 28.5 2θ±0.2 2θ. In another aspect of this embodiment, Form $G_H$ was characterized by an XRD pattern having peaks at about 10.4, 22.3, 24.7, and 25.3 2θ±0.2 2θ. One embodiment is directed to the preparation of Form $G_H$ from Form E or Form E1 stored at ambient conditions. In another embodiment of the invention, Form $G_H$ is used in a pharmaceutical product used to treat disease. Some of these embodiments encompass the use of Form $G_H$ in a pharmaceutical product used for the treatment of cancer. In some of these embodiments, the cancer is cancer of the prostate, breast, skin, or other organ, as is known by the skilled artisan. Some of these embodiments encompass the use of Form $G_H$ in a pharmaceutical product used for the treatment of a viral infection. In some of these embodiments, the viral infection is severe acute respiratory syndrome coronavirus 2 (SARS-CoV-2) or influenza. Some of these embodiments encompass the use of Form G$_H$ in a pharmaceutical product used for the treatment of an inflammatory disease. In some of these embodiments, the inflammatory disease affects the lungs. In other of these embodiments, the inflammatory disease is an infection. In some embodiments, the inflammatory disease has caused acute respiratory distress syndrome (ARDS).

Figure 43:
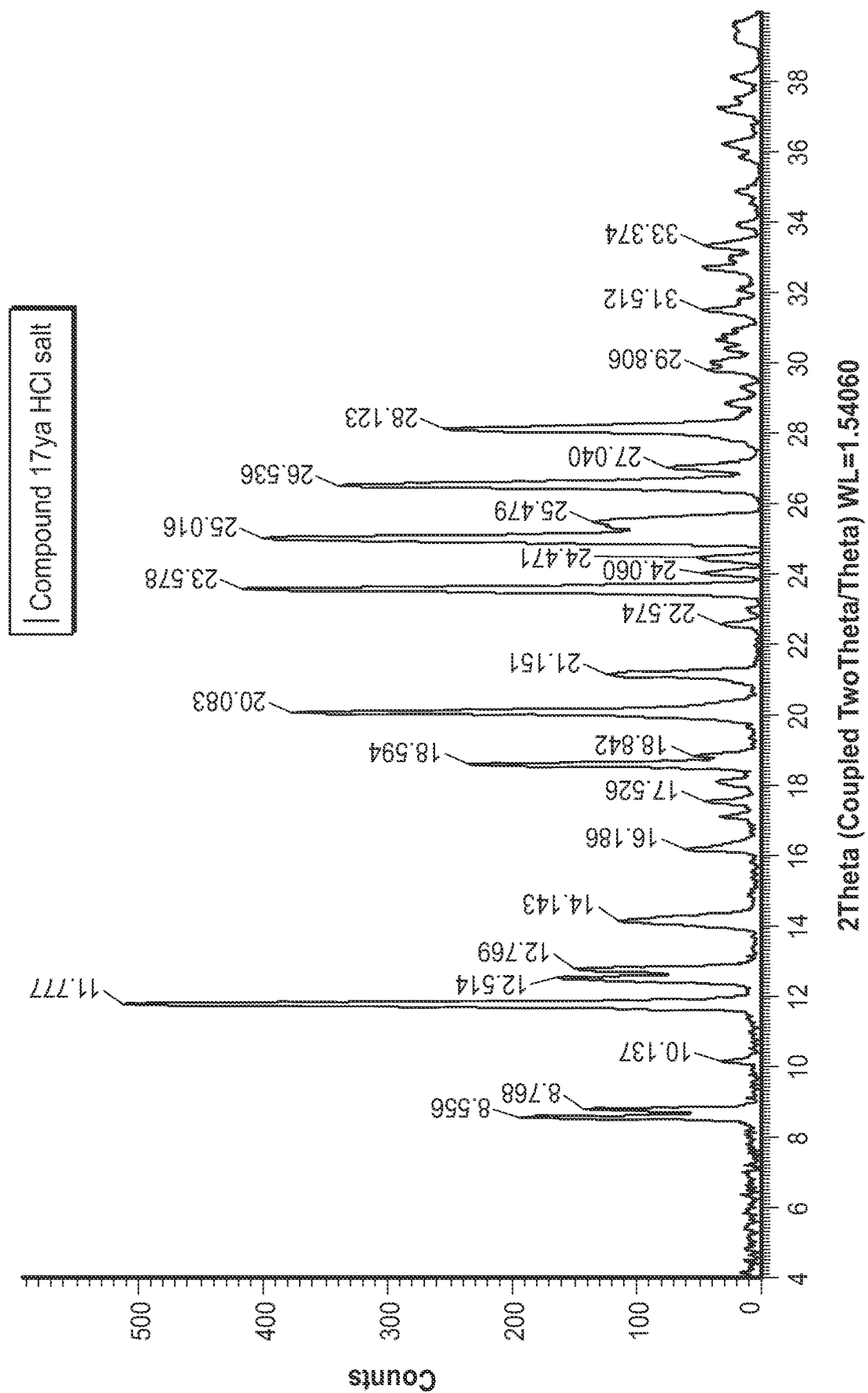
FIG. 43 illustrates the XRD pattern of the polymorphic Form H of the [2-(1H-indol-3-yl)-1H-imidazol-4-yl](3,4,5-trimethoxyphenyl)methanone hydrochloride salt prepared according to Examples 5 and 6 (Form H).

Another embodiment of the invention is directed to a crystalline polymorph Form H of the [2-(1H-indol-3-yl)-1H-imidazol-4-yl](3,4,5-trimethoxyphenyl)methanone hydrochloride salt characterized by an XRD pattern substantially as depicted in FIG. 43. In one aspect of this embodiment, Form H was characterized by an XRD pattern having peaks at about 11.8, 20.1, 23.6, 25.0, and 26.5 2θ±0.2 2θ. In another aspect of this embodiment, Form H was characterized by an XRD pattern having peaks at about 8.6, 12.5, 18.6, 21.2, and 28.1 2θ±0.2 2θ. One embodiment is directed to the preparation of Form H from Form E stored at ambient conditions. Another embodiment is directed to the preparation of Form H from Form E1 stored at ambient conditions. Another embodiment is directed to the preparation of Form H from any polymorphic form of the [2-(1H-indol-3-yl)-1H-imidazol-4-yl](3,4,5-trimethoxyphenyl)methanone hydrochloride salt stored at ambient conditions. In one embodiment, the conversion of Form E, Form E1 or any other polymorphic form of he [2-(1H-indol-3-yl)-1H-imidazol-4-yl](3,4,5-trimethoxyphenyl)methanone hydrochloride salt occurs at ambient conditions in the absence of any Form H seeding crystals.

In one embodiment, Form H is prepared by one of two competitive slurry experiments in which Form E and Form H were slurried in 2-butanol or 2-propanol for 1 day. In these embodiments, to avoid possible desolvation or physical change after isolation, the samples were not further dried before X-ray analysis. In one embodiment, a process to make Form H involved Form E and Form H co-incubated in 2-butanol for 1 day. In this embodiment, Form E and Form H were added to neat 2-butanol until saturated, the resulting suspension was agitated for 1 day at ambient temperature, and the solids were vacuum filtered and analyzed by XRD to determine the resulting form as Form H. In another embodiment, a process to make Form H involved Form E and Form H co-incubated in 2-propanol for 1 day. In this embodiment, Form E and Form H were added to neat 2-propanol until saturated, the resulting suspension was agitated for 1 day at ambient temperature, and the solids were vacuum filtered and analyzed by XRD to determine the resulting form as Form H. In one embodiment, a process to make substantially pure Form H involved the synthesis of the [2-(1H-indol-3-yl)-1H-imidazol-4-yl](3,4,5-trimethoxyphenyl)methanone hydrochloride salt from Intermediate C-5 in the presence of minute quantities of Form H (Example 7). In another embodiment, a process to make substantially pure Form H involved the conversion of Form E to Form H in the presence of minute quantities Form H seed crystals. In some embodiments, kilogram scale quantities of Form H can be made from crude [2-(1H-indol-3-yl)-1H-imidazol-4-yl](3,4,5-trimethoxyphenyl)methanone hydrochloride salt in any polymorphic form in the presence of gram quantities of Form H seed crystals. In some embodiments, the Form H seed crystals are added to crude [2-(1H-indol-3-yl)-1H-imidazol-4-yl](3,4,5-trimethoxyphenyl)methanone hydrochloride salt slurried in ethanol and ethyl acetate.

In another embodiment of the invention, Form H is used in a pharmaceutical product used to treat disease. Some of these embodiments encompass the use of Form H in a pharmaceutical product used for the treatment of cancer. In some of these embodiments, the cancer is cancer of the prostate, breast, skin, or other organ, as is known by the skilled artisan. Some of these embodiments encompass the use of Form H in a pharmaceutical product used for the treatment of a viral infection. In some of these embodiments, the viral infection is severe acute respiratory syndrome coronavirus 2 (SARS-CoV-2)I or influenza. Some of these embodiments encompass the use of Form H in a pharmaceutical product used for the treatment of an inflammatory disease. In some of these embodiments, the inflammatory disease affects the lungs. In other of these embodiments, the inflammatory disease is an infection. In some embodiments, the inflammatory disease has caused acute respiratory distress syndrome (ARDS).

Figure 46:
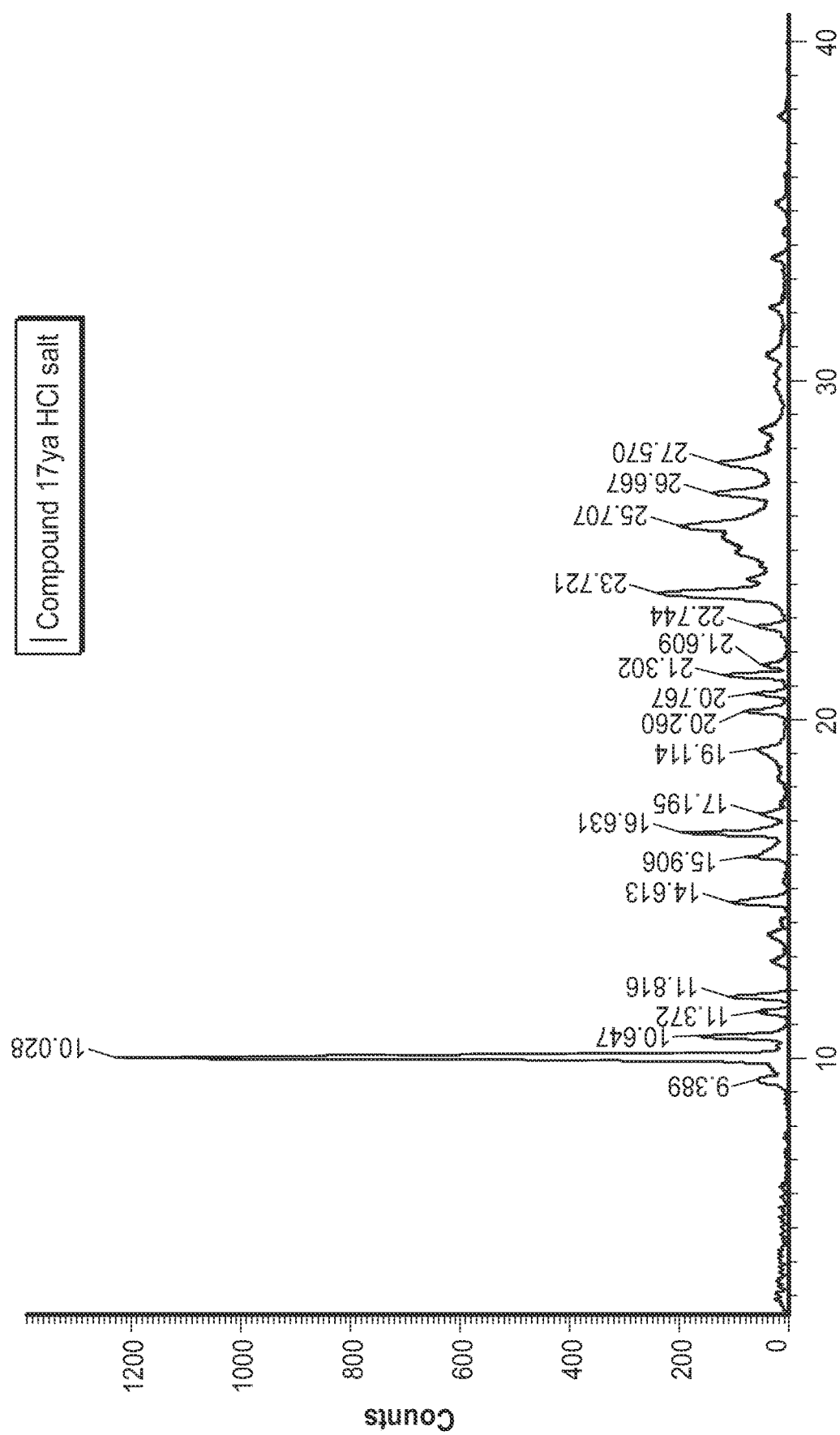
FIG. 46 illustrates the XRD diffraction pattern of the polymorphic Form I of the [2-(1H-indol-3-yl)-1H-imidazol-4-yl](3,4,5-trimethoxyphenyl)methanone hydrochloride salt prepared according to Example 6 (Form I).

Another embodiment of the invention is directed to a crystalline polymorph Form I of the [2-(1H-indol-3-yl)-1H-imidazol-4-yl](3,4,5-trimethoxyphenyl)methanone hydrochloride salt characterized by an XRD pattern substantially as depicted in FIG. 46. In one aspect of this embodiment, Form I of the HCl salt was characterized by an XRD pattern having peaks at about 10.0, 10.6, 16.6, 23.7, and 25.7 2θ±0.2 2θ. In another aspect of this embodiment, Form I of the HCl salt was characterized by an XRD pattern having peaks at about 11.8, 15.9, 26.7, and 27.6 2θ±0.2 2θ. In another embodiment of the invention, Form I of the HCl salt is used in a pharmaceutical product used to treat disease. Some of these embodiments encompass the use of Form I of the HCl salt in a pharmaceutical product used for the treatment of cancer. In some of these embodiments, the cancer is cancer of the prostate, breast, skin, or other organ, as is known by the skilled artisan. Some of these embodiments encompass the use of Form I of the HCl salt in a pharmaceutical product used for the treatment of a viral infection. In some of these embodiments, the viral infection is severe acute respiratory syndrome coronavirus 2 (SARS-CoV-2)I or influenza. Some of these embodiments encompass the use of Form I of the HCl salt in a pharmaceutical product used for the treatment of an inflammatory disease. In some of these embodiments, the inflammatory disease affects the lungs. In other of these embodiments, the inflammatory disease is an infection. In some embodiments, the inflammatory disease has caused acute respiratory distress syndrome (ARDS).

Figure 15:
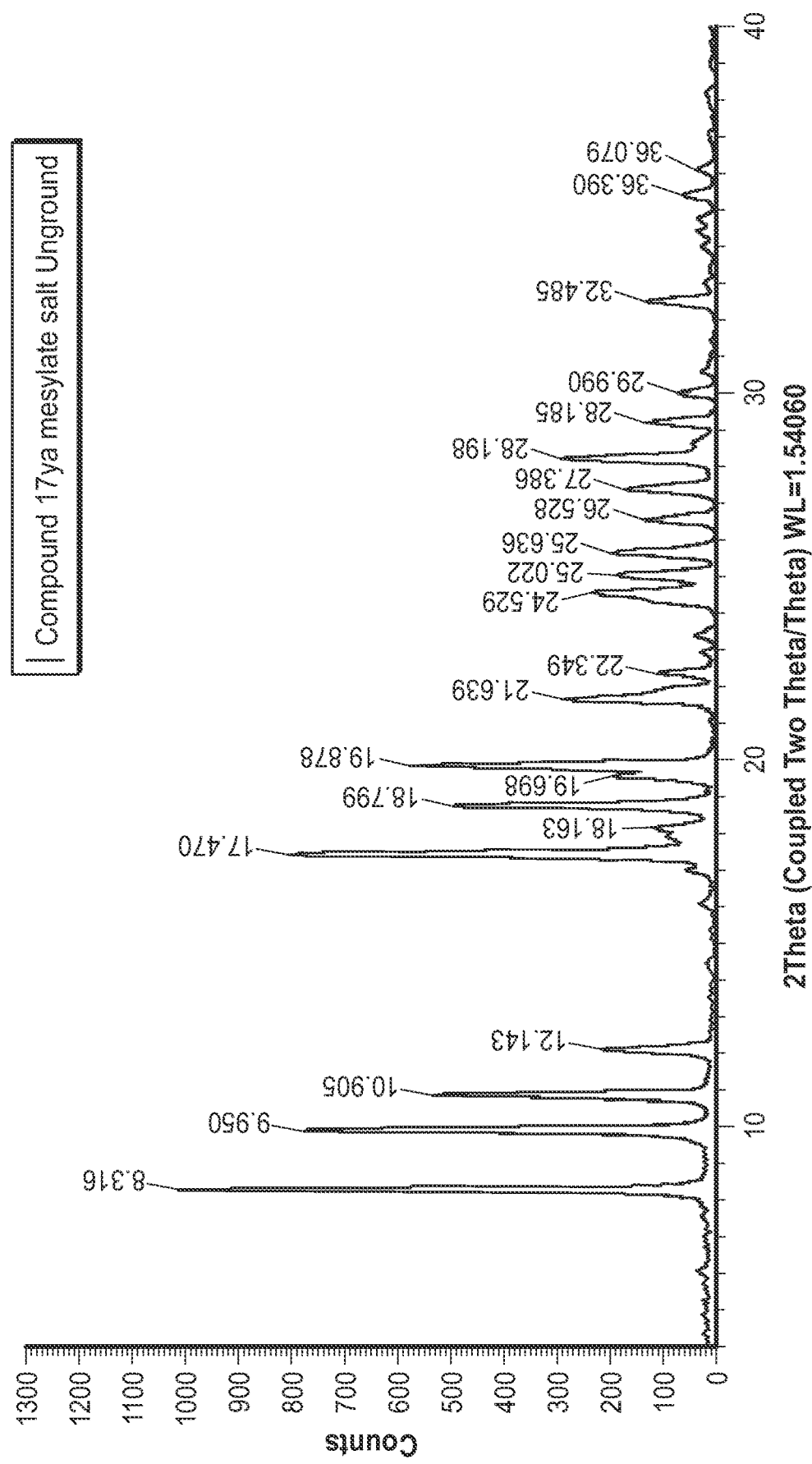
FIG. 15 illustrates the XRD pattern of the [2-(1H-indol-3-yl)-1H-imidazol-4-yl](3,4,5-trimethoxyphenyl)methanone mesylate salt produced by the processes of Examples 1 or 2 that exhibited a crystalline solid.

One embodiment of this invention is directed to the mesylate salt of [2-(1H-indol-3-yl)-1H-imidazol-4-yl](3,4,5-trimethoxyphenyl)methanone. Another embodiment of this invention is directed to a polymorph of the mesylate salt of [2-(1H-indol-3-yl)-1H-imidazol-4-yl](3,4,5-trimethoxyphenyl)methanone, as characterized herein. In one embodiment, the crystalline polymorph of the [2-(1H-indol-3-yl)-1H-imidazol-4-yl](3,4,5-trimethoxyphenyl)methanone mesylate salt is characterized by an XRD pattern substantially as depicted in FIG. 15. In one aspect of this embodiment, the crystalline polymorph of the mesylate salt was characterized by an XRD pattern having peaks at about 8.3, 9.9, 10.9, 17.5, and 19.9 2θ±0.2 2θ. In another aspect of this embodiment, the crystalline polymorph of the mesylate salt was characterized by an XRD pattern having peaks at about 12.1, 18.8, 21.9, 24.5, and 28.2 2θ±0.2 2θ.

Figure 12:
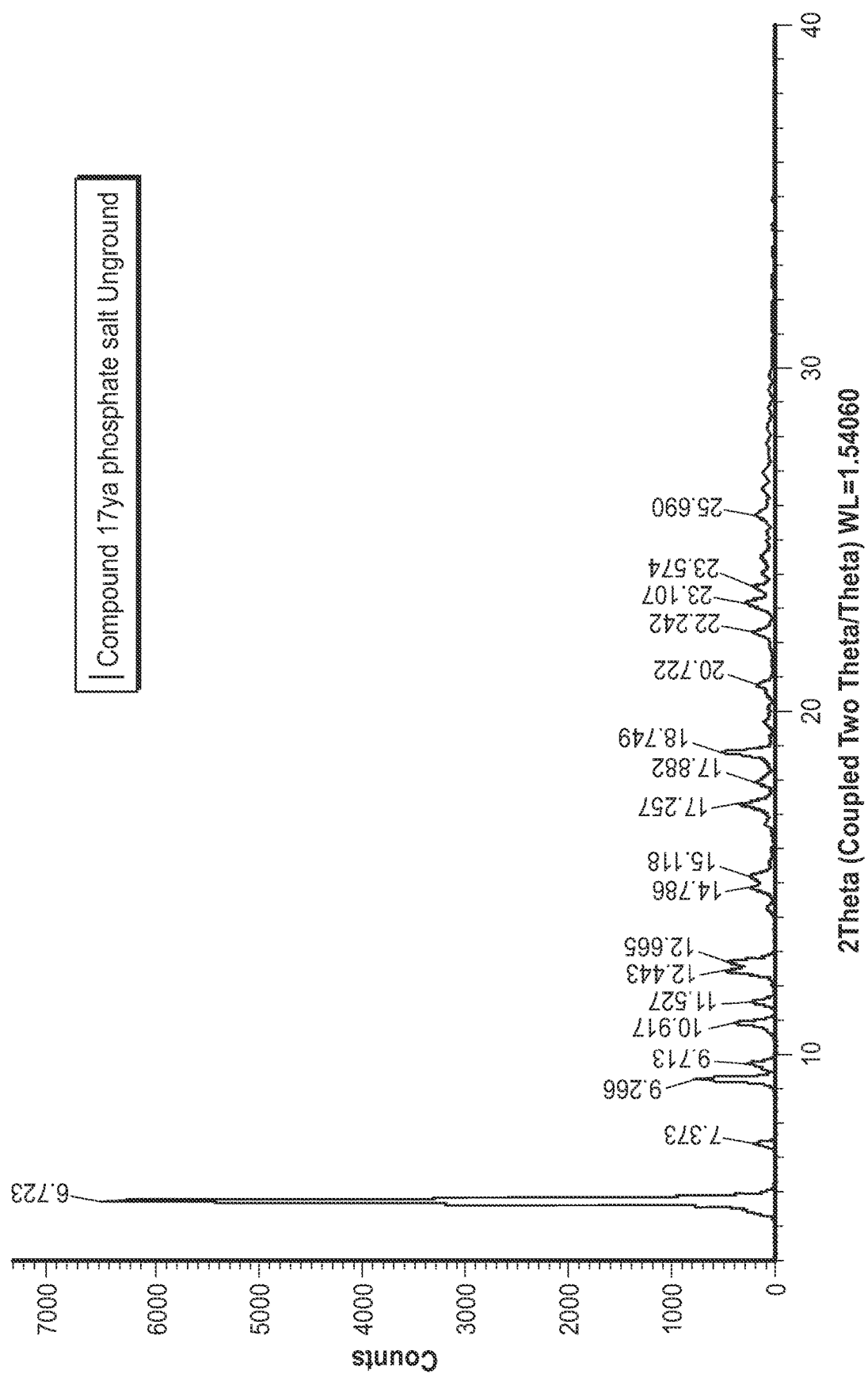
FIG. 12 illustrates the XRD pattern of the [2-(1H-indol-3-yl)-1H-imidazol-4-yl](3,4,5-trimethoxyphenyl)methanone phosphate salt produced by the processes of Examples 1 or 2 where the crystallinity indicated a preferred grain orientation.

One embodiment of this invention is directed to the phosphate salt of [2-(1H-indol-3-yl)-1H-imidazol-4-yl](3,4,5-trimethoxyphenyl)methanone. Another embodiment of this invention is directed to a polymorph of the phosphate salt of [2-(1H-indol-3-yl)-1H-imidazol-4-yl](3,4,5-trimethoxyphenyl)methanone, as characterized herein. In one embodiment, the crystalline polymorph of the [2-(1H-indol-3-yl)-1H-imidazol-4-yl](3,4,5-trimethoxyphenyl) methanone phosphate salt is characterized by an XRD pattern substantially as depicted in FIG. 12. In one aspect of this embodiment, the crystalline polymorph of the phosphate salt was characterized by an XRD pattern having peaks at about 5.7, 9.3, 12.4, 12.6, and 18.8 2θ±0.2 2θ. In another aspect of this embodiment, the crystalline polymorph of the phosphate salt was characterized by an XRD pattern having peaks at about 9.7, 10.9, 11.6, and 20.7 2θ±0.2 2θ.

Figure 9:
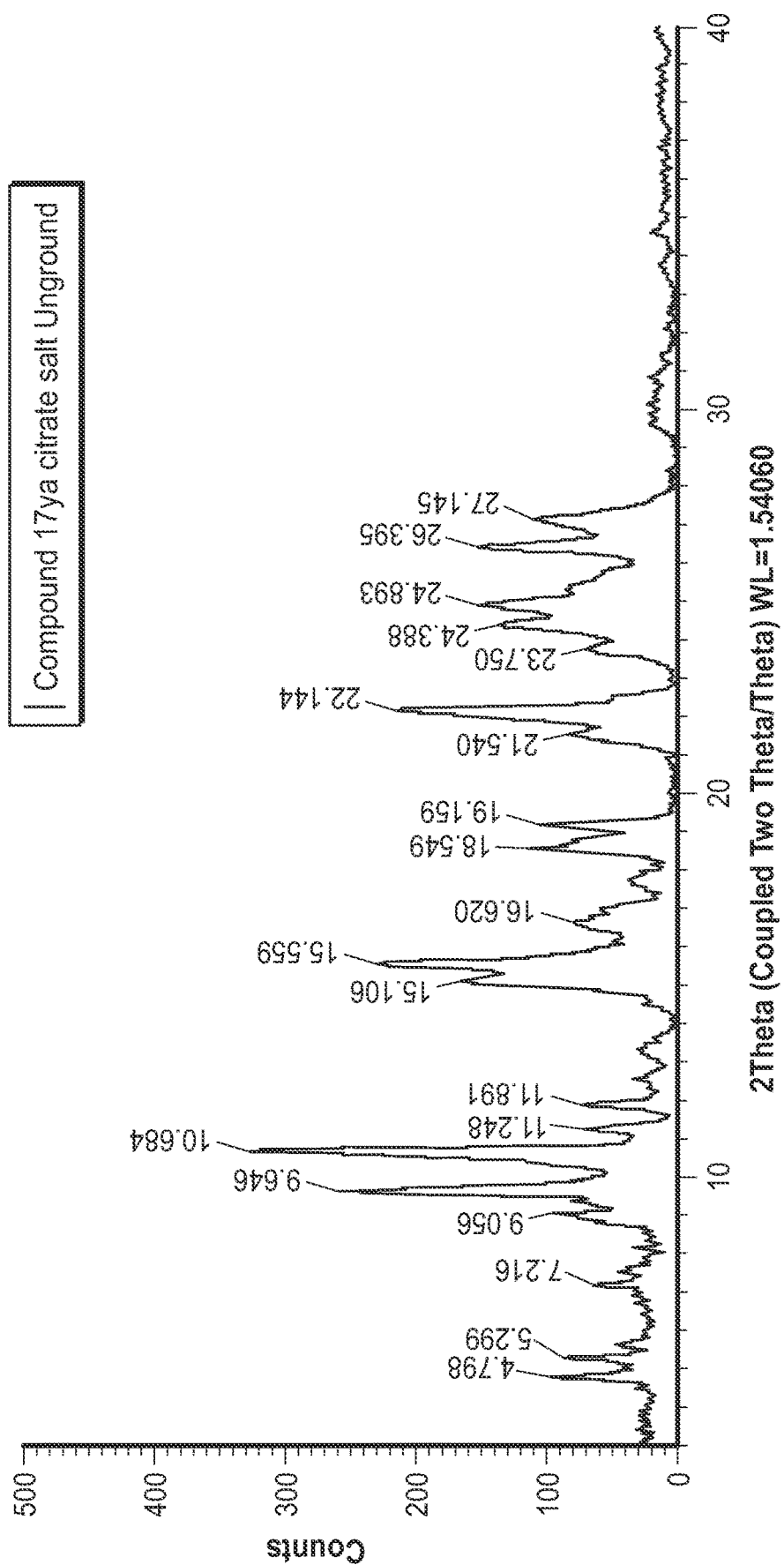
FIG. 9 illustrates the XRD pattern of the [2-(1H-indol-3-yl)-1H-imidazol-4-yl](3,4,5-trimethoxyphenyl)methanone citrate salt produced by the processes of Examples 1 or 2 that indicated a lowly ordered crystalline solid.

One embodiment of this invention is directed to the citrate salt of [2-(1H-indol-3-yl)-1H-imidazol-4-yl](3,4,5-trimethoxyphenyl)methanone. Another embodiment of this invention is directed to a polymorph of the citrate salt of [2-(1H-indol-3-yl)-1H-imidazol-4-yl](3,4,5-trimethoxyphenyl)methanone, as characterized herein. In one embodiment, the crystalline polymorph of the [2-(1H-indol-3-yl)-1H-imidazol-4-yl](3,4,5-trimethoxyphenyl)methanone citrate salt is characterized by an XRD pattern substantially as depicted in FIG. 9. In one aspect of this embodiment, the crystalline polymorph of the citrate salt was characterized by an XRD pattern having peaks at about 9.7, 10.7, 15.1, 15.6, and 22.1 2θ±0.2 2θ. In another aspect of this embodiment, the crystalline polymorph of the citrate salt was characterized by an XRD pattern having peaks at about 18.6, 19.2, 26.4, and 27.1 2θ±0.2 2θ.

Since hydrochloric acid (HCl) is a Class I salt forming acid, the [2-(1H-indol-3-yl)-1H-imidazol-4-yl](3,4,5-trimethoxyphenyl)methanone hydrochloride salt was synthesized to provide a Class I salt with lower safety risk relative to other salt forms. Class I salts possess unrestricted use because they form physiologically ubiquitous ions or they occur as intermediate metabolites in biochemical pathways. The [2-(1H-indol-3-yl)-1H-imidazol-4-yl](3,4,5-trimethoxyphenyl)methanone hydrochloride salt formed in Example 2 was crystalline, polymorphic, and had good solubility in unbuffered water (less than 1 mg/mL). This unnamed polymorph of the hydrochloride salt also showed evidence of possible hydrate formation at approximately 30-40% RH (relative humidity), in particular, at about 50% RH.

Figure 6:
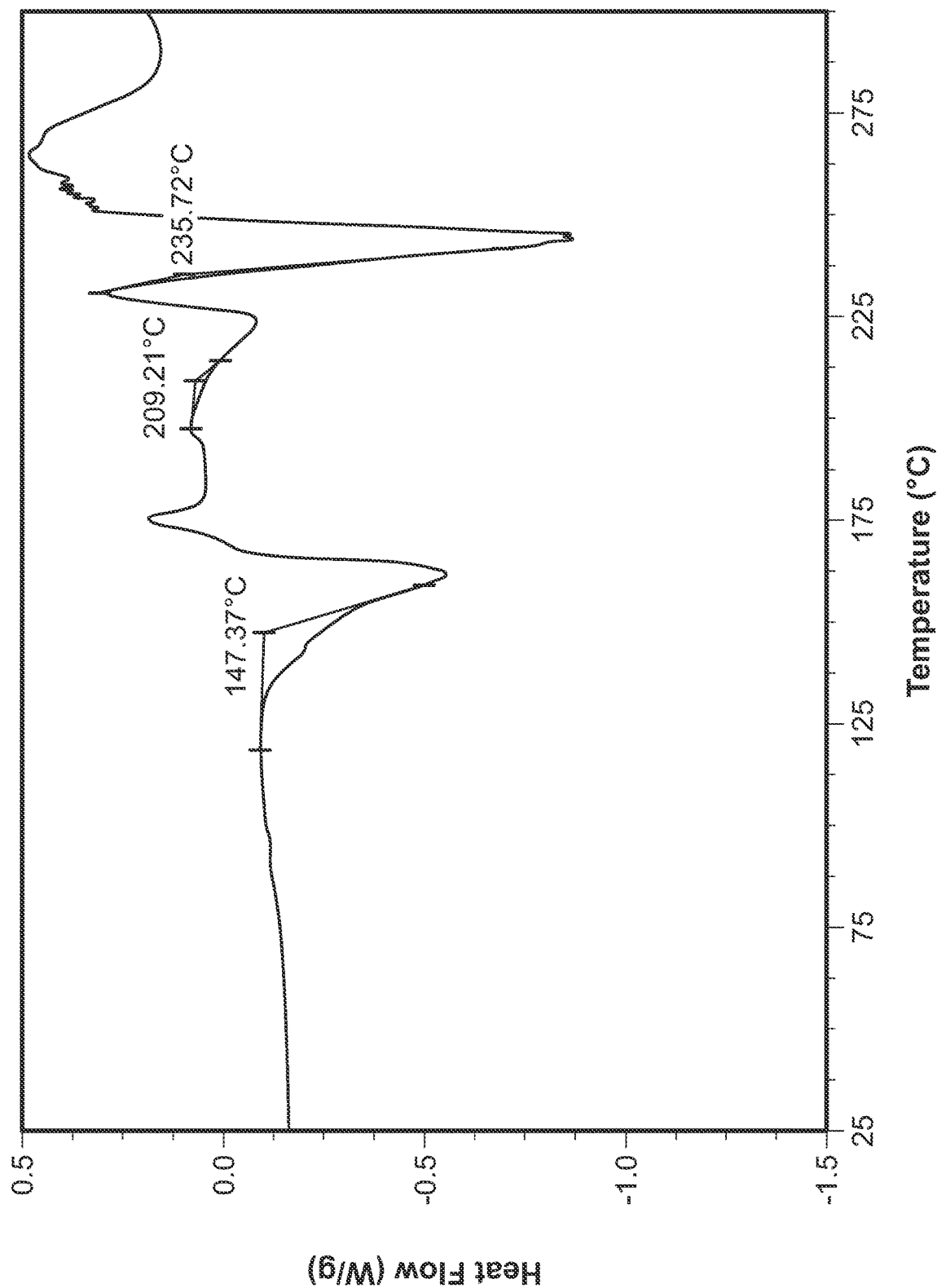
FIG. 6 illustrates the DSC profile of the unnamed crystalline form produced by the processes of Examples 1 or 2 of the [2-(1H-indol-3-yl)-1H-imidazol-4-yl](3,4,5-trimethoxyphenyl)methanone hydrochloride salt that exhibited multiple thermal events prior to the eventual melting onset endotherm at approximately 211.9° C.
Figure 7:
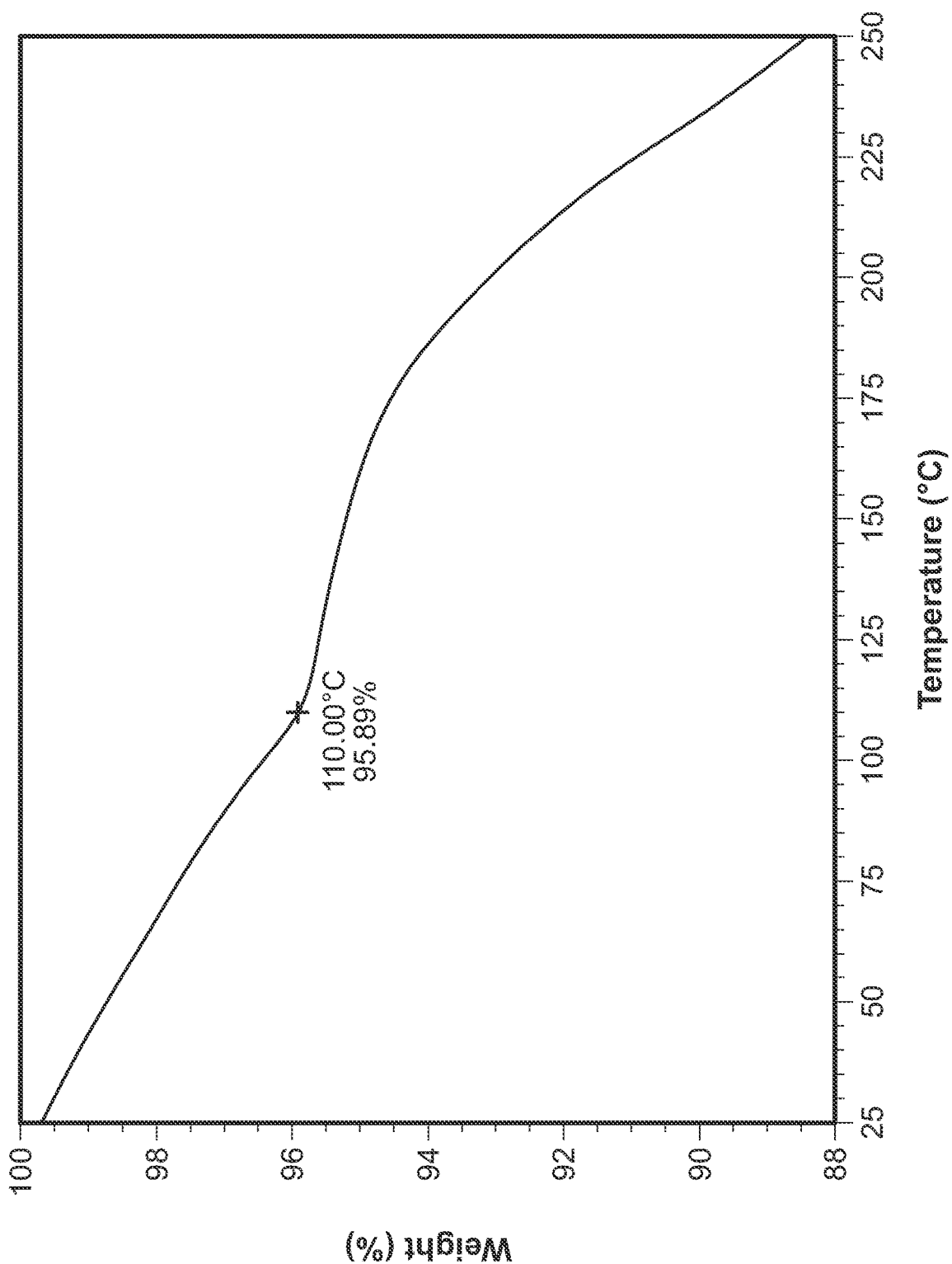
FIG. 7 illustrates the TGA profile of the unnamed crystalline form produced by the processes of Examples 1 or 2 of the [2-(1H-indol-3-yl)-1H-imidazol-4-yl](3,4,5-trimethoxyphenyl)methanone hydrochloride salt that showed a continuous loss in weight with a weight loss of about 0.54% to 4.1% from 25° C. to 110° C.
Figure 8A:
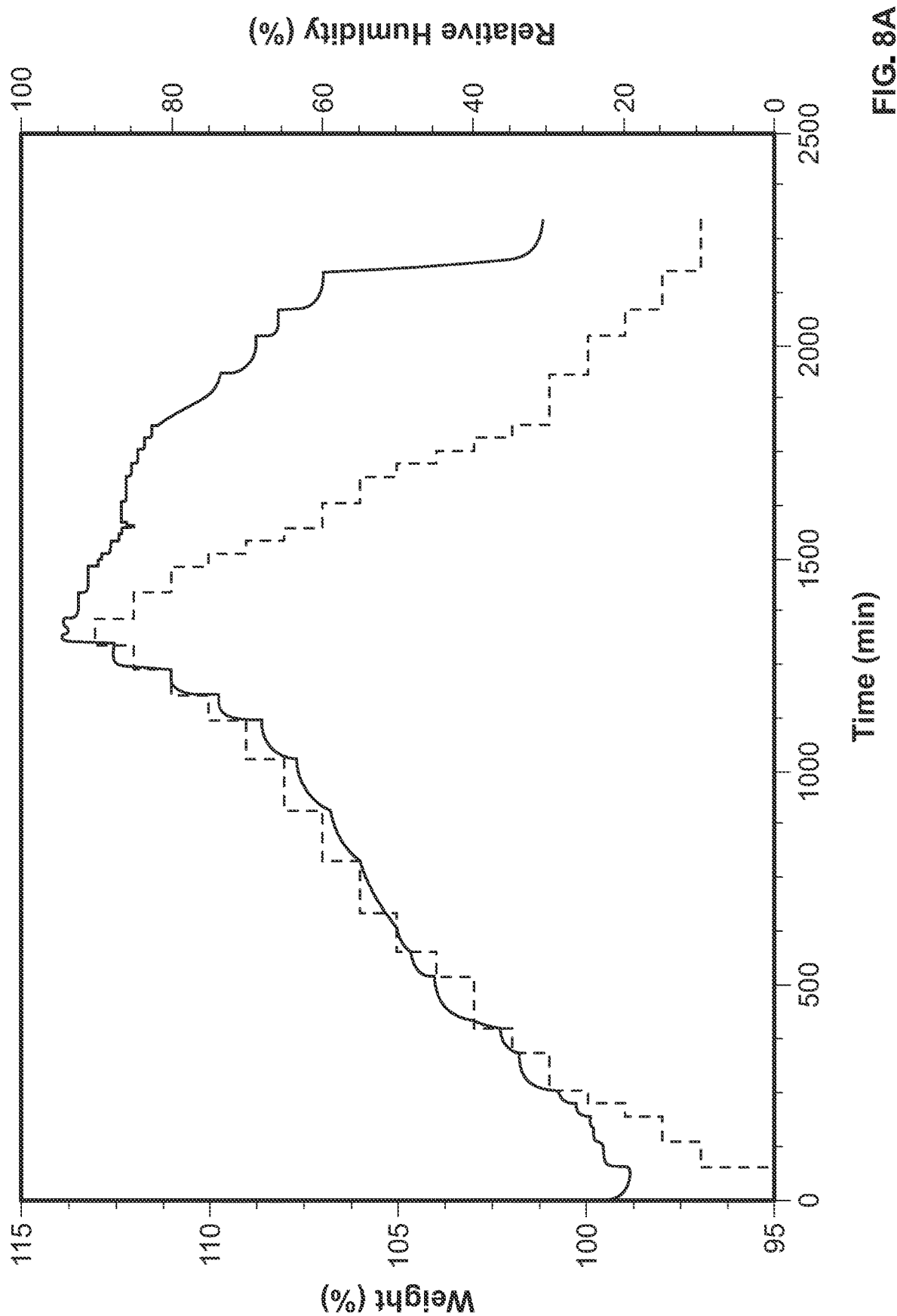
FIG. 8A illustrates the dynamic vapor sorption (DVS) data of the unnamed crystalline form produced by the processes of Examples 1 or 2 of the [2-(1H-indol-3-yl)-1H-imidazol-4-yl](3,4,5-trimethoxyphenyl)methanone hydrochloride salt that exhibited non-stoichiometric uptake of water as hydrates in a complex that may form above 30-40% relative humidity (RH).
Figure 8B:
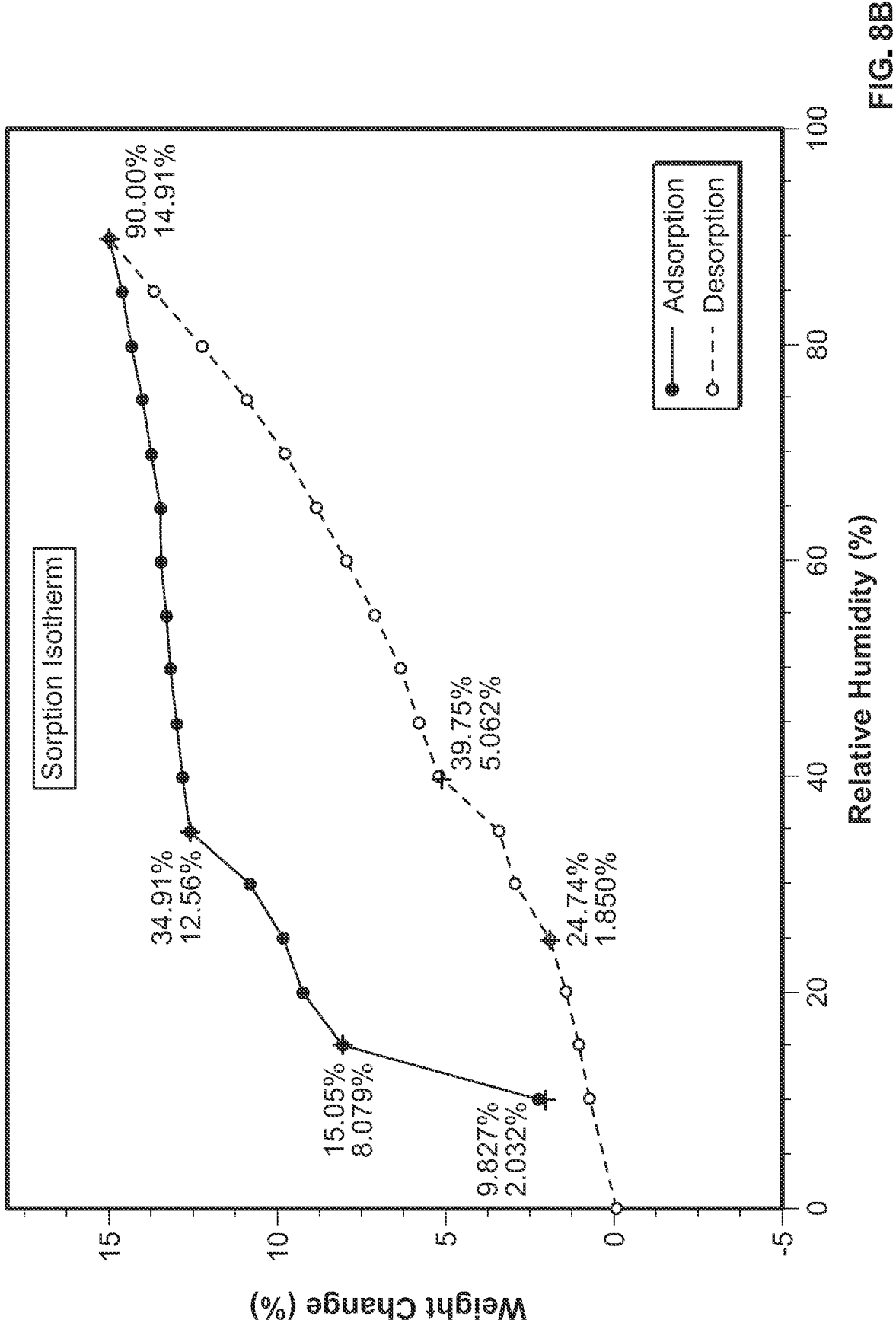
FIG. 8B illustrates a DVS with a top line for adsorption and a lower line for desorption.

The XRD pattern of the [2-(1H-indol-3-yl)-1H-imidazol-4-yl](3,4,5-trimethoxyphenyl)methanone hydrochloride salt formed in Example 2 indicated the compound was crystalline, as illustrated in FIG. 5. This unnamed crystalline polymorph does not appear to correlate with any of the other polymorphic forms of the [2-(1H-indol-3-yl)-1H-imidazol-4-yl](3,4,5-trimethoxyphenyl)methanone hydrochloride salt characterized herein, to include Forms A, B, $C_H$, D, E, E1, $F_H$, $G_H$, H, and I. The crystalline polymorph of the [2-(1H-indol-3-yl)-1H-imidazol-4-yl](3,4,5-trimethoxyphenyl) methanone hydrochloride salt formed in Example 2 was characterized by an XRD pattern having peaks at about 10.8, 13.3, 21.5, 23.1, and 35.2 2θ±0.2 2θ. The crystalline polymorph of the [2-(1H-indol-3-yl)-1H-imidazol-4-yl](3,4,5-trimethoxyphenyl)methanone hydrochloride salt formed in Example 2 was further characterized by an XRD pattern having peaks at 10.5, 14.1, 16.1, and 26.2 2θ±0.2 2θ. The DSC profile exhibited multiple thermal events prior to the eventual melting onset endotherm at approximately 235.7° C., as illustrated in FIG. 6. The TGA profile showed a continuous loss in weight with a weight loss of about 0.54% to 4.1% from 25° C. to 110° C., as illustrated in FIG. 7. Hygroscopicity was determined with dynamic vapor sorption (DVS). The DVS data exhibited non-stoichiometric uptake of water as hydrates may form above 30-40% RH in a complex and a total adsorption of water of approximately 8.8 wt % to 14.9 wt % at 90% RH, as illustrated in FIG. 8.

Figure 10:
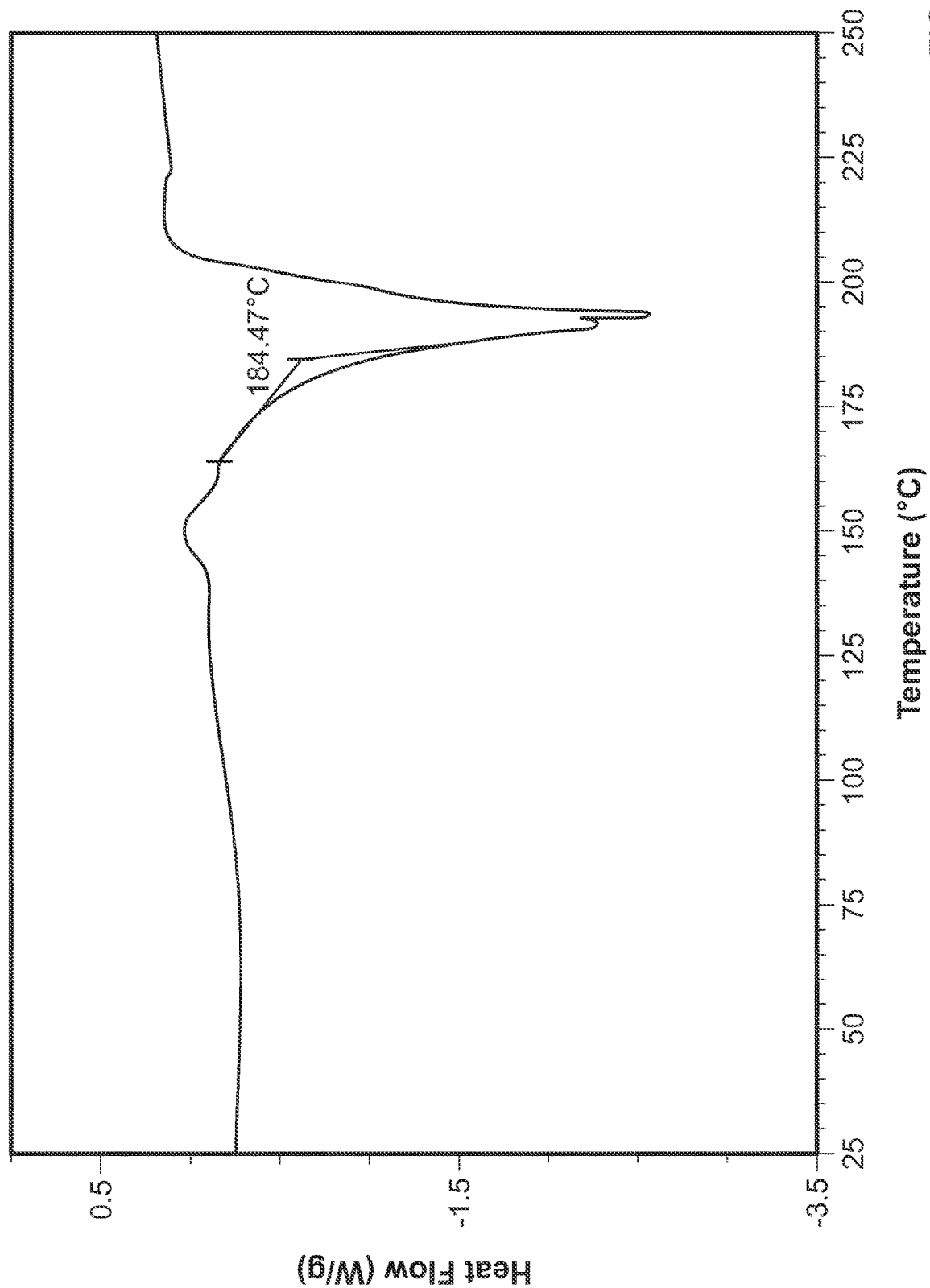
FIG. 10 illustrates the DSC profile of the [2-(1H-indol-3-yl)-1H-imidazol-4-yl](3,4,5-trimethoxyphenyl)methanone citrate salt of Examples 1 or 2 that exhibited a small exothermic transition at approximately 130° C. immediately followed by a broad melting onset endotherm at approximately 184.5° C.
Figure 11:
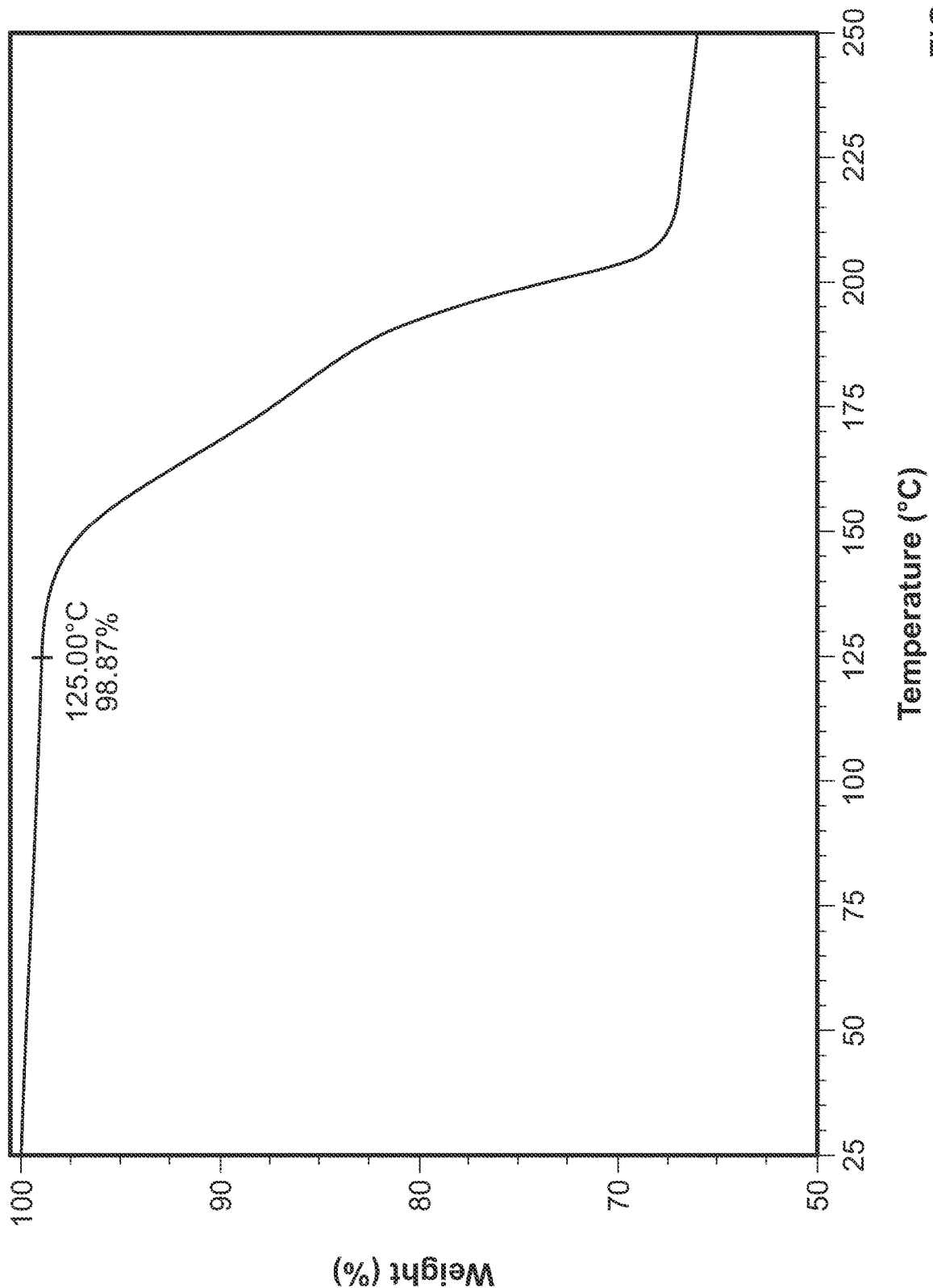
FIG. 11 illustrates the TGA profile of the [2-(1H-indol-3-yl)-1H-imidazol-4-yl](3,4,5-trimethoxyphenyl)methanone citrate salt of Examples 1 or 2 that showed a weight loss of about 0.38% to 1.13% from 25° C. to 125° C. followed by decomposition.

The [2-(1H-indol-3-yl)-1H-imidazol-4-yl](3,4,5-trimethoxyphenyl)methanone citrate salt had moderate crystallinity and had good solubility in unbuffered water (approximately 1 mg/mL). The [2-(1H-indol-3-yl)-1H-imidazol-4-yl](3,4,5-trimethoxyphenyl)methanone citrate salt was polymorphic and showed evidence of possible dihydrate formation at approximately 30-40% RH, and in particular at 60% RH (data not shown). The XRD pattern of the small scale citrate salt (synthesized according to Example 1) indicated a lowly ordered crystalline solid, as illustrated in FIG. 9. The crystalline [2-(1H-indol-3-yl)-1H-imidazol-4-yl](3,4,5-trimethoxyphenyl)methanone citrate salt was characterized by an XRD pattern having peaks at about 9.7, 10.7, 15.1, 15.6, and 22.1 2θ±0.2 2θ. The crystalline [2-(1H-indol-3-yl)-1H-imidazol-4-yl](3,4,5-trimethoxyphenyl)methanone citrate salt was further characterized by an XRD pattern having peaks at 18.6, 19.2, 26.4, and 27.1 2θ±0.2 2θ. The DSC profile exhibited a small exothermic transition at approximately 130° C. immediately followed by a broad melting onset endotherm at approximately 184.5° C., as illustrated in FIG. 10. The TGA profile showed a weight loss of about 0.38% to 1.13% from 25° C. to 125° C. followed by decomposition, which was graphically illustrated in FIG. 11.

Figure 13:
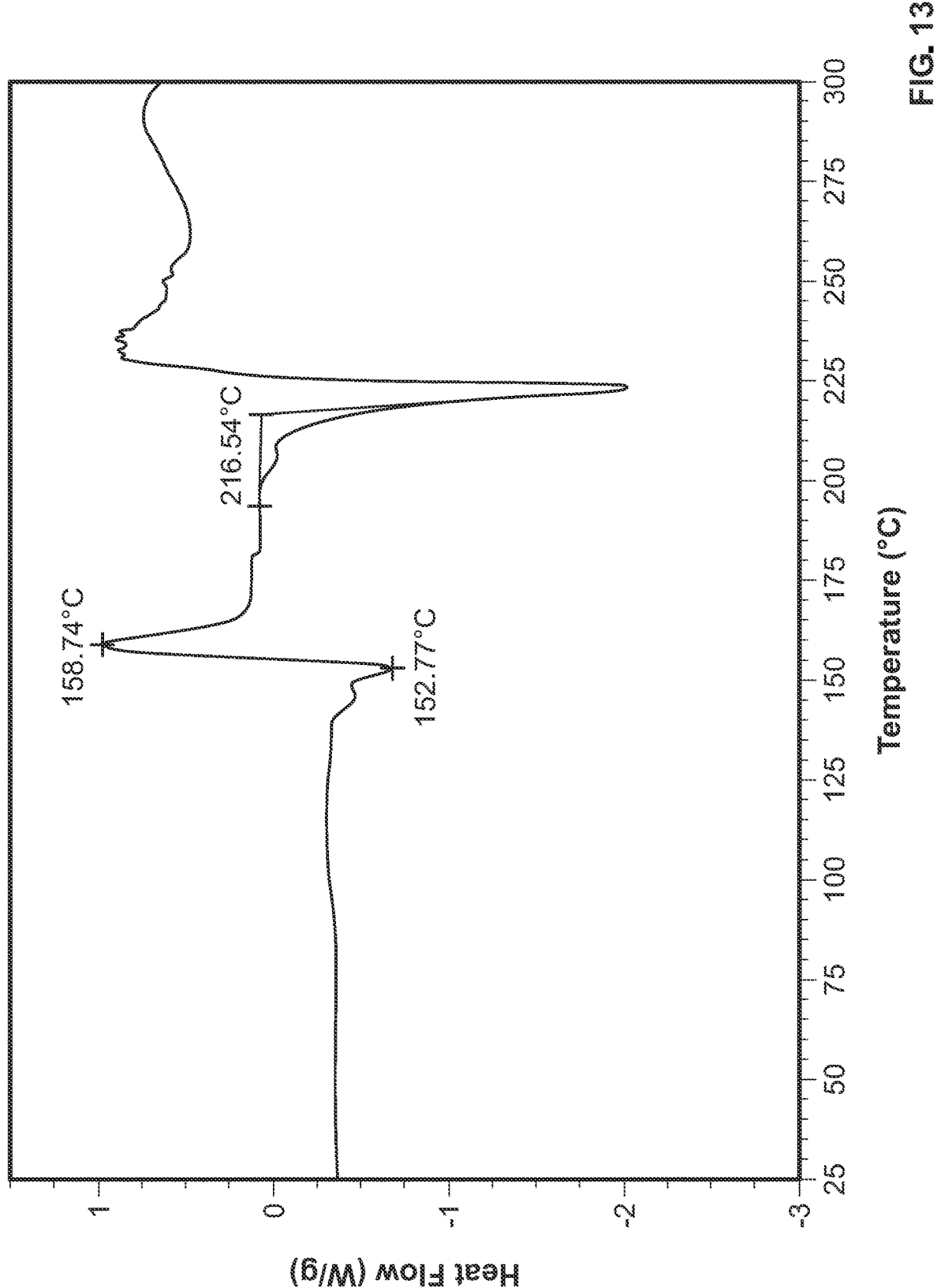
FIG. 13 illustrates the DSC profile of the [2-(1H-indol-3-yl)-1H-imidazol-4-yl](3,4,5-trimethoxyphenyl)methanone phosphate salt of Examples 1 or 2 that exhibited loss of volatiles at about 149° C. to 152° C. immediately followed by exothermic recrystallization at 158.7° C. and a melting onset endotherm at approximately 216° C. to 219° C., followed by decomposition.
Figure 14:
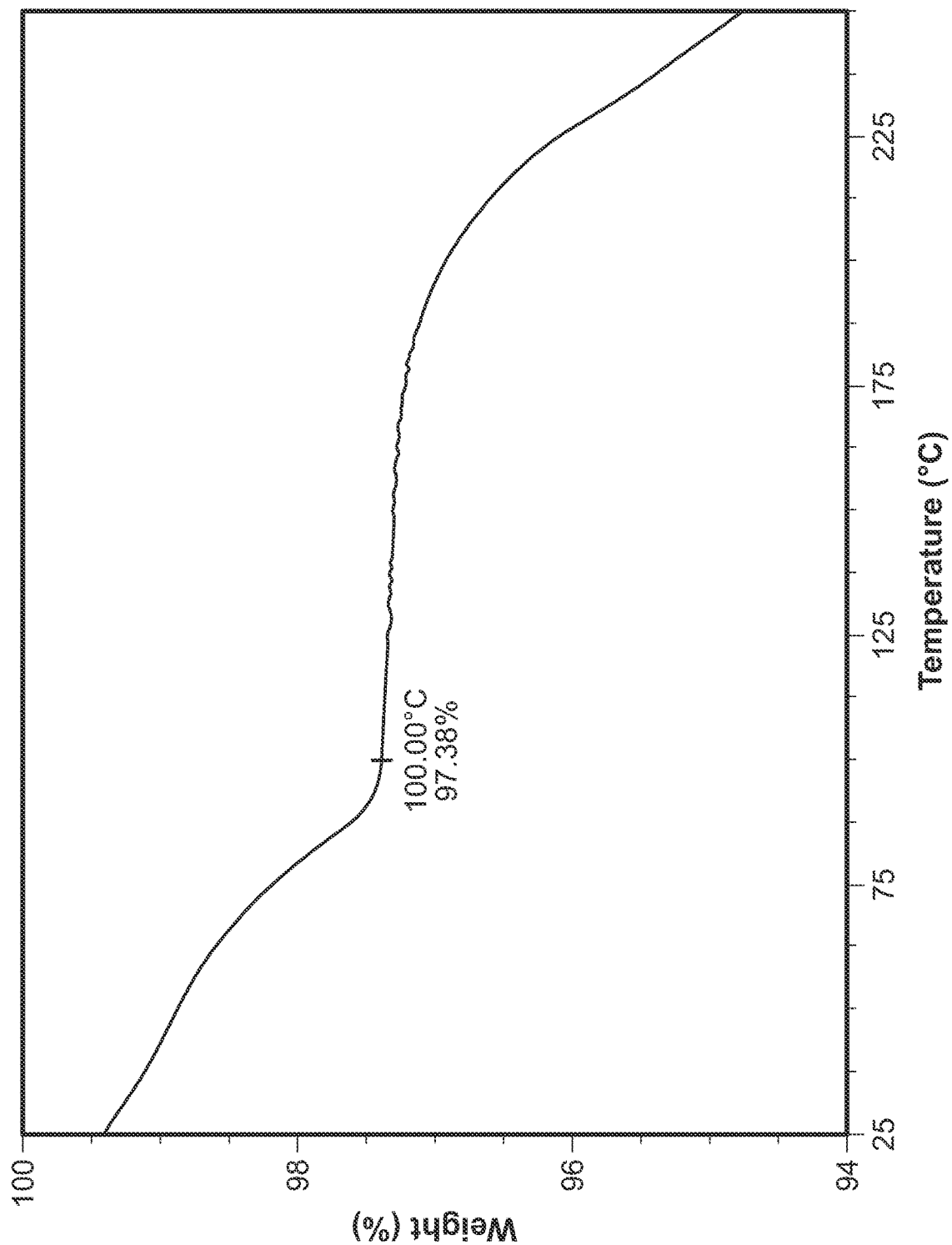
FIG. 14 illustrates the TGA profile of the [2-(1H-indol-3-yl)-1H-imidazol-4-yl](3,4,5-trimethoxyphenyl)methanone phosphate salt of Examples 1 or 2 that showed a continuous loss in weight with a weight loss of about 2.6% to 2.88% probably due to loss of volatiles from 25° C. to 100° C. followed by further decomposition.

The [2-(1H-indol-3-yl)-1H-imidazol-4-yl](3,4,5-trimethoxyphenyl)methanone phosphate salt synthesized according to Example 1 showed good crystallinity and good solubility in unbuffered water (less than 1 mg/mL). The XRD pattern of the [2-(1H-indol-3-yl)-1H-imidazol-4-yl](3,4,5-trimethoxyphenyl)methanone phosphate salt indicated crystallinity that exhibited preferred grain orientation, as illustrated in FIG. 12. The crystalline polymorph of the [2-(1H-indol-3-yl)-1H-imidazol-4-yl](3,4,5-trimethoxyphenyl)methanone phosphate salt was characterized by an XRD pattern having peaks at about 5.7, 9.3, 12.4, 12.6, and 18.8 2θ±0.2 2θ. The crystalline polymorph of the [2-(1H-indol-3-yl)-1H-imidazol-4-yl](3,4,5-trimethoxyphenyl)methanone phosphate salt was further characterized by an XRD pattern having peaks at 9.7, 10.9, 11.6, and 20.7 2θ±0.2 2θ. The DSC profile exhibited loss of volatiles at about 149° C. to 153° C. immediately followed by exothermic recrystallization at 158.7° C. and a melting onset endotherm at approximately 216° C. to 219° C., followed by decomposition, as illustrated in FIG. 13. The TGA profile showed a continuous loss in weight with a weight loss of about 2.6% to 2.88% probably due to loss of volatiles from 25° C. to 100° C. followed by further decomposition, as illustrated in FIG. 14.

Figure 16:
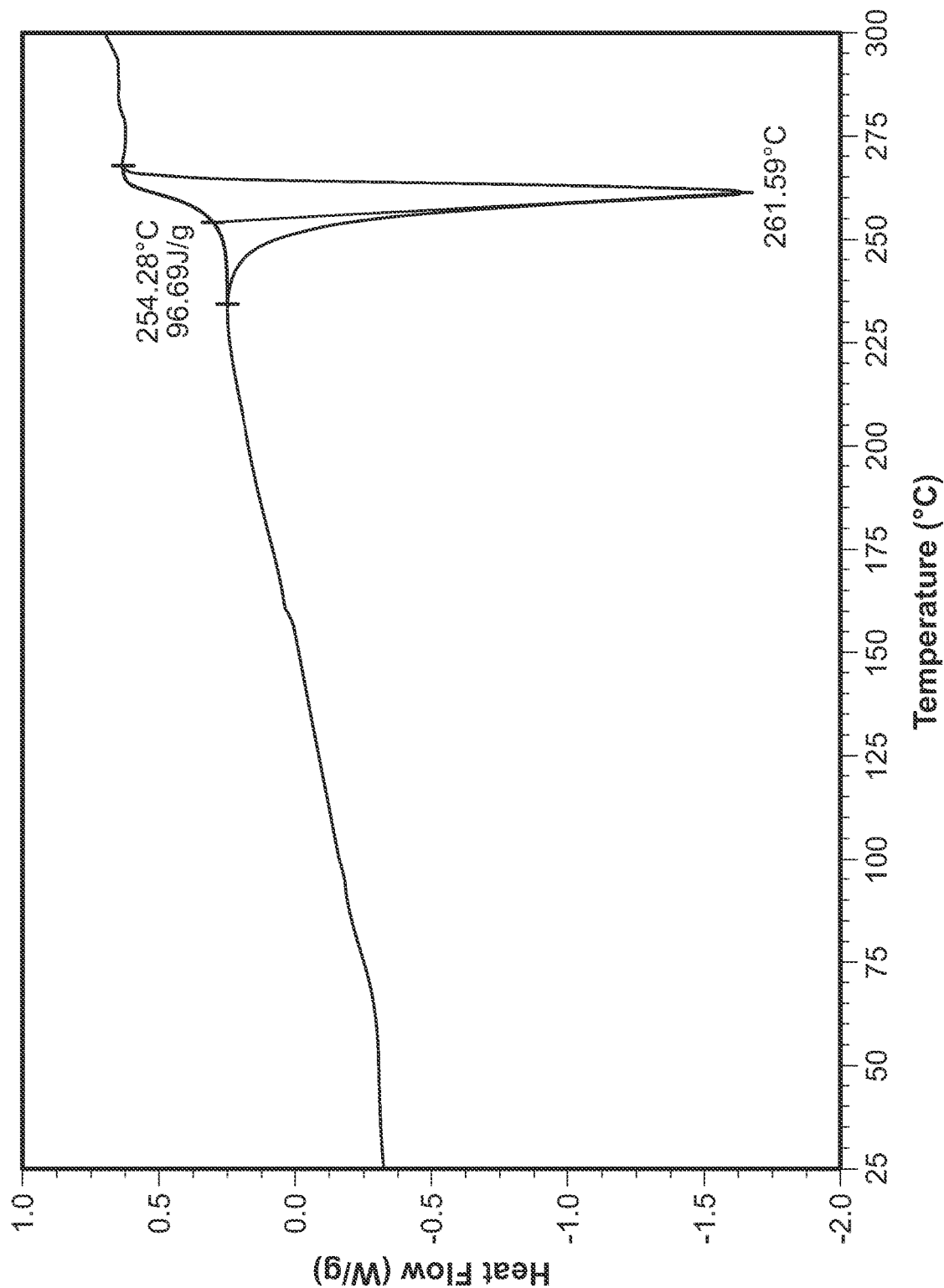
FIG. 16 illustrates the DSC profile pattern of the [2-(1H-indol-3-yl)-1H-imidazol-4-yl](3,4,5-trimethoxyphenyl)methanone mesylate salt of Examples 1 or 2 that exhibited a fairly sharp melting onset endotherm with extrapolated onset temperature at about 254° C. to 265° C., peak temperature at about 261° C. to 268° C.
Figure 17:
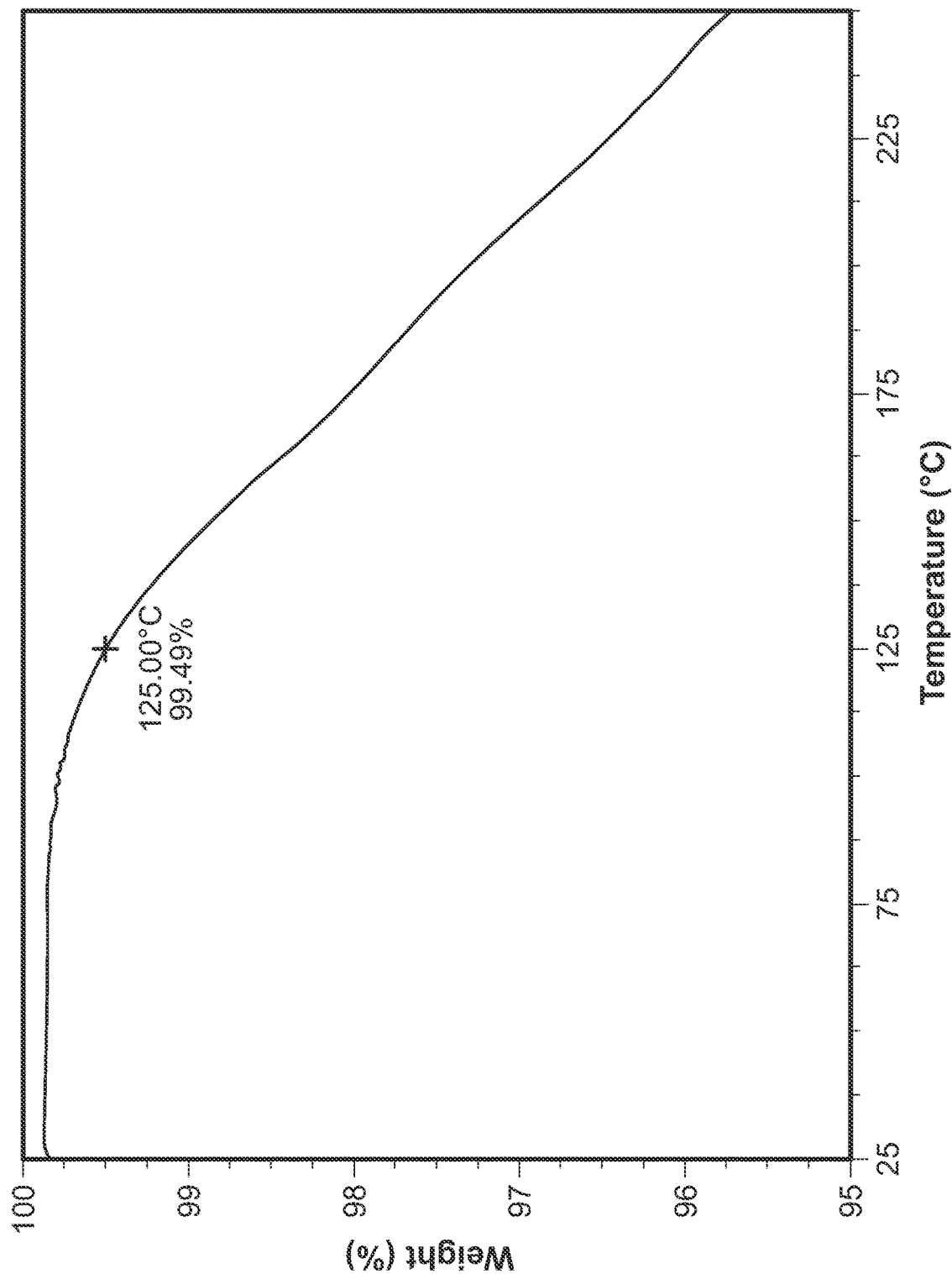
FIG. 17 illustrates the TGA profile of the [2-(1H-indol-3-yl)-1H-imidazol-4-yl](3,4,5-trimethoxyphenyl)methanone mesylate salt of Examples 1 or 2 that showed a weight loss of 0.51% from about 25° C. to 120-150° C., followed by decomposition.

The [2-(1H-indol-3-yl)-1H-imidazol-4-yl](3,4,5-trimethoxyphenyl)methanone mesylate salt was highly crystalline with good solubility in unbuffered water (less than 1 mg/mL). The XRD pattern of the [2-(1H-indol-3-yl)-1H-imidazol-4-yl](3,4,5-trimethoxyphenyl)methanone mesylate salt synthesized according to Example 1 exhibited a crystalline solid as illustrated in FIG. 15. The crystalline polymorph of the [2-(1H-indol-3-yl)-1H-imidazol-4-yl](3,4,5-trimethoxyphenyl)methanone mesylate salt was characterized by an XRD pattern having peaks at about 8.3, 9.9, 10.9, 17.5, and 19.9 2θ±0.2 2θ. The crystalline polymorph of the [2-(1H-indol-3-yl)-1H-imidazol-4-yl](3,4,5-trimethoxyphenyl)methanone mesylate salt was further characterized by an XRD pattern having peaks at 12.1, 18.8, 21.9, 24.5, and 28.2 2θ±0.2 2θ. The DSC profile exhibited a fairly sharp melting onset endotherm with extrapolated onset temperature at about 254° C. to 265° C., peak temperature at about 261° C. to 268° C. and enthalpy value of about 96.7 J/g to 128.5 J/g, as illustrated in FIG. 16. The TGA profile showed a weight loss of 0.51% from about 25° C. to 120-150° C., followed by decomposition, as illustrated in FIG. 17. The following examples are presented in order to more fully illustrate the preferred embodiments of the invention. They should in no way be construed, however, as limiting the broad scope of the invention.

EXAMPLES

Differential Scanning Calorimetry (DSC)

DSC data were collected on a TA Instruments DSC. In general, samples in the mass range of 1 to 10 mg were crimped in aluminum sample pans and scanned from 25° C. to about 250° C. or 300° C. at 10° C./minute using a nitrogen purge of 50 mL/min.

Proton Nuclear Magnetic Resonance Spectroscopy ($^1$H-NMR)

The samples were prepared by dissolving 1 to 10 mg of the active pharmaceutical ingredient (API) in deuterated chloroform with 0.05% (v/v) tetramethylsilane (TMS). The spectra were collected at ambient temperature on a Bruker 400 MHz NMR spectrometer.

X-Ray Powder Diffraction (XRD)

Solids generated from the recrystallization panels, slurry experiments, and from other means were analyzed by powder XRD. To mitigate preferred grain effects, a two dimensional detection system was used to collect all the XRD screening data. The two dimensional detector integrates along the concentric Debye cones which helps reduce pattern variation. If bright spots appear in the conical rings, it indicates strong preferred grain effects which can lead to considerable variability in the observed diffraction patterns. Although some samples of [2-(1H-indol-3-yl)-1H-imidazol-4-yl](3,4,5-trimethoxyphenyl)methanone HCl salt tended to exhibit mild preferred grain effects, overall [2-(1H-indol-3-yl)-1H-imidazol-4-yl](3,4,5-trimethoxyphenyl)methanone HCl did not appear to suffer from severe preferred grain effects. This resulted in XRD data that had low variability for samples of a given polymorphic form. X-ray powder diffraction (XRD) patterns were obtained using a Bruker D8 Discovery diffractometer equipped with an XYZ stage, laser video microscope for positioning and a Vantec 500 (Photon) detector. Collection times were nominally 120 seconds. A Cu Kα radiation 1.5406 angstrom source operating at 40 kV and 40 mA was used to irradiate the samples. The X-ray optics consists of a Gobel mirror coupled with a pinhole collimator of 0.5 mm. Theta-theta continuous scans were employed with a sample-detector distance of 30 cm, which gives an effective 2θ range of 4 to 40 °2θ. Samples were mounted on low background quartz plates.

Hygroscopicity—Dynamic Vapor Sorption (DVS)

DVS is a gravimetric technique that measures how quickly and how much of a solvent (water) is absorbed by a sample. The relative humidity or vapor concentration surrounding the sample is varied while the change in mass of the sample is measured. A vapor sorption isotherm shows the equilibrium amount of vapor absorbed as a function of relativity humidity. The mass values at each relative humidity step are used to generate an isotherm. Isotherms are divided in two components: sorption for increasing humidity steps and desorption for decreasing humidity steps. A plot of kinetic data is also used to show the change in mass and humidity as a function of time.

The samples were analyzed using a TA Q5000 automated dynamic vapor sorption analyzer. The samples were dried at higher temperature than ambient over a period of time and then cooled to 25° C. with a dry nitrogen purge over them until they no longer lost mass at 0% RH (relative humidity). The samples were then subjected to 0 to 90% RH, back to 10% RH at 25° C. in 10% RH steps.

Thermogravimetric Analysis (TGA)

Solids generated from the recrystallization panels, slurry experiments, and from other means were analyzed by TGA. TGA is an analytical test that determines how much mass of volatile materials is lost as the temperature of the sample is increased. The conditions for TGA were as specified where the TGA values are reported herein. Where not specified, the default conditions are: Sample Size of 5-20 mg (or appropriate); Temperature Range: 25° C. to 150° C.; Heating Rate: 10° C./minute; Purge Gas: Nitrogen; and Replicates: Single analysis.

Solid State Fourier Transform Infrared Spectroscopy (FT-IR)

Solids generated from the recrystallization panels, slurry experiments, and from other means were analyzed by this procedure of Fourier Transform Infrared spectroscopy (FT-IR). FT-IR is a qualitative chemical analysis tool to aid in determining the presence of specific functional groups and verifying the identity of a test sample compared to a reference sample. Depending on the submission, this Test Method was used for identification or characterization of polymorphic substances by infrared spectroscopy. Samples submitted for confirmation of identity were analyzed by comparison of the sample spectrum with a reference spectrum. A substance was positively identified when its FT-IR spectrum matches that of the reference. The spectra are considered to match when the number, relative intensities, and wavenumbers (cm-1) of the observed vibrational bands are consistent between spectra. If a difference appeared in the IR spectra of the analyte and standard that may have been due to hydration, the samples were dissolved in equal portions of the test substance and the standard in equal volumes of a suitable solvent, the solution were evaporated to dryness in similar containers under identical conditions, and the test repeated on the residues. The apparatus used in this method was the Thermo Scientific Nicolet iS20 FTIR spectrometer with Thermo Scientific OMNIC™ software and FTIR accessories (as needed) compatible for use with the spectrometer, including the following: (1) Attenuated Total Reflectance (ATR) accessory (e.g. Harrick SplitPea™ internal reflectance nanosampler, Thermo Scientific Smart™ iTX); (2) Transmittance sample holder accessory (e.g. used for KBr plates, demountable KBr liquid cells, KBr pellets, disposable PTFE cards); (3) Pellet die and press (as needed); (4) Vacuum oven or desiccator (as needed); or (5) Forced air drying oven (as needed). The following reagents, supplies, media and solutions were used as needed: (1) KBr plates (as needed); (2) Demountable KBr liquid cells (as needed); (3) KBr powder, spectroscopic/IR grade (as needed); (4) Disposable PTFE cards (as needed); (5) Appropriate solvent for dissolution of sample (as needed); and (6) General laboratory equipment (spatulas, mortar and pestle, vials, flasks, etc.) Generally, the physical properties of the sample and the purposes of the test defined the particular approach and instrument accessory used to collect the FTIR spectrum. Liquid samples were applied directly to a KBr plate or window, applied to a disposable PTFE card, or collected using a demountable liquid cell. Solid samples were analyzed with an ATR accessory or mixed with KBr (in a ~1:100 sample-KBr ratio), compressed into a pellet, and analyzed. Alternatively, the sample may have been dissolved in a suitable solvent and the spectrum collected using a demountable liquid cell.

Karl Fischer Titration (KF)

Solids generated from the recrystallization panels, slurry experiments, and from other means were analyzed by this procedure to determine water content. The samples were tested in a Karl Fischer apparatus suitable for coulometric titrations and volumetric titrations after being weighed on an analytical balance capable of weighing to 0.1 mg. The Karl Fisher apparatus was calibrated using deionized (DI) water or certified water standards before test samples were analyzed. Likewise, the calibration of the analytic balance was verified before weighing the sample. The sample was added directly to the vessel solution. If this was not possible, the sample was dissolved in an appropriate solvent which was then injected and a solvent blank was also analyzed.

Hot Stage Microscopy

A Linkam hot stage accessory was used in tandem with the microscope. The specimens were mounted on a microscope slide with a cover glass. The samples were heated from room temperature through melting using a Linkam TMS 94 temperature control and Linksys 32 data capture software system. Observations of possible phase change, melting, recrystallization, decomposition, etc. were recorded.

Visual Solubility

Milligram size quantities of each sample were placed into a vial. A certain amount of solvent was added and the vials were agitated for a few minutes, followed by visual observation for remaining solids. The solvent was incrementally added until the solids were dissolved, or a maximum volume of solvent was added and the experiment was terminated.

Example 1: Polymorphic Characterization of the Free Base; and Small Scale Salt Synthesis An amorphous form of the free base known as Form I of [2-(1H-indol-3-yl)-1H-imidazol-4-yl](3,4,5-trimethoxyphenyl)methanone served as the source material for polymorph screening of the free base. Polymorphs of the free base were screened by recrystallization and solvent slurry methods described in Examples 3 and 4. A process to make a crystalline polymorphic Form II of [2-(1H-indol-3-yl)-1H-imidazol-4-yl](3,4,5-trimethoxyphenyl)methanone free base (Form II) was by recrystallization of an amorphous form (Form I) of the free base (FIG. 1). Other processes that resulted in Form II of the free base included non-competitive single solvent slurry experiments performed by the process described in Example 4 using the amorphous form of [2-(1H-indol-3-yl)-1H-imidazol-4-yl](3,4,5-trimethoxyphenyl)methanone free base (Form I). An excess amount of free base (Form I) was slurried in methanol, ethanol, acetone, acetonitrile, ethyl acetate, tetrahydrofuran (THF) or toluene. The suspensions were slurried for several days at ambient temperature. The solids were collected by filtration and analyzed by X-ray powder diffraction (XRD). Samples slurried in acetone, THF and toluene yielded Form II of the free base as shown by the superimposition of XRD spectra from these experiments as shown in FIG. 4. FIG. 1 illustrates the XRD pattern for Form II of the free base from recrystallization. Form II of the free base is characterized by an XRD pattern having peaks at about 10.8, 15.3, 15.9, 18.6, and 25.9 2θ±0.2 2θ. Form II of the free base is further characterized by an XRD pattern having peaks at 14.4, 17.8, 20.0, 24.7, and 26.8 2θ±0.2 2θ.

As illustrated in FIG. 2, the DSC for Form II of [2-(1H-indol-3-yl)-1H-imidazol-4-yl](3,4,5-trimethoxyphenyl)methanone free base showed a sharp melting endotherm with an extrapolated onset temperature of 205.2° C., with a peak temperature 208.7° C. The DSC indicated an enthalpy value of 103.9 J/g. A small endothermic dip observed at 190° C. could indicate a phase transformation. The thermogravimetric analysis (TGA) thermogram indicated that Form II of the [2-(1H-indol-3-yl)-1H-imidazol-4-yl](3,4,5-trimethoxyphenyl)methanone free base had about 0.2 wt % loss at 150° C. and continued to lose weight and as shown in FIG. 3. As mentioned above, [2-(1H-indol-3-yl)-1H-imidazol-4-yl](3,4,5-trimethoxyphenyl)methanone free base samples of Form I slurried (following the method of Example 4) in acetone, THF, and or toluene yielded XRD patterns similar to FIG. 1, which was an indication that the XRD pattern of Form II represented the stable form of the free base (FIG. 4). This also indicated that solvent slurry processes to make Form II of the free base from the amorphous Form I of the free base can be achieved using, alternatively, acetone, THF, or toluene.

Small scale Polymorphic Salt Synthesis: The typical experiment to synthesize a polymorphic salt was carried out as follows. The free base of [2-(1H-indol-3-yl)-1H-imidazol-4-yl](3,4,5-trimethoxyphenyl)methanone was dissolved in methanol (about 5 mL), salt forming acid solutions (0.1 mmol/mL, in methanol) were added, and the solution was mixed. The ratio of free base to acid was about 1 to 1.1 molar ratios. The samples were crystallized under nitrogen purge (~1 psi) at ambient temperature. The isolated samples were examined by XRD. At least hydrochloric, citric, phosphoric and methanesulfonic salt forming acids were used to produce the (mono)hydrochloride, citrate, (mono)phosphate and mesylate salts. These same salts were scaled up to confirm XRD patterns and DSC, TGA and DVS outputs are reproducible and for any additional characterization needed.

Example 2: Scale Up of Polymorphic Salt Syntheses and Characterization of Scaled Up Salts The monohydrochloride (stated as HCl or hydrochloride elsewhere herein), citrate, monophosphate (stated as phosphate elsewhere herein), and mesylate (ester of methanesulfonic acid) polymorphic salts were selected for scale-up. The salts were prepared at 200-500 mg scale to facilitate additional testing and determine reproducibility. Typical procedures are found in Table 1. The solids were collected by evaporation at ambient condition with nitrogen purge at ~2 psi. All solids yielded the same XRD patterns as seen in the earlier experiments at small scale and were reproducible.

TABLE 1

Synthetic process for scale-up of salts

| Sample | Free Base | Salt | Solvent | Salt Forming Acid (0.1 mM, in MeOH) |
|---|---|---|---|---|
| 1 | ~450 mg | Hydrochloride | Methanol | Hydrochloric acid, 7.3 mL |
| 2 | ~250 mg | Citrate | Methanol | Citric acid, 7.3 mL |
| 3 | ~290 mg | Phosphate | Methanol | o-Phosphoric acid, 7.3 mL |
| 4 | ~230 mg | Mesylate | Methanol | Methanesulfonic acid, 7.3 mL |

A salt screening study was performed to identify suitable polymorphic salts formed by reaction with from a library of salt forming acids with [2-(1H-indol-3-yl)-1H-imidazol-4-yl](3,4,5-trimethoxyphenyl)methanone free base, as described in Examples 1 and 2. Originally, the characterization of salts was done at a small scale (40 mg) with four salts and deemed to produce desirable polymorphs. The small scale syntheses and characterizations were performed as described in Example 1. The preferred salts from Example 1 were the hydrochloride, citrate, phosphate, and mesylate salts of [2-(1H-indol-3-yl)-1H-imidazol-4-yl](3,4, 5-trimethoxyphenyl)methanone. Each salt was scaled up and analyzed for crystallinity, thermal properties, aqueous solubility and hygroscopicity. All polymorphs or salts were contemplated for processability, therapeutic use, and other factors. The scaled-up salt syntheses were described in this example and Table 1 (above) and characterized below.

Since HCl is a Class I salt forming acid, the [2-(1H-indol-3-yl)-1H-imidazol-4-yl](3,4,5-trimethoxyphenyl)methanone hydrochloride salt was synthesized to provide a Class I salt with lower safety risk relative to other salt forms. Class I salts possess unrestricted use because they form physiologically ubiquitous ions or they occur as intermediate metabolites in biochemical pathways. The [2-(1H-indol-3-yl)-1H-imidazol-4-yl](3,4,5-trimethoxyphenyl)methanone hydrochloride salt formed in Example 2 was crystalline, polymorphic, and had good solubility in unbuffered water (less than 1 mg/mL). This unnamed polymorph of the hydrochloride salt also showed evidence of possible hydrate formation at approximately 30-40% RH, in particular at about 50% RH.

The XRD pattern of the [2-(1H-indol-3-yl)-1H-imidazol-4-yl](3,4,5-trimethoxyphenyl)methanone hydrochloride salt formed in Examples 1 and 2 indicated the compound was crystalline, as illustrated in FIG. 5. The crystalline polymorph of the HCl salt formed in Examples 1 and 2 does not appear to correlate with any of the other polymorphic forms of the [2-(1H-indol-3-yl)-1H-imidazol-4-yl](3,4,5-trimethoxyphenyl)methanone hydrochloride salt characterized herein, which include Forms A, B, $C_H$, D, E, E1, $F_H$, $G_H$, H, and I (see supra and infra). This crystalline polymorph of the [2-(1H-indol-3-yl)-1H-imidazol-4-yl](3,4,5-trimethoxyphenyl)methanone hydrochloride salt formed in Examples 1 and 2 is characterized by an XRD pattern having peaks at about 10.8, 13.3, 21.5, 23.1, and 35.2 2θ±0.2 2θ. This crystalline polymorph of the [2-(1H-indol-3-yl)-1H-imidazol-4-yl](3,4,5-trimethoxyphenyl)methanone hydrochloride salt formed in Examples 1 and 2 is further characterized by an XRD pattern having peaks at 10.5, 14.1, 16.1, and 26.2 2θ±0.2 2θ. The DSC profile exhibited multiple thermal events prior to the eventual melting onset endotherm at approximately 235.7° C., as illustrated in FIG. 6. The TGA profile showed a continuous loss in weight with a weight loss of about 0.54% to 4.1% from 25° C. to 110° C., as illustrated in FIG. 7. Hygroscopicity was determined with dynamic vapor sorption (DVS). The DVS data exhibited non-stoichiometric uptake of water as hydrates that may form above 30-40% RH (relative humidity) in a complex and a total adsorption of water of approximately 8.8 wt % to 14.9 wt % at 90% RH, as illustrated in FIG. 8.

The [2-(1H-indol-3-yl)-1H-imidazol-4-yl](3,4,5-trimethoxyphenyl)methanone citrate salt had moderate crystallinity and had good solubility in unbuffered water (approximately 1 mg/mL). The [2-(1H-indol-3-yl)-1H-imidazol-4-yl](3,4,5-trimethoxyphenyl)methanone citrate salt was polymorphic and showed evidence of possible dihydrate formation at approximately 30-40% RH, and in particular at 60% RH. The XRD pattern of the small scale citrate salt (synthesized according to Example 1) indicated a lowly ordered crystalline solid, as illustrated in FIG. 9. The crystalline polymorph of the [2-(1H-indol-3-yl)-1H-imidazol-4-yl](3,4,5-trimethoxyphenyl)methanone citrate salt is characterized by an XRD pattern having peaks at about 9.7, 10.7, 15.1, 15.6, and 22.1 2θ±0.2 2θ. The crystalline polymorph of the [2-(1H-indol-3-yl)-1H-imidazol-4-yl](3,4,5-trimethoxyphenyl)methanone citrate salt is further characterized by an XRD pattern having peaks at 18.6, 19.2, 26.4, and 27.1 2θ±0.2 2θ. The DSC profile exhibited a small exothermic transition at approximately 130° C. immediately followed by a broad melting onset endotherm at approximately 184.5° C., as illustrated in FIG. 10. The TGA profile showed a weight loss of about 0.38% to 1.13% from 25° C. to 125° C. followed by decomposition, which was graphically illustrated in FIG. 11.

The [2-(1H-indol-3-yl)-1H-imidazol-4-yl](3,4,5-trimethoxyphenyl)methanone phosphate salt (synthesized according to Example 1) showed good crystallinity and good solubility in unbuffered water (less than 1 mg/mL). The XRD pattern of the crystalline polymorph of the [2-(1H-indol-3-yl)-1H-imidazol-4-yl](3,4,5-trimethoxyphenyl) methanone phosphate salt indicated crystallinity that exhibited preferred grain orientation, as illustrated in FIG. 12. The crystalline polymorph of the [2-(1H-indol-3-yl)-1H-imidazol-4-yl](3,4,5-trimethoxyphenyl)methanone phosphate salt is characterized by an XRD pattern having peaks at about 5.7, 9.3, 12.4, 12.6, and 18.8 2θ±0.2 2θ. The crystalline polymorph of the [2-(1H-indol-3-yl)-1H-imidazol-4-yl](3,4, 5-trimethoxyphenyl)methanone phosphate salt is further characterized by an XRD pattern having peaks at 9.7, 10.9, 11.6, and 20.7 2θ±0.2 2θ. The DSC profile exhibited loss of volatiles at about 149° C. to 152° C. immediately followed by exothermic recrystallization at 158.7° C. and a melting onset endotherm at approximately 216° C. to 219° C., followed by decomposition, as illustrated in FIG. 13. The TGA profile showed a continuous loss in weight with a weight loss of about 2.6% to 2.88% probably due to loss of volatiles from 25° C. to 100° C. followed by further decomposition, as illustrated in FIG. 14.

The [2-(1H-indol-3-yl)-1H-imidazol-4-yl](3,4,5-trimethoxyphenyl)methanone mesylate salt was highly crystalline with good solubility in unbuffered water (less than 1 mg/mL). The XRD pattern of the crystalline polymorph of the [2-(1H-indol-3-yl)-1H-imidazol-4-yl](3,4,5-trimethoxyphenyl)methanone mesylate salt (synthesized according to Example 1) exhibited a crystalline solid as illustrated in FIG. 15. The crystalline polymorph of the [2-(1H-indol-3-yl)-1H-imidazol-4-yl](3,4,5-trimethoxyphenyl)methanone mesylate salt is characterized by an XRD pattern having peaks at about 8.3, 9.9, 10.9, 17.5, and 19.9 2θ±0.2 2θ. The crystalline polymorph of the [2-(1H-indol-3-yl)-1H-imidazol-4-yl] (3,4,5-trimethoxyphenyl)methanone mesylate salt is further characterized by an XRD pattern having peaks at 12.1, 18.8, 21.9, 24.5, and 28.2 2θ±0.2 2θ. The DSC profile exhibited a fairly sharp melting onset endotherm with extrapolated onset temperature at about 254° C. to 265° C., peak temperature at about 261° C. to 268° C. and enthalpy value of about 96.7 J/g to 128.5 J/g, as illustrated in FIG. 16. The TGA profile showed a weight loss of 0.51% from about 25° C. to 120-150° C., followed by decomposition, as illustrated in FIG. 17.

Polymorphic screening of the hydrochloride (HCl) salt of [2-(1H-indol-3-yl)-1H-imidazol-4-yl](3,4,5-trimethoxyphenyl)methanone was conducted to determine the most thermodynamically stable polymorph(s) of the HCl salt. New polymorphs of the HCl salt were made by recrystallization (Example 3), solvent slurry (Examples 4 and 5) experiments, or as described in Example 6 or elsewhere herein. Resulting samples were characterized using at least X-ray powder diffraction (XRD), differential scanning calorimetry (DSC), and thermogravimetric analysis (TGA). Our studies revealed that [2-(1H-indol-3-yl)-1H-imidazol-4-yl](3,4,5-trimethoxyphenyl)methanone HCl salt is polymorphic, and several solid-state forms were made, identified as distinct, and characterized, as described in detail in Examples 3-6.

Example 3: Polymorphs Made Via Solvent Recrystallization of the [2-(1H-Indol-3-yl)-1H-imidazol-4-yl](3,4,5-trimethoxyphenyl)methanone Hydrochloride Salt Overview of Polymorph Screening: The results of the polymorph screening are provided below for each of the polymorphs A through I of the hydrochloride salt of the compound [2-(1H-indol-3-yl)-1H-imidazol-4-yl](3,4,5-trimethoxyphenyl)methanone. The processes that prepared these polymorphs are discussed below in the polymorph screening or characterization experiments. The purpose of the polymorph screen was to make as many crystalline polymorphic forms of the hydrochloride salt as possible, probe their relative stabilities, and characterize the processes by which they could be made. The screen was performed using solvent-based recrystallization followed by X-ray diffraction analysis of the solids (Example 3). Polymorph screening by suspension slurry experiments (Examples 4 and 5) was also employed to search for additional solid-state forms and explore their relative stabilities, as is also discussed herein. The detailed characterization of each of the polymorphs is presented in Example 6.

Solvent Recrystallization: Test material was recrystallized using various solvents where the scale of the recrystallization experiments was approximately 1 to 20 mL. The method used single and binary arrays of solvents, and saturation temperature, growth temperature, and evaporation rate (relative supersaturation) were criteria that were varied to determine optimal crystal growth conditions. Saturated solutions were prepared by agitating excess (as possible) test material in contact with the various solvent systems at the saturation temperature. The mother liquor was separated from the residual solids by filtration if solids remained in the solution. The mother liquor was then heated above the saturation temperature (overheated) to dissolve any remaining solids. The temperature of each solution was then adjusted to the growth temperature and a controlled nitrogen shear flow was introduced to begin solvent evaporation.

The recrystallization conditions for the four solvent based panels used during the study are summarized in Table 2. Each recrystallization panel contained from 8 to 18 wells. The wells within each panel contained different solvent compositions. Because of the different solvent composition in each well, it acted as a different crystal growth experiment.

TABLE 2

Summary of recrystallization panels for solvent-based polymorph screening

| Panel | Solvent | Saturation Temp. (° C.) | Overheat Temp. (° C.) | Growth Temp. (° C.) | N$_2$ Flow Rate (psi) | Evaporation Rate |
|---|---|---|---|---|---|---|
| 1 | Single | ~25 | ~45-50 | Ambient | 1.5 | Fast |
| 2 | Binary | ~25 | ~45-50 | Ambient | 1.5 | Fast |
| 3 | Binary | 25 | N/A | Ambient | N/A | Slow |
| 4 | Single/Binary | ~25 | ~45-50 | 40 | 1.5 | Fast |

Table 3 outlines the recrystallization procedure employed (Panel column), the solvent used(Vehicle column), and resulting polymorphic form (XRD column) made in the solvent-based portion of the polymorph screen. Based on the XRD analysis carried out on these polymorphic screening samples, new polymorphs of the [2-(1H-indol-3-yl)-1H-imidazol-4-yl](3,4,5-trimethoxyphenyl)methanone hydrochloride salt were made and characterized. The recrystallization processes of Table 3 made polymorphs designated as Form A, Form B, Form E, and Form E1.

TABLE 3

Results of the recrystallization panels

| Panel | Vehicle | XRD | DSC |
|---|---|---|---|
| 1 | 2-propanol | Form E | Melt onset endotherm at 239.6° C.; TGA: Loss at 100° C. is 0.24 wt % |
| 3 | 1-propanol/dioxane | Form E | — |
| 4 | Ethanol | Form E | Monotropic solid-solid phase transition with exothermic crystallization at 180.1° C. followed by melting onset endotherm at 240.4° C. |
| 4 | 2-propanol/dichloromethane | Form E1 | Melting onset endotherm at 243.2° C. |
| 4 | methanol/acetonitrile | Form B | Monotropic solid-solid phase transition with exothermic crystallization at 176.7° C. followed by melting onset endotherm at 221.8° C. |
| 4 | 2-propanol/trichloromethane | Form E1 | Melting onset endotherm at 234.7° C. |
| 4 | 1-propanol/nitromethane | Form A | Melting onset endotherm at 231.2° C. |

Based on the XRD analysis, new polymorphs of the [2-(1H-indol-3-yl)-1H-imidazol-4-yl](3,4,5-trimethoxyphenyl)methanone hydrochloride salt were obtained via the recrystallizations carried out as described above. The polymorphs were designated as Form A, Form B, Form E, and Form E1, and are described in detail in Example 6. These polymorphs were made as follows:

The recrystallization experiments above demonstrated multiple processes by which polymorphic forms of the HCl salt can be made, to include Form A, Form B, Form E, and Form E1. Form A was made by recrystallization via the procedure of Panel 4 from a 1-propanol/nitromethane binary solvent mixture (Tables 2 and 3). Briefly, [2-(1H-indol-3-yl)-1H-imidazol-4-yl](3,4,5-trimethoxyphenyl)methanone hydrochloride salt was dissolved in 1-propanol/nitromethane at saturating concentrations at 25° C., heated to 45-50° C., and fast evaporated under 1.5 psi of $N_2$ flow at 40° C. The results provide a facile process to make Form A of the [2-(1H-indol-3-yl)-1H-imidazol-4-yl](3,4,5-trimethoxyphenyl)methanone hydrochloride salt.

Form B was also made by recrystallization via the procedure of Panel 4 from a methanol/acetonitrile binary solvent mixture (Tables 2 and 3). Briefly, [2-(1H-indol-3-yl)-1H-imidazol-4-yl](3,4,5-trimethoxyphenyl)methanone hydrochloride salt was dissolved in methanol/acetonitrile at saturating concentrations at 25° C., heated to 45-50° C., and fast evaporated under 1.5 psi of $N_2$ flow at 40° C. The results provided a facile process to make Form B of the [2-(1H-indol-3-yl)-1H-imidazol-4-yl](3,4,5-trimethoxyphenyl)methanone hydrochloride salt.

Form E was made by recrystallization via the procedure of Panel 1 from 2-propanol (Tables 2 and 3). Briefly, [2-(1H-indol-3-yl)-1H-imidazol-4-yl](3,4,5-trimethoxyphenyl)methanone hydrochloride salt was dissolved in 2-propanol at saturating concentrations at 25° C., heated to 45-50° C., and fast evaporated under 1.5 psi of $N_2$ flow at ambient temperature. Form E was also made by recrystallization via the procedure of Panel 3 from 1-propanol/dioxane binary solvent mixture (Tables 2 and 3). Briefly, [2-(1H-indol-3-yl)-1H-imidazol-4-yl](3,4,5-trimethoxyphenyl)methanone hydrochloride salt was dissolved in 1-propanol/dioxane at saturating concentrations at 25° C., and slowly evaporated at ambient temperature. Form E was also made from recrystallization via the procedure of Panel 4 from ethanol (Tables 2 and 3). Briefly, [2-(1H-indol-3-yl)-1H-imidazol-4-yl](3,4,5-trimethoxyphenyl)methanone hydrochloride salt was dissolved in ethanol at saturating concentrations at 25° C., heated to 45-50° C., and fast evaporated under 1.5 psi of $N_2$ flow at 40° C. The above results provided three facile processes to make Form E of the [2-(1H-indol-3-yl)-1H-imidazol-4-yl](3,4,5-trimethoxyphenyl)methanone hydrochloride salt. Form E1 only differed slightly from Form E in a few peaks in the in the 10-12° 2θ region of their XRD patterns suggesting very similar physical properties. Form E1 was made by recrystallization via the procedure of Panel 4 from 2-propanol/dichloromethane binary solvent mixture (Tables 2 and 3). Briefly, [2-(1H-indol-3-yl)-1H-imidazol-4-yl](3,4,5-trimethoxyphenyl)methanone hydrochloride salt was dissolved in 2-propanol/dichloromethane at saturating concentrations at 25° C., heated to 45-50° C., and fast evaporated under 1.5 psi of $N_2$ flow at 40° C. Form E1 was also made by recrystallization via the procedure of Panel 4 from 2-propanol/trichloromethane binary solvent mixture (Tables 2 and 3). Briefly, [2-(1H-indol-3-yl)-1H-imidazol-4-yl](3,4,5-trimethoxyphenyl)methanone hydrochloride salt was dissolved in 2-propanol/trichloromethane at saturating concentrations at 25° C., heated to 45-50° C., and fast evaporated under 1.5 psi of $N_2$ flow at 40° C. The above results provided three facile processes to make Form E1 of the [2-(1H-indol-3-yl)-1H-imidazol-4-yl](3,4,5-trimethoxyphenyl)methanone hydrochloride salt.

Example 4: Polymorphs Made Via Non-Competitive Slurry Experiments of the [2-(1H-Indol-3-yl)-1H-imidazol-4-yl](3,4,5-trimethoxyphenyl)methanone Hydrochloride Salt In addition to the solvent recrystallization experiments (Example 3), non-competitive slurry (Example 4) and competitive slurry (Example 5) experiments were performed to make new solid-state forms. Non-competitive slurry experiments were performed to search for new solid-state forms. These experiments relied on solubility differences of different polymorphic forms (if the compound is polymorphic). As such, only polymorphs having a lower solubility (more stable) than the original crystalline form can result from a noncompetitive slurry experiment.

Essentially, when a solid is mixed with a solvent or solvents as slurry (solids suspended in a liquid), this results in a saturated solution. The solution is saturated with respect to the polymorphic form dissolved. However, the solution is supersaturated with respect to any polymorphic form that is more stable (more stable forms have lower solubility) than the polymorphic form initially dissolved. Therefore, any of the more stable polymorphic forms can nucleate and precipitate from solution. In addition, noncompetitive slurry experiments are often useful in identifying solvents that form solvates with the compound.

The slurry experiments were performed by exposing excess starting material, which was in all cases in this experiment Form B, to neat single and binary solvent systems and agitating the resulting suspensions for several days at ambient temperature. The solids were vacuum filtered and analyzed by XRD to determine the resulting form. To avoid possible desolvation or physical change after isolation, the samples were not further dried before X-ray analysis. A summary of non-competitive slurry experiments in single and binary solvent system are shown in Tables 4 and 5 (below).

TABLE 4

Non-competitive slurry experiments: Single solvent systems

| Sample | Solvent | Initial Form | Duration | Final Form |
|---|---|---|---|---|
| 1 | Methanol | Form B | 14 Days | Solvate |
| 2 | Ethanol | Form B | 14 Days | Solvate |
| 3 | Water | Form B | 14 Days | Low Crystallinity |
| 4 | Acetone | Form B | 14 Days | Form D |
| 5 | THF | Form B | 14 Days | Form B |
| 6 | Ethyl acetate | Form B | 14 Days | Form B |
| 7 | Acetonitrile | Form B | 14 Days | Form D |
| 8 | Methylene chloride | Form B | 14 Days | Form B |
| 9 | Toluene | Form B | 14 Days | Form B |
| 10 | Heptane | Form B | 14 Days | Form B |

The XRD patterns of the samples from single solvent systems in methanol or ethanol slurries after 14 days were different from each other and from the starting material. Both of these were solvates that were not studied further (Table 4). The solids from slurrying in water yielded a diffraction pattern that showed very low order of crystallinity. The samples from acetone and acetonitrile slurries after 14 days yielded a different XRD pattern from the starting material. This new form was designated as Form D (Table 4). The remaining slurry experiments in tetrahydofuran (THF), methylene chloride, ethyl acetate, toluene and heptane resulted in no significant change to the starting polymorphic form (Form B) based on the X-ray scattering behavior after 14 days of treatment.

A process to make Form D was observed in these non-competitive slurries experiments in which Form B was slurried in the non-aqueous solvent acetone for 14 days as described in Table 4. Briefly, excess of Form B was added to neat acetone until saturated. The resulting suspension was agitated for fourteen days at ambient temperature. The solids were vacuum filtered and analyzed by XRD to determine that Form D was made. To avoid possible desolvation or physical change after isolation, the samples were not further dried before X-ray analysis. Another process to make Form D was observed in these non-competitive slurries experiments in which Form B was slurried in the non-aqueous solvent acetonitrile for 14 days as described in Table 4. Briefly, excess of Form B was added to neat acetonitrile until saturated. The resulting suspension was agitated for fourteen days at ambient temperature. The solids were vacuum filtered and analyzed by XRD to determine that Form D was made. To avoid possible desolvation or physical change after isolation, the samples were not further dried before X-ray analysis. These observations provide processes by which Form D of the [2-(1H-indol-3-yl)-1H-imidazol-4-yl](3,4,5-trimethoxyphenyl)methanone hydrochloride salt can be made. The data suggests that Form D is more stable than Form B in some solvent systems.

TABLE 5

Non-competitive slurry experiments: Binary Solvent

| Sample | Solvent | Initial Form | Duration | Final Form |
|---|---|---|---|---|
| 1 | Methanol/Water | Form B | 11 Days | Low crystallinity |
| 2 | MeOH/Acetone | Form B | 11 Days | Low crystallinity |
| 3 | Ethanol/Toluene | Form B | 11 Days | Form E1 |
| 4 | Methanol/DCM | Form B | 11 Days | Solvate |
| 5 | ACN/Acetone | Form B | 11 Days | Form E1 |
| 6 | TFE/EtOAc | Form B | 11 Days | Low order crystallinity |
| 7 | Ethanol/acetonitrile | Form B | 11 Days | Form E1 |
| 8 | 1-Propanol/EtOAc | Form B | 11 Days | Form E1 |
| 9 | 2-Propanol/THF | Form B | 11 Days | Form E1 |
| 10 | TFE/DCM | Form B | 11 Days | Form B |

The XRD patterns of the samples from the binary solvent system methanol/water, methanol (MeOH)/acetone, and trifluoroethanol (TFE)/ethyl acetate (EtOAc) slurries after 11 days gave patterns that had low crystallinity (Table 5). The samples from methanol/dichloromethane (DCM) yielded different XRD patterns from the starting material and was grouped as a solvate. The slurry samples from ethanol/toluene, acetonitrile (ACN)/acetone, ethanol/acetonitrile, 1-propanol/ethyl acetate (EtOAc), and 2-propanol/tetrahydrofuran (THF) had different XRD patterns from the starting material and were eventually designated as Form E1 (Table 5). The combination of trifluoroethanol (TFE)/dichloride methane (DCM) slurry experiments resulted in no significant change to the starting polymorphic form (Form B) based on the X-ray scattering behavior after 11 days of treatment.

Form E1 resulted from non-competitive slurry experiments starting from Form B incubated in five different binary solvent systems (see Table 5 at rows 3, 5, and 7-9 of Example 4). A process to make Form E1 was observed in these non-competitive slurries experiments in which Form B was slurried in the non-aqueous binary solvent system of ethanol/toluene for 11 days as described in Table 5. Briefly, excess of Form B was added to an ethanol/toluene mixture until saturated. The resulting suspension was agitated for eleven days at ambient temperature. The solids were vacuum filtered and analyzed by XRD to determine that Form E1 was made. To avoid possible desolvation or physical change after isolation, the samples were not further dried before X-ray analysis. Another process to make Form E1 was observed in these non-competitive slurries experiments in which Form B was slurried in the non-aqueous binary solvent system of acetonitrile (ACN)/acetone for 11 days as described in Table 5. Briefly, excess of Form B was added to an acetonitrile (ACN)/acetone mixture until saturated. The resulting suspension was agitated for eleven days at ambient temperature. The solids were vacuum filtered and analyzed by XRD to determine that Form E1 was made. To avoid possible desolvation or physical change after isolation, the samples were not further dried before X-ray analysis. Another process to make Form E1 was observed in these non-competitive slurries experiments in which Form B was slurried in a non-aqueous binary solvent system of ethanol/acetonitrile for 11 days as described in Table 5. Briefly, excess of Form B was added to an ethanol/acetonitrile mixture until saturated. The resulting suspension was agitated for eleven days at ambient temperature. The solids were vacuum filtered and analyzed by XRD to determine that Form E1 was made. To avoid possible desolvation or physical change after isolation, the samples were not further dried before X-ray analysis. Another process to make Form E1 was observed in these non-competitive slurries experiments in which Form B was slurried in the non-aqueous binary solvent system of 1-propanol/ethyl acetate (EtOAc) for 11 days as described in Table 5. Briefly, excess of Form B was added to a 1-propanol/ethyl acetate (EtOAc) mixture until saturated. The resulting suspension was agitated for eleven days at ambient temperature. The solids were vacuum filtered and analyzed by XRD to determine that Form E1 was made. To avoid possible desolvation or physical change after isolation, the samples were not further dried before X-ray analysis. Another process to make Form E1 was observed in these non-competitive slurries experiments in which Form B was slurried in the non-aqueous binary solvent system of 2-propanol/tetrahydrofuran (THF) for 11 days as described in Table 5. Briefly, excess of Form B was added to a 2-propanol/tetrahydrofuran (THF) mixture until saturated. The resulting suspension was agitated for eleven days at ambient temperature. The solids were vacuum filtered and analyzed by XRD to determine that Form E1 was made. To avoid possible desolvation or physical change after isolation, the samples were not further dried before X-ray analysis. These data demonstrated that Form E1 is more stable than Form B in many solvent systems, and supports (Form E and) Form E1 as a relatively stable polymorph of the [2-(1H-indol-3-yl)-1H-imidazol-4-yl](3,4,5-trimethoxyphenyl)methanone hydrochloride salt compared to Form B.

Example 5: Polymorphs Made Via Competitive Slurry Experiments of the [2-(1H-Indol-3-yl)-1H-imidazol-4-yl](3,4,5-trimethoxyphenyl)methanone Hydrochloride Salt In addition to the solvent recrystallization and non-competitive slurry experiments, competitive slurry experiments were performed to make novel polymorphs and to determine the most stable polymorphic form of the [2-(1H-indol-3-yl)-1H-imidazol-4-yl](3,4,5-trimethoxyphenyl)methanone hydrochloride salt. The experiments relied on the solubility differences of different polymorphic forms. As such, only polymorphic forms (and solvates) having a lower solubility (more stable) than the form(s) initially dissolved can result from a competitive slurry experiment. Essentially, when a solid is dissolved in a (slurry) solvent, a saturated solution eventually results. The solution is saturated with respect to the polymorphic form dissolved. However, the solution is supersaturated with respect to any polymorphic form that is more stable (more stable forms have lower solubility) than the polymorphic form initially dissolved. Therefore, any of the more stable polymorphic forms can nucleate and precipitate from solution. In addition, competitive slurry experiments are often useful in identifying solvents that form solvates with the active pharmaceutical ingredient (API).

The slurry experiments were performed by exposing excess material of two (polymorphic) forms to a small volume of neat solvents and agitating the resulting suspensions for several days at ambient temperature. The solids were filtered and analyzed by XRD to determine the resulting form. To avoid possible desolvation or physical change after isolation, the samples were not dried before X-ray analysis. Table 6 contains the results of these competitive slurry experiments.

TABLE 6

Processes to make Form B, Form E, Form E1, and Form H by competitive slurry

| Sample | Form | Vehicle | XRD | Duration |
|---|---|---|---|---|
| 1 | $C_H$ + B | Methanol | Solvate | ~2 weeks |
| 2 | $C_H$ + B | Acetone | Unknown | ~2 weeks |
| 3 | $C_H$ + B | Acetonitrile | Unknown | ~2 weeks |
| 4 | $C_H$ + B | Ethyl acetate | Form B | ~2 weeks |
| 5 | B + D | 1-Propanol | Form E | ~2 weeks |
| 6 | B + D | Ethanol | Mixture | ~2 weeks |
| 7 | $C_H$ + B | 1-Propanol | Form E1 | ~2 weeks |
| 8 | $C_H$ + B | Ethanol | Unknown | ~2 weeks |
| 9 | A + B | 1-Propanol | Form E | ~2 weeks |
| 10 | A + D | 1-Propanol | Form E1 | ~2 weeks |
| 11 | B + E | 1-Propanol | Form E1 | ~2 weeks |
| 12 | D + E | 1-Propanol | Form E1 | ~2 weeks |
| 13 | E + H | 2-Propanol | Form H | 1 day |
| 14 | E + H | 2-Butanol | Form H | 1 day |

Form E was made when Form B and Form D were co-incubated in 1-propanol for about 2 weeks, which speaks to the relative stability of Form E relative to Form B or Form D (Table 6, row 5). Briefly, excess of Form B and Form D were added to neat 1-propanol until saturated. The resulting suspension was agitated for about two weeks at ambient temperature. The solids were vacuum filtered and analyzed by XRD to determine that Form E was made. To avoid possible desolvation or physical change after isolation, the samples were not further dried before X-ray analysis. Form E was also made when Form A and Form B were co-incubated in 1-propanol for about 2 weeks (Table 6, row 9). Briefly, excess of Form A and Form B were added to neat 1-propanol until saturated. The resulting suspension was agitated for about two weeks at ambient temperature. The solids were vacuum filtered and analyzed by XRD to determine that Form E was made. To avoid possible desolvation or physical change after isolation, the samples were not further dried before X-ray analysis. This data suggested that Form E was relatively stable as compared to Form A, Form B, and Form D. This is consistent with data from the recrystallization experiments where Form E (and Form E1) resulted from multiple solvent systems, and non-competitive slurry experiments where Form E1 resulted from Form B in multiple binary solvent systems.

Form E1 only differed slightly from Form E in a few peaks in the in the 10-12° 2θ region of their XRD patterns suggesting very similar physical properties. Data in this example suggested Form E1 has greater stability than Form E, but their physical characteristics are expected to be similar. Form E1 resulted from competitive slurry experiments as described in Table 6 at rows 7 and 10-12 involving binary combinations of Form A, Form B, Form $C_H$, Form D, and Form E (Example 5) suggesting that Form E1 is relatively stable compared to these other forms. Form E1 was made when Form $C_H$ and Form B were co-incubated in 1-propanol for about 2 weeks (Table 6, row 7). Briefly, excess of Form $C_H$ and Form B were added to neat 1-propanol until saturated. The resulting suspension was agitated for about two weeks at ambient temperature. The solids were vacuum filtered and analyzed by XRD to determine that Form E1 was made. To avoid possible desolvation or physical change after isolation, the samples were not further dried before X-ray analysis. Form E1 was also made when Form A and Form D were co-incubated in 1-propanol for about 2 weeks (Table 6, row 10). Briefly, excess of Form A and Form D were added to neat 1-propanol until saturated. The resulting suspension was agitated for about two weeks at ambient temperature. The solids were vacuum filtered and analyzed by XRD to determine that Form E1 was made. To avoid possible desolvation or physical change after isolation, the samples were not further dried before X-ray analysis. Form E1 was also made when Form B and Form E were co-incubated in 1-propanol for about 2 weeks (Table 6, row 11). Briefly, excess of Form B and Form E were added to neat 1-propanol until saturated. The resulting suspension was agitated for about two weeks at ambient temperature. The solids were vacuum filtered and analyzed by XRD to determine that Form E1 was made. To avoid possible desolvation or physical change after isolation, the samples were not further dried before X-ray analysis. Form E1 was also made when Form D and Form E were co-incubated in 1-propanol for about 2 weeks (Table 6, row 12). Briefly, excess of Form D and Form E were added to neat 1-propanol until saturated. The resulting suspension was agitated for about two weeks at ambient temperature. The solids were vacuum filtered and analyzed by XRD to determine that Form E1 was made. To avoid possible desolvation or physical change after isolation, the samples were not further dried before X-ray analysis.

The recrystallization (Example 3) and non-competitive slurry (Example 4) polymorph screening experiments suggested Form E and Form E1 to be the most stable forms made in those experiments. However, samples of Form E or Form E1 held at ambient conditions converted to Form H, suggesting Form H was more stable than either Form E or Form E1. To test this hypothesis, competitive slurry experiments (Example 5) were performed to demonstrate that Form H rapidly and completely converted to Form E to Form H.

Figure 32:
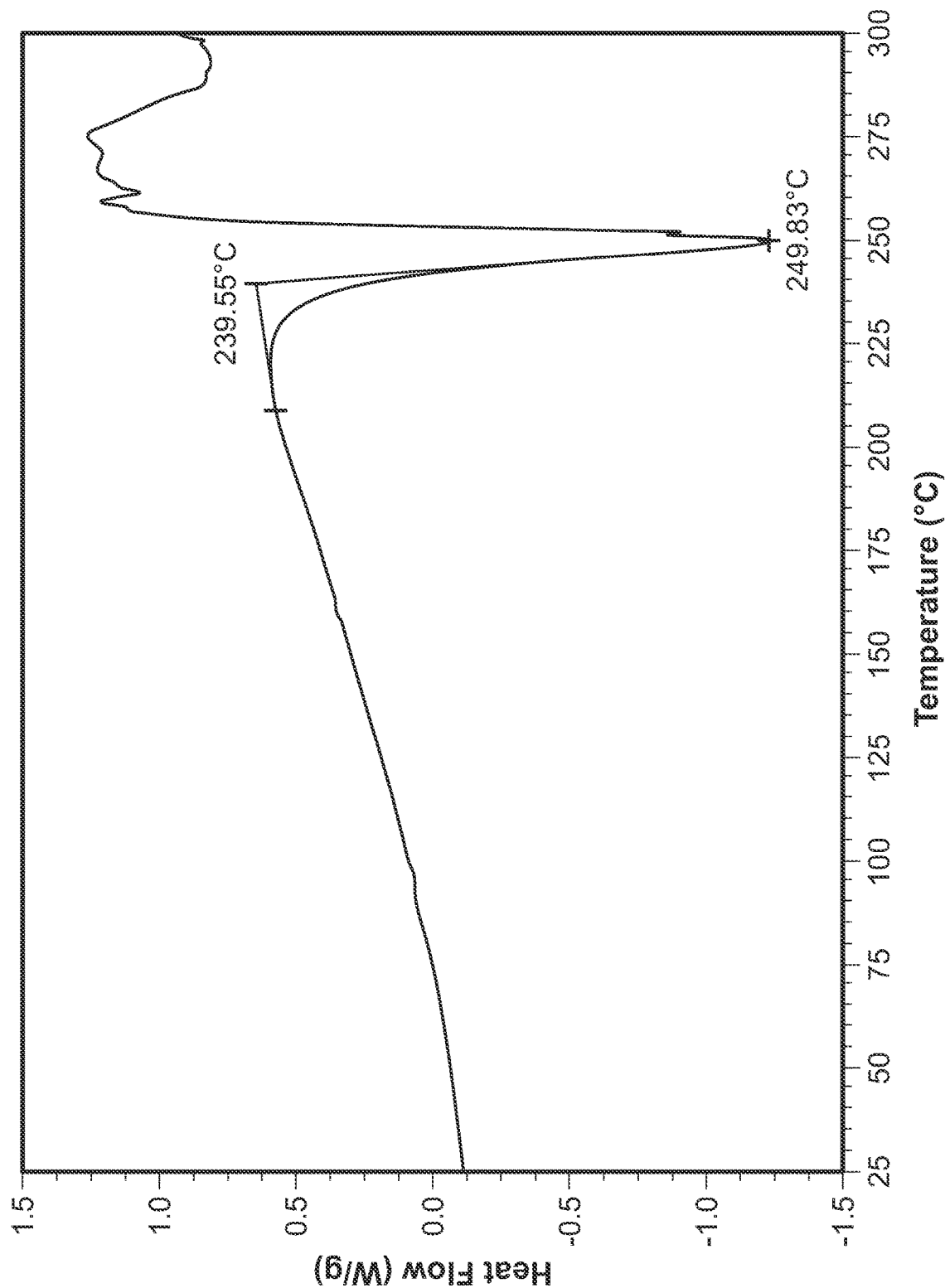
FIG. 32 illustrates the DSC thermogram of Form E that exhibited a melting onset endotherm at approximately 239.6° C. immediately followed by a large, broad decomposition.
Figure 34:
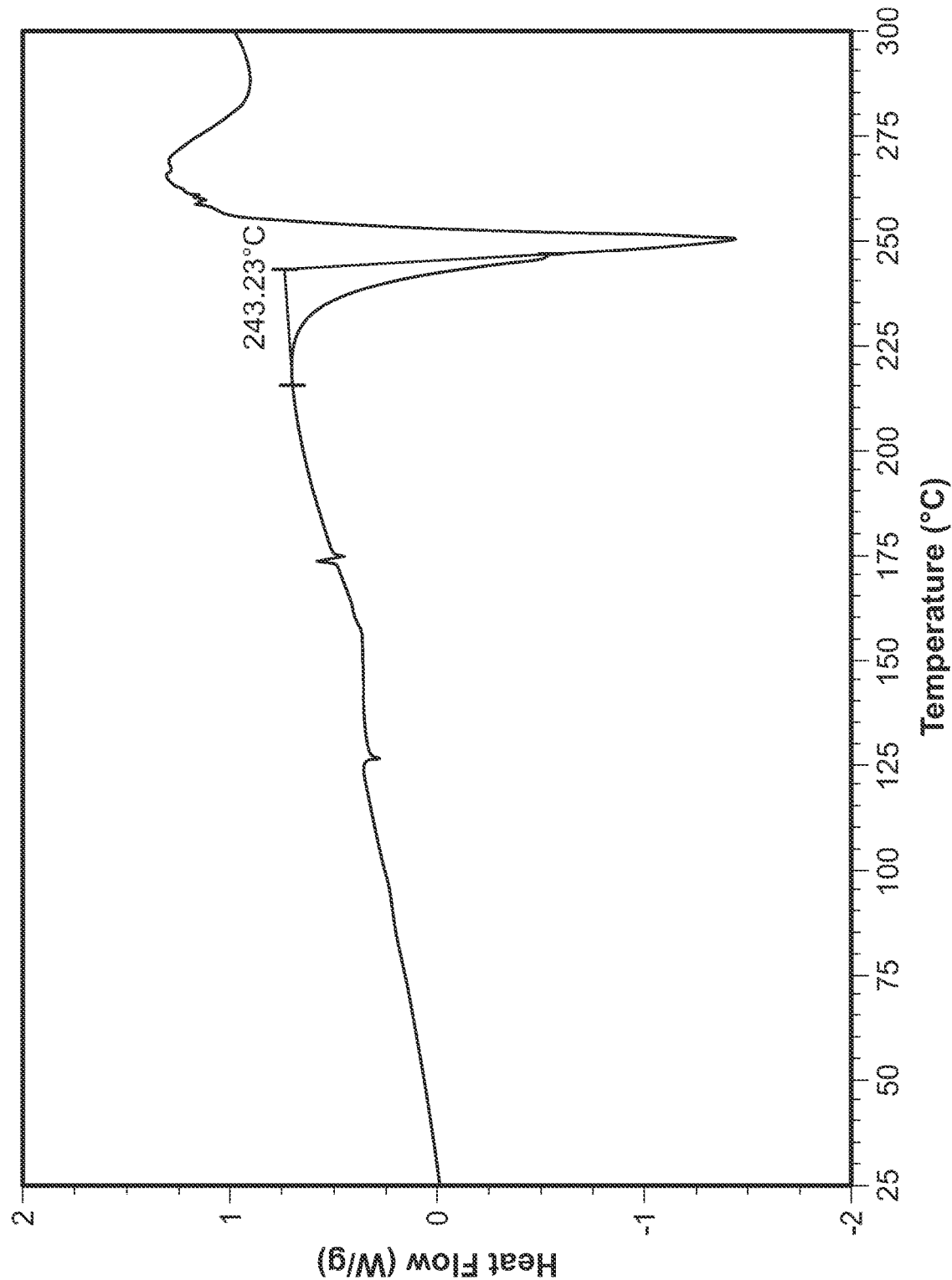
FIG. 34 illustrates the DSC thermogram of Form E1 that exhibited a melting onset endotherm at approximately 243.2° C. immediately followed by a large, broad decomposition.

Form H was synthesized by competitive slurry of Form E and Form H in 2-butanol or 2-propanol for 1 day (Table 6, row 13 and 14). In one embodiment, Form H resulted when Form E and Form H were co-incubated in 2-propanol for 1 day (Table 6, row 13). Briefly, excess of Form E and Form H were added to neat 2-propanol until saturated. The resulting suspension was agitated for 1 day at ambient temperature. The solids were vacuum filtered and analyzed by XRD to determine that Form H was made. To avoid possible desolvation or physical change after isolation, the samples were not further dried before X-ray analysis. In another experiment, Form H resulted when Form E and Form H were co-incubated in 2-butanol for 1 day (Table 6, row 14). Briefly, excess of Form E and Form H were added to neat 2-butanol until saturated. The resulting suspension was agitated for 1 day at ambient temperature. The solids were vacuum filtered and analyzed by XRD to determine that Form H was made. To avoid possible desolvation or physical change after isolation, the samples were not further dried before X-ray analysis. These rapid 1 day conversions in Table 6 to produce Form H, as compared to 11 days or ~14 days for other slurry conversions, suggested that Form H is relatively stable compared to Form E. From the initial slurry experiments (all samples except for the last two in Table 6), it appeared that Form E or E1 were the most stable forms observed during the study, and that their physical properties were similar. However, competitive slurries of Forms E and H in two different solvents showed that Form H was more stable than Form E (and presumably Form E1 as well). Further evidence supporting that Form H was more stable than Form E or Form E1 is presented in Example 6 where the differential scanning calorimetry (DSC) thermograms demonstrated a higher melting point for Form H (sharp highly enthalpy endotherm with an onset of 247.4° C., peak maximum of 250.1° C., and an enthalpy of fusion of 158.0 J/g (FIG. 45)) compared to Form E and E1 (broad melting onset endotherms at approximately 239.5° C. and 243.2° C. and relatively low enthalpies of fusion, respectively, immediately followed by decomposition (FIG. 32 and FIG. 34, respectively). Further, large scale Form H is produced by seeding the process to made Form E with a small amount of Form H. Based on competitive slurry and DSC experiments, Form H is expected to be the thermodynamically stable form.

Example 6: Characterization of the Polymorphs of the HCl Salt of [2-(1H-Indol-3-yl)-1H-imidazol-4-yl](3,4,5-trimethoxyphenyl)methanone by XRD, DSC, TGA, DVS, Etc This part of the report summarizes the polymorphs made in the polymorph screening research performed on the [2-(1H-indol-3-yl)-1H-imidazol-4-yl](3,4,5-trimethoxyphenyl)methanone hydrochloride salt. Polymorphism is the ability of a chemical entity to exist in different three-dimensional arrangements in the solid state. Different polymorphic forms of a compound can have different physical properties. The overall purpose of this effort was to screen the [2-(1H-indol-3-yl)-1H-imidazol-4-yl](3,4,5-trimethoxyphenyl)methanone hydrochloride salt for polymorphic behavior. The screen was designed to prepare as many novel crystalline forms as possible and characterize these polymorphs for use in a pharmaceutical product. The screen was performed using solvent recrystallizations under different conditions, and competitive and non-competitive slurry experiments to manipulate the solid-state form of the test material.

Samples generated during the study were characterized using differential scanning calorimetry (DSC), polarized light microscopy, thermogravimetric analysis (TGA), X-ray powder diffraction (XRD), Fourier transform infrared spectroscopy (FT-IR), and dynamic vapor sorption (DVS). The polymorph screen revealed that the [2-(1H-indol-3-yl)-1H-imidazol-4-yl](3,4,5-trimethoxyphenyl)methanone hydrochloride salt is polymorphic, and several solid state forms were made and characterized. Of these, the initial stable form made was Form E1 and the very similar to Form E. These were essentially the same except for minor changes in the diffraction pattern and DSC thermograms. Form H was made from samples of Form E or Form E1 that were stored at ambient conditions. Form H was characterized as a stable crystalline polymorph, and was more stable than Form E in competitive slurry experiments. Subsequently, the conversion of Form E or Form E1 to Form H was observed to be rapid and complete when Form E and/or Form E1 were made on the kilogram scale due the presence of gram quantities of Form H seed crystals (Example 7), supporting Form H as the thermodynamically stable polymorphic form of the [2-(1H-indol-3-yl)-1H-imidazol-4-yl](3,4,5-trimethoxyphenyl)methanone hydrochloride salt.

From the scale up of the salts of [2-(1H-indol-3-yl)-1H-imidazol-4-yl](3,4,5-trimethoxyphenyl)methanone (Example 2), the hydrochloride salt was selected for further study. The HCl salt was characterized polymorphic as multiple polymorphic forms were made and characterized as described below. Form A, Form B, Form $C_H$, Form D, Form E, Form E1, Form $F_H$, Form $G_H$, Form H, and Form I of the HCl salt were made and characterized below and summarized in Table 7. Based on diffraction behavior, each polymorphic form was studied to determine differentiation. The characterization of each hydrochloride polymorph form began with an X-ray powder diffraction (XRD) data comparison of each form with the other forms. This was generally followed by DSC and TGA analysis. Table 7 below summarizes the different forms made during the study.

TABLE 7

Summary of Forms A, B, $C_H$, D, E/E1, $F_H$, $G_H$, H, and I

| Form Designation | Description | Comments |
| --- | --- | --- |
| Form A | Metastable Polymorph | Good Crystallinity. Easy to obtain from solvent recrystallization. |
| Form B | Metastable Polymorph | Good crystallinity. Easy to obtain from solvent recrystallization. |
| Form $C_H$ | Monohydrate | Good crystallinity. Easily converts to Form B upon recrystallization. |
| Form D | Metastable Polymorph | Apparent metastable form. Form B converts to Form D in non-competitive slurries. |
| Form E/E1 | Apparent Stable Forms | Good crystallinity. Easy to obtain from recrystallization panel and slurries from forms described above. |

TABLE 7-continued

Summary of Forms A, B, $C_H$, D, E/E1, $F_H$, $G_H$, H, and I

| Form Designation | Description | Comments |
|---|---|---|
| Form $F_H$ | Hydrate | Good crystallinity. Hydrate made at room temperature that was characterized to possess 3+ molar equivalents of water based on Karl Fischer (KF) data. |
| Form $G_H$ | Hydrate | Moderate crystallinity. Hydrate made at room temperature that was characterized to possess 1-2 molar equivalents of water based on KF data. |
| Form H | Stable Form | Good crystallinity and thermal properties. Most stable polymorph based on conversion of Form E and Form E1 at ambient conditions, rapid conversion of Form E to Form H in competitive slurries, and also in kg scale synthesis. |
| Form I | Metastable Polymorph | Crystalline form made at room temperature. Sample converted to a mixture of Form $C_H$ and Form H after a month of storage. |

Form A and Form B were made from recrystallization as described in Example 3. Form D, Form E, Form E1, and Form H were made by recrystallization (Example 3), non-competitive slurry (Example 4), and/or competitive slurry (Example 5) experiments. Form $F_H$, Form $G_H$, and Form I were made in samples held at room temperature. Processes to make Form H involved competitive slurries of Form E in 2-butanol or 2-propanol as discussed in Example 5 or seeding of Form H crystals into the synthesis of other polymorphic forms of the HCl salt, including Form E and Form E1 (Example 7).

Figure 36:
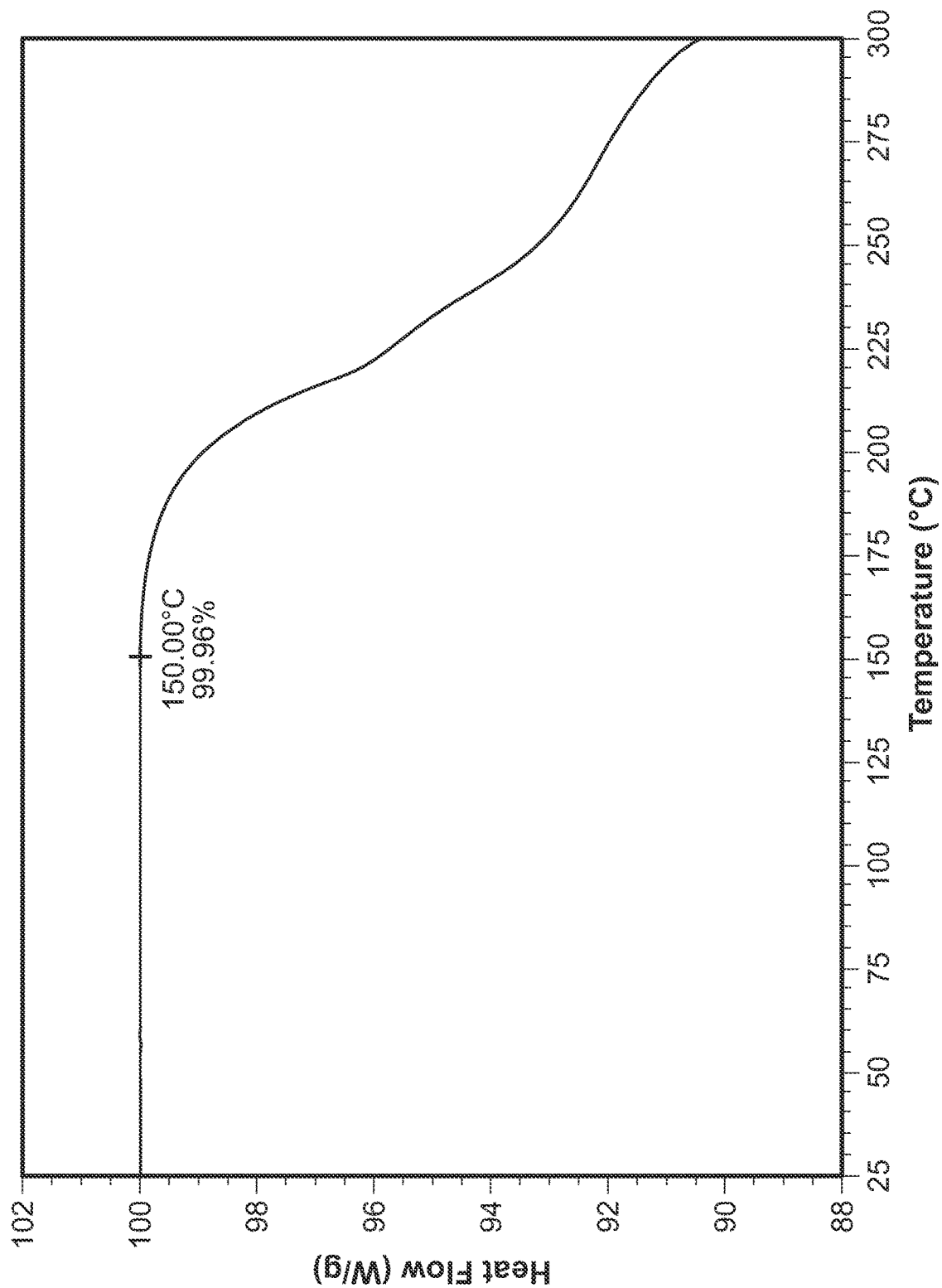
FIG. 36 illustrates the TGA thermogram of Form A that was free from volatiles with a weight loss of about 0.04% from 25° C. to 150° C.
Figure 37:
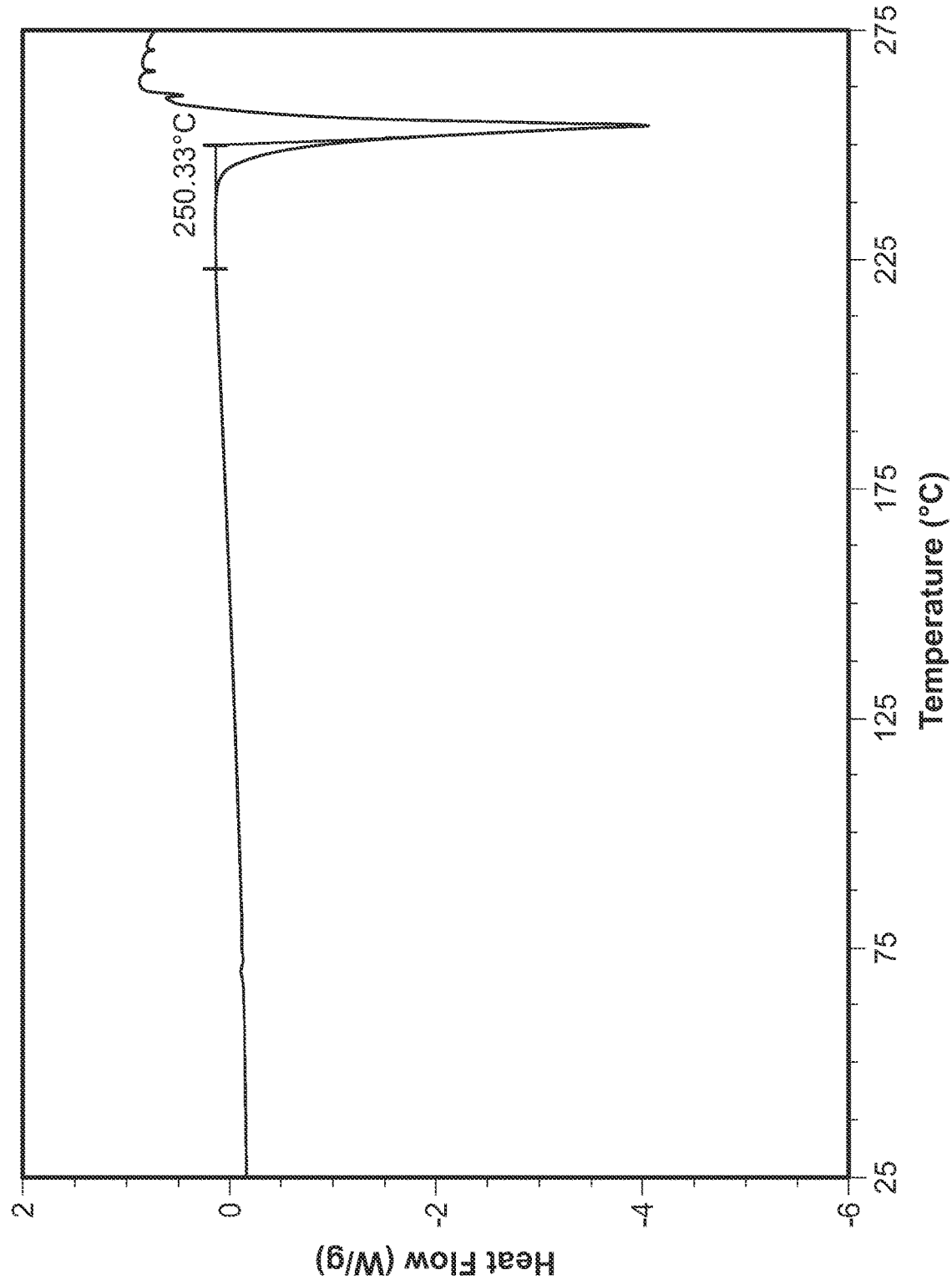
FIG. 37 illustrates the DSC thermograms of Form A exhibited a melting onset endotherm with an average onset value of approximately 250.3° C.

[2-(1H-Indol-3-yl)-1H-imidazol-4-yl](3,4,5-trimethoxyphenyl)methanone hydrochloride salt Form A (Form A) was made by recrystallization via the procedure of Panel 4 (Tables 2 and 3) in Example 3 from a 1-propanol/nitromethane binary solvent mixture. Briefly, [2-(1H-indol-3-yl)-1H-imidazol-4-yl](3,4,5-trimethoxyphenyl)methanone hydrochloride salt was dissolved in 1-propanol/nitromethane at saturating concentrations at 25° C., heated to 45-50° C. to dissolve solids, and fast evaporated under 1.5 psi of $N_2$ flow at 40° C. to produce solid Form A. Form A had an XRD pattern that indicated it had a reproducible powder pattern and was crystalline, as illustrated in FIG. 35. Form A was characterized by an XRD pattern having peaks at about 9.6, 12.0, 19.2, 23.6, and 24.4 2θ±0.2 2θ. Form A was further characterized by an XRD pattern having peaks at 16.3, 18.1, and 28.9 2θ±0.2 2θ. The TGA demonstrated that Form A was free from volatiles with a weight loss of about 0.04% from 25° C. to 150° C., as illustrated in FIG. 36. The DSC thermograms of Form A exhibited a melting onset endotherm with an average onset value of approximately 250.3° C., as illustrated in FIG. 37. These thermal events were attributed to the melt and decompose behavior of the form. The dynamic vapor sorption (DVS) plots for Form A illustrates that the material is very hydrophobic and does not appear to be prone to hydrate formation. A total weight gain of about 0.4% at 90% RH was observed (not shown).

Figure 19:
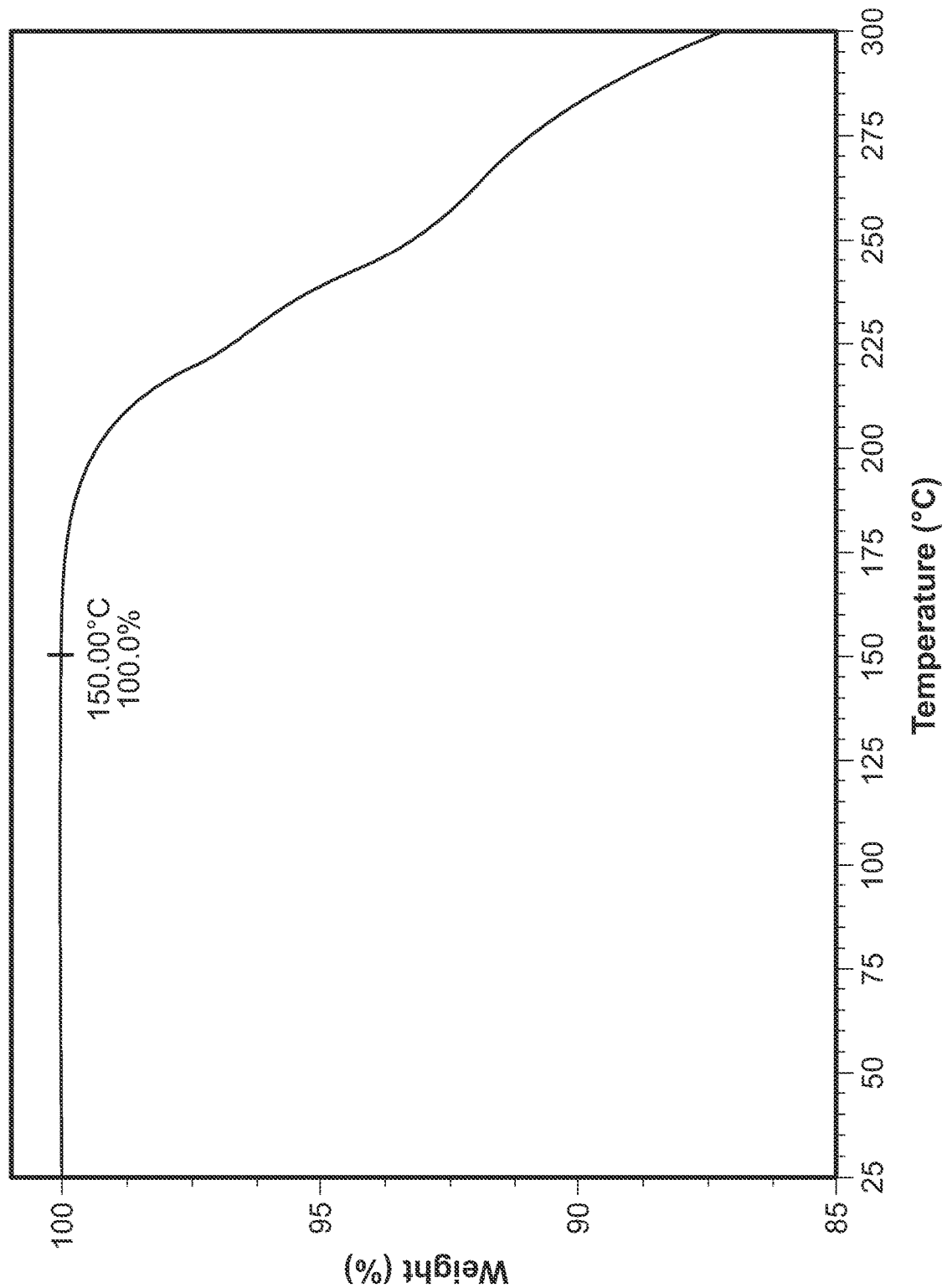
FIG. 19 illustrates the TGA thermogram of Form B that showed an average value of less than 0.05% weight loss at 150° C.
Figure 20:
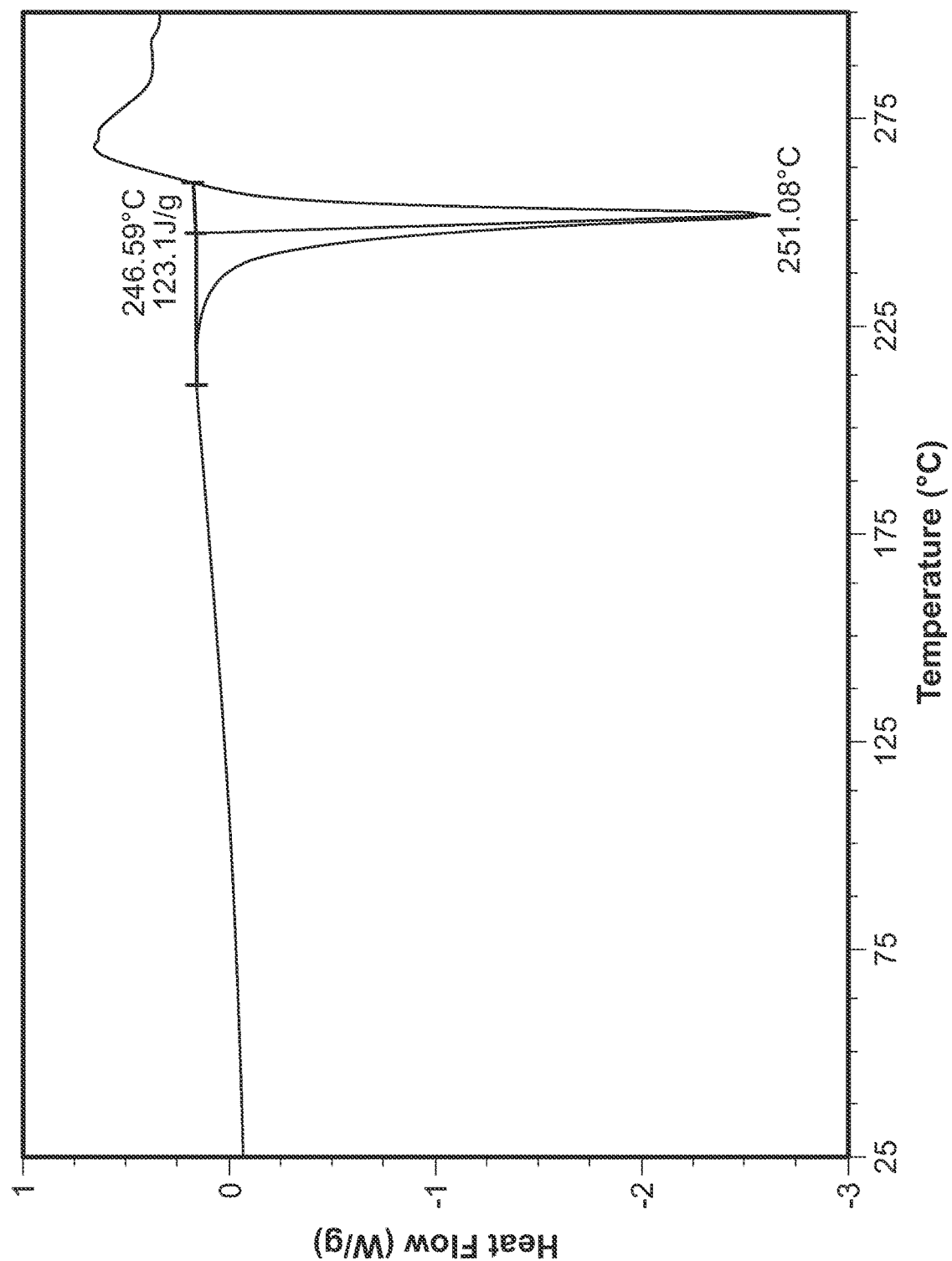
FIG. 20 illustrates the DSC thermogram of Form B that exhibited a sharp melting onset endotherm with an average onset value of approximately 247.4° C.
Figure 21:
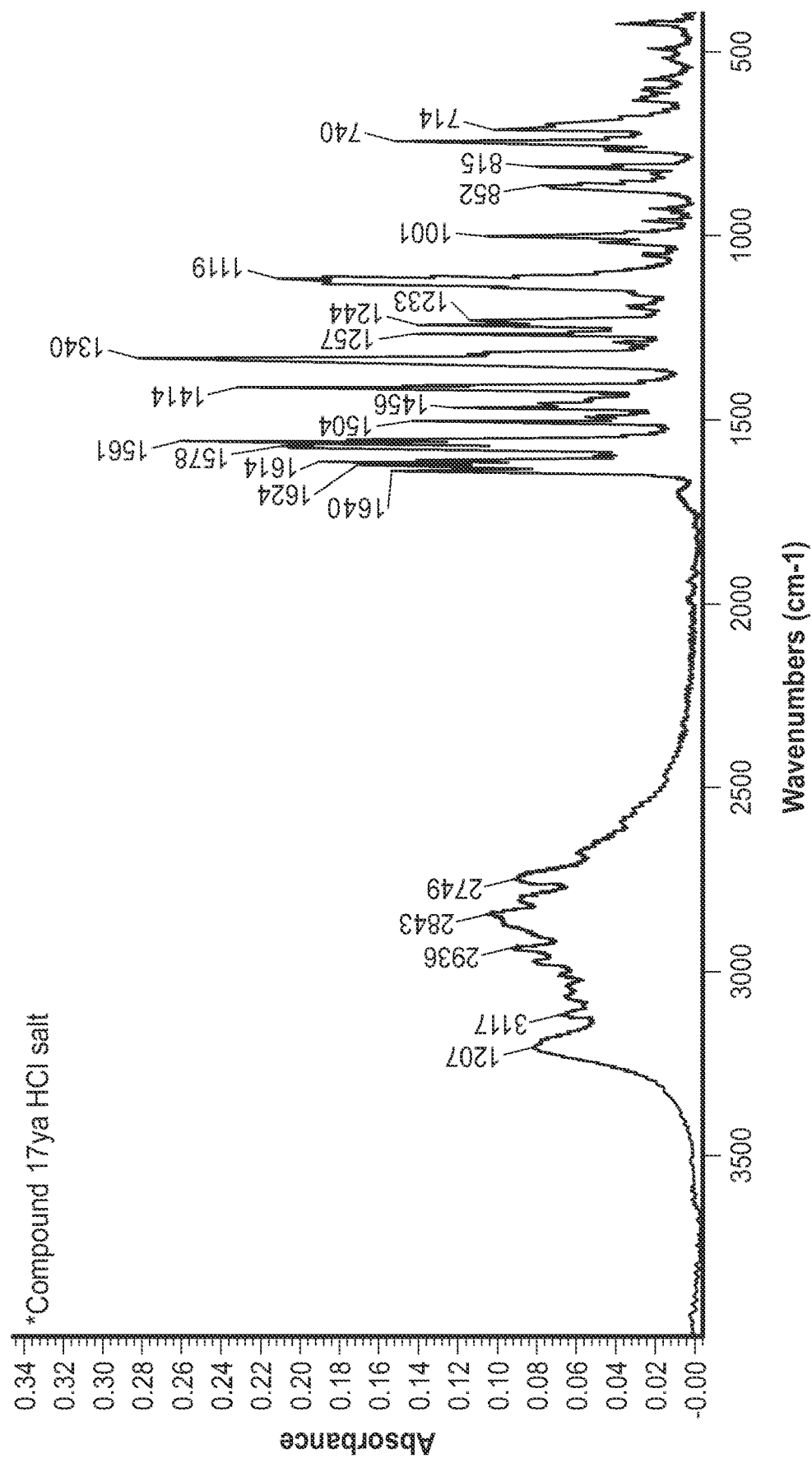
FIG. 21 illustrates the solid state Fourier transform infrared (FT-IR) spectrum of Form B.

[2-(1H-Indol-3-yl)-1H-imidazol-4-yl](3,4,5-trimethoxyphenyl)methanone hydrochloride salt Form B (Form B) was made by recrystallization via the procedure of Panel 4 (Tables 2 and 3) in Example 3 from a methanol/acetonitrile binary solvent mixture. Briefly, [2-(1H-indol-3-yl)-1H-imidazol-4-yl](3,4,5-trimethoxyphenyl)methanone hydrochloride salt was dissolved in methanol/acetonitrile at saturating concentrations at 25° C., heated to 45-50° C. in order to dissolve any solids, and fast evaporated under 1.5 psi of $N_2$ flow at 40° C. to produce Form B. Form B was stable (i.e., unchanged) in the non-competitive slurry experiments (Example 4, Tables 4 and 5) suggesting it is stable in many single solvents to include tetrahydrofuran (THF), ethyl acetate, methylene chloride, toluene, and heptane, and in trifluoroethanol (TFE)/dichloromethane (DCM) binary solvent mixture. Only in acetone or acetonitrile was Form B transformed to Form D in non-competitive slurry experiments (Table 4). Further, Form B was made by competitive slurry of Form $C_H$ and Form B in ethyl acetate as described in Table 6 (row 4) of Example 5, which speaks to the relative stability of Form $C_H$ compared to Form B. Briefly, excess of Form $C_H$ and Form B were added to neat ethyl acetate until saturated. The resulting suspension was agitated for about two weeks at ambient temperature. The solids were vacuum filtered and analyzed by XRD to determine that Form B was made. To avoid possible desolvation or physical change after isolation, the samples were not further dried before X-ray analysis. Form B had diffraction characteristics different from the other polymorphic forms. The XRD pattern of Form B indicated it had a reproducible powder pattern and was crystalline, as illustrated in FIG. 18. Form B was characterized by an XRD pattern having peaks at about 9.5, 12.1, 18.0, 18.9, and 23.0 2θ±0.2 2θ. Form B was further characterized by an XRD pattern having peaks at 19.2, 28.5, 29.5, and 31.8 2θ±0.2 2θ. The TGA thermogram demonstrated that Form B showed an average value of less than 0.05% weight loss at 150° C., as illustrated in FIG. 19. The DSC thermograms of Form B exhibited a sharp melting onset endotherm with an average onset value of approximately 247.4° C., as illustrated in FIG. 20. These thermal events were attributed to the melt and decompose behavior of the form. The solid state FT-IR spectrum of Form B is illustrated in FIG. 21. This form appeared to be a metastable form of the HCl salt.

Figure 23:
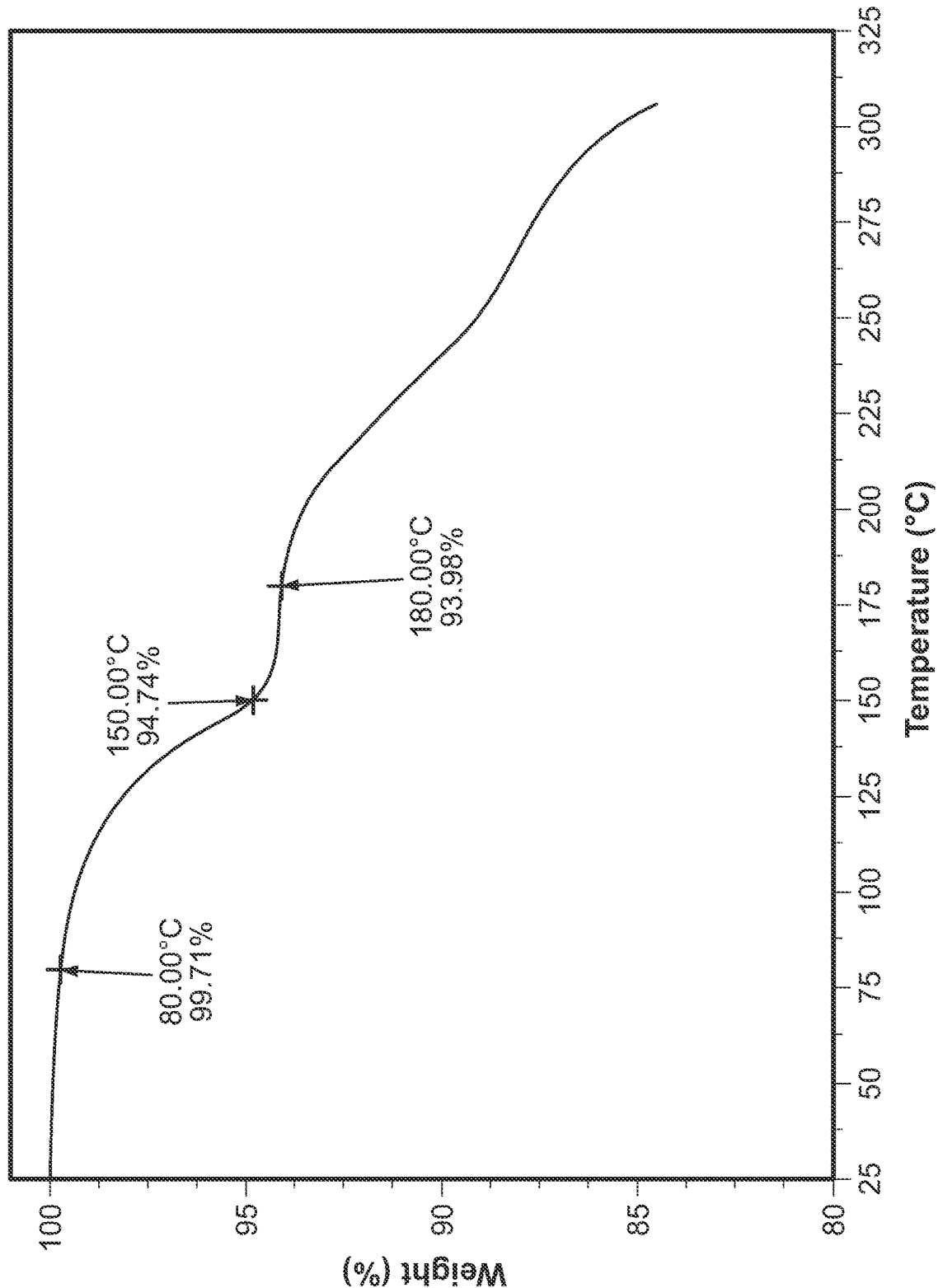
FIG. 23 illustrates the TGA thermogram of Form $C_H$.
Figure 24:
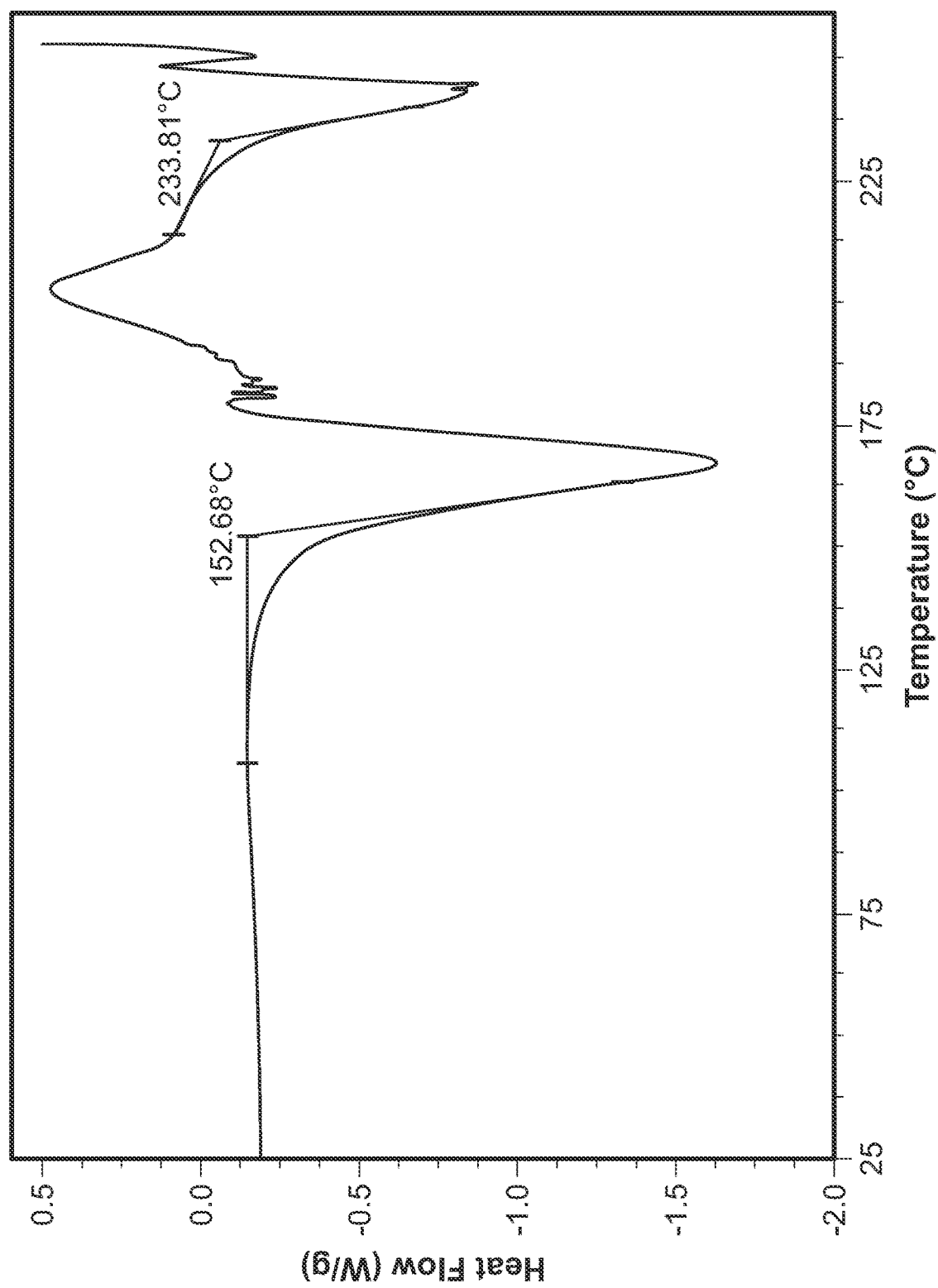
FIG. 24 illustrates the DSC thermogram of Form $C_H$.

[2-(1H-Indol-3-yl)-1H-imidazol-4-yl](3,4,5-trimethoxyphenyl)methanone hydrochloride salt Form $C_H$ was a hydrate (Form $C_H$) made in samples held at room temperature. The XRD pattern of Form $C_H$ indicated crystallinity, as illustrated in FIG. 22. Form $C_H$ was characterized by an XRD pattern having peaks at about 5.1, 13.1, 16.6, 22.5, and 25.7 2θ±0.2 2θ. Form $C_H$ was further characterized by an XRD pattern having peaks at 10.3, 18.0, 23.7, 28.7, and 29.7 2θ±0.2 2θ. The TGA demonstrated that Form $C_H$ had about 5.3% weight loss at 150° C., which was approximately equivalent to a loss of one mole of water from the crystal lattice, as illustrated in FIG. 23. The DSC thermogram of Form $C_H$ exhibited a large broad endotherm with an onset of approximately 152.7° C., which may be due to the loss of residual water. This was followed by a broad exotherm at approximately 200° C. and a broad endotherm melting extrapolated onset at 233.8° C. followed by decomposition, as illustrated in FIG. 24. The DVS scan for Form $C_H$ illustrated a moisture adsorption-desorption isotherm and the kinetic plots. [2-(1H-Indol-3-yl)-1H-imidazol-4-yl](3,4,5-trimethoxyphenyl)methanone hydrochloride salt Form $C_H$ revealed a very low uptake of water adsorption believed to be because the drying part of the DVS scan was inadequate to remove the original mole of water found in the crystalline structure (not shown). The monohydrate sample took up to 0.95 wt % at high humidity and then returned to its starting mass upon completion of the scan (not shown).

Figure 26:
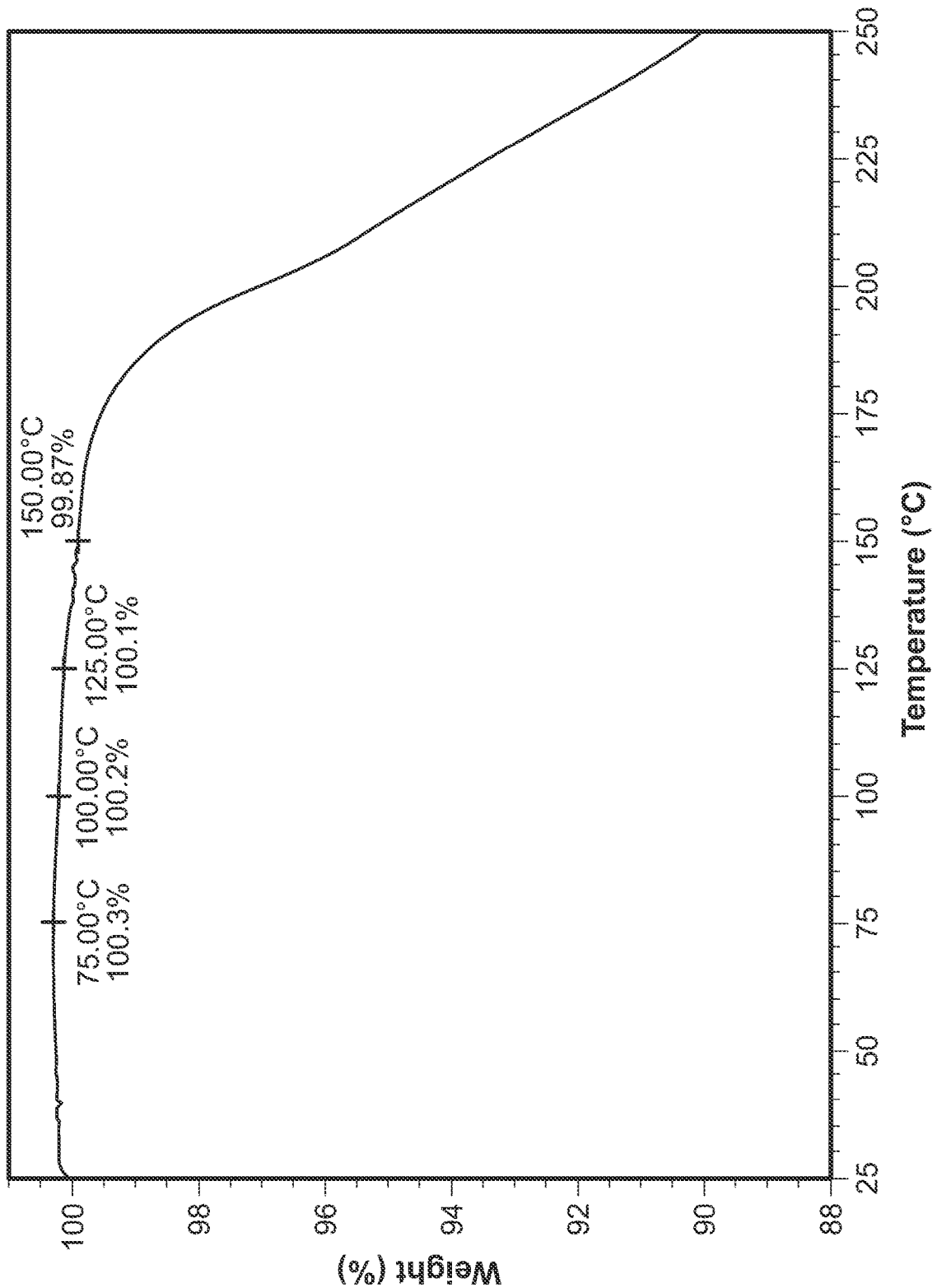
FIG. 26 illustrates the TGA thermogram of Form D.
Figure 27:
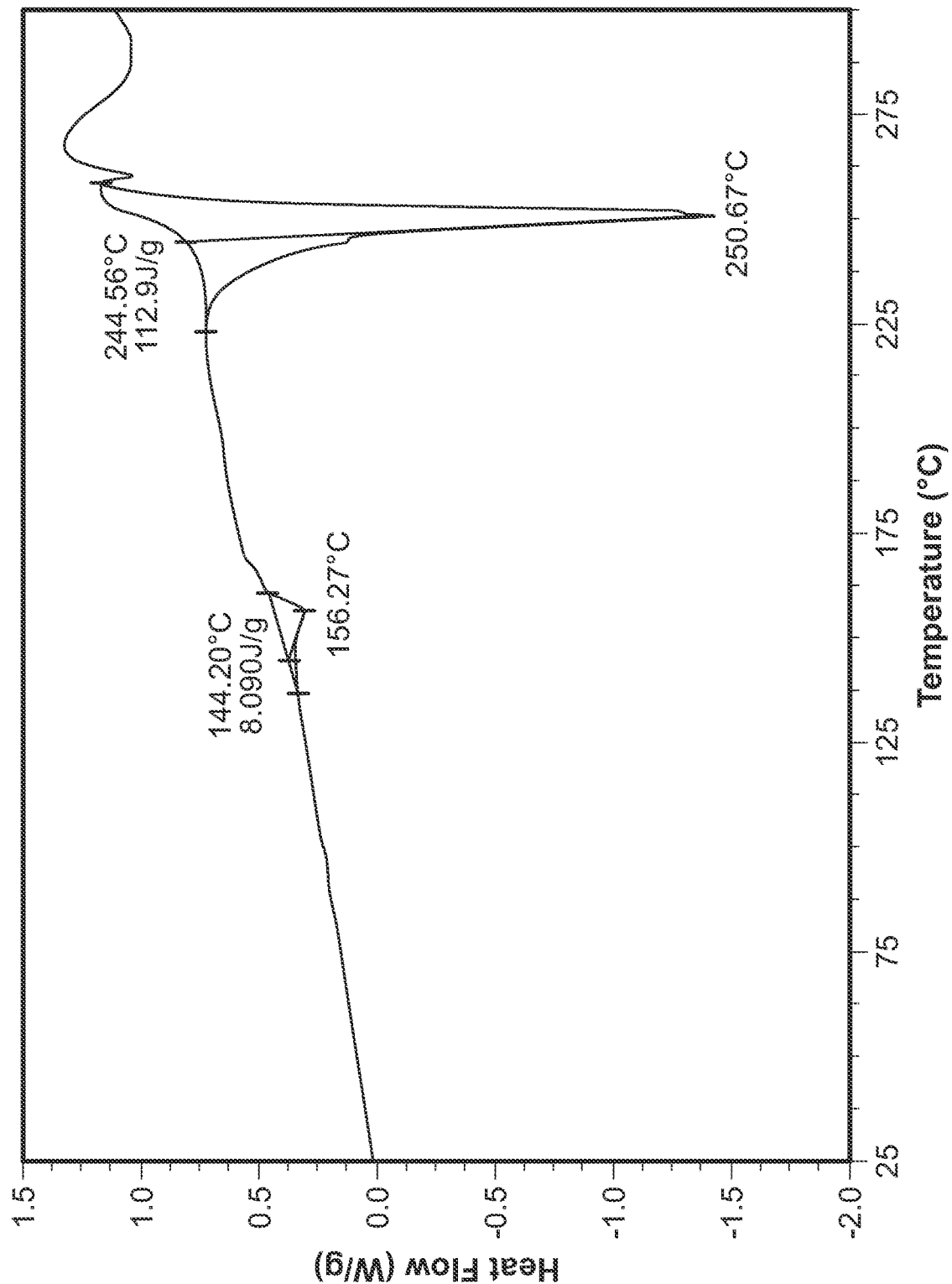
FIG. 27 illustrates the DSC thermogram of Form D.
Figure 28:
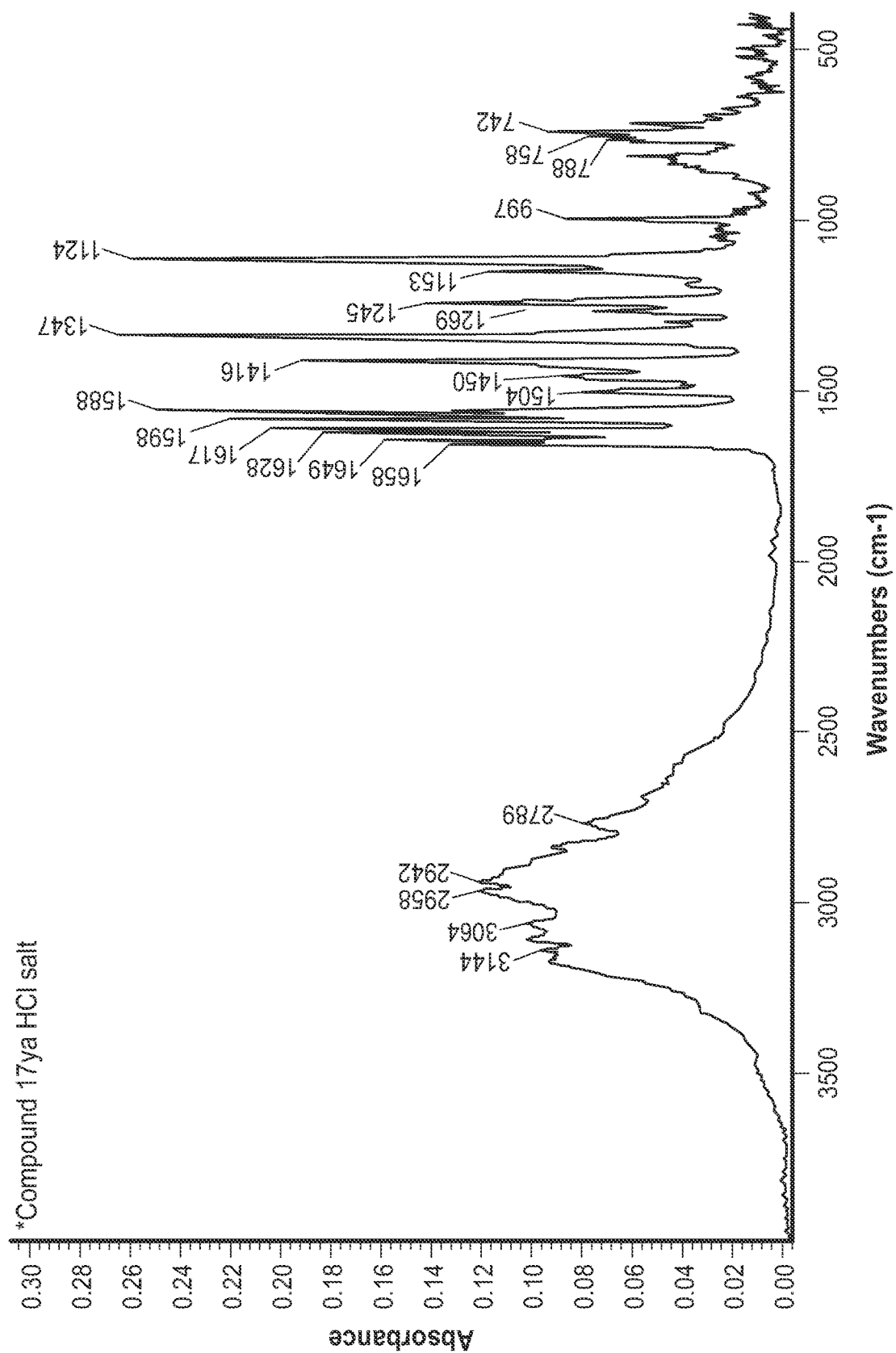
FIG. 28 illustrates the solid state FTIR spectrum for Form D.

[2-(1H-Indol-3-yl)-1H-imidazol-4-yl](3,4,5-trimethoxyphenyl)methanone hydrochloride salt Form D (Form D) was first made in the non-competitive slurries experiments in which Form B was slurried in either of the non-aqueous solvents acetone or acetonitrile for 14 days as described in Table 4 of Example 4. A process to make Form D was observed in these non-competitive slurries experiments in which Form B was slurried in the non-aqueous solvent acetone for 14 days as described in Table 4 of Example 4. Briefly, excess Form B was added to neat acetone until saturated. The resulting suspension was agitated for fourteen days at ambient temperature. The solids were vacuum filtered and analyzed by XRD to determine that Form D was made. To avoid possible desolvation or physical change after isolation, the samples were not further dried before X-ray analysis. Another process to make Form D was observed in these non-competitive slurries experiments in which Form B was slurried in the non-aqueous solvent acetonitrile for 14 days as described in Table 4 of Example 4. Briefly, excess Form B was added to neat acetonitrile until saturated. The resulting suspension was agitated for fourteen days at ambient temperature. The solids were vacuum filtered and analyzed by XRD to determine that Form D was made. To avoid possible desolvation or physical change after isolation, the samples were not further dried before X-ray analysis. These observations provide processes by which Form D of the [2-(1H-indol-3-yl)-1H-imidazol-4-yl](3,4,5-trimethoxyphenyl)methanone hydrochloride salt can be made. The data suggests that Form D was more stable than Form B in some solvent systems. The XRD pattern of Form D indicated a distinctly crystalline powder pattern, as illustrated in FIG. 25. Form D was characterized by an XRD pattern having peaks at about 9.4, 15.1, 17.3, 22.1, and 23.2 2θ±0.2 2θ. Form D was further characterized by an XRD pattern having peaks at 10.5, 18.1, 22.8, 24.8, and 30.3 2θ±0.2 2θ. The TGA thermogram indicated about 0.13 wt % loss at 150° C. and a continuous weight loss at higher temperature, as illustrated in FIG. 26. The DSC thermogram of Form D exhibited a small broad solid-solid phase transition endotherm with an onset of approximately 144.2° C., a peak temperature of about 156° C. and enthalpy of about 8.1 J/g followed by the melting endotherm with extrapolated onset at 244.6° C. and a peak temperature of 250.7° C. followed by decomposition, as illustrated in FIG. 27. The solid state FT-IR spectrum for [2-(1H-indol-3-yl)-1H-imidazol-4-yl](3,4,5-trimethoxyphenyl)methanone hydrochloride salt Form D is illustrated in FIG. 28.

[2-(1H-Indol-3-yl)-1H-imidazol-4-yl](3,4,5-trimethoxyphenyl)methanone hydrochloride salt Forms E (Form E) and E1 (Form E1) were relatively stable forms as noted by their synthesis in competitive slurries experiments starting with Form B (Table 6, Example 5). In one embodiment, Form E was made when Form B and Form D were co-incubated in 1-propanol for about 2 weeks, which speaks the relative stability of Form E relative to Form B and Form D (Table 6, row 5). Briefly, excess Form B and Form D were added to neat 1-propanol until saturated. The resulting suspension was agitated for about two weeks at ambient temperature. The solids were vacuum filtered and analyzed by XRD to determine that Form E was made. To avoid possible desolvation or physical change after isolation, the samples were not further dried before X-ray analysis. In another embodiment, Form E was made when Form A and Form B were co-incubated in 1-propanol for about 2 weeks (Table 6, row 9). Briefly, excess of Form A and Form B were added to neat 1-propanol until saturated. The resulting suspension was agitated for about two weeks at ambient temperature. The solids were vacuum filtered and analyzed by XRD to determine that Form E was made. To avoid possible desolvation or physical change after isolation, the samples were not further dried before X-ray analysis. Cumulatively, this data suggested that Form E was relatively stable as compared to Form A, Form B, and Form D. This is consistent with data from the recrystallization experiments where Form E (and Form E1) resulted from multiple solvent systems.

Form E was also made by three different recrystallization processes including 2-propanol, 1-propanol/1-dioxane mixture, or ethanol. In one embodiment, Form E was made by recrystallization via the procedure of Panel 1 (Tables 2 and 3) in Example 3) from 2-propanol. Briefly, [2-(1H-indol-3-yl)-1H-imidazol-4-yl](3,4,5-trimethoxyphenyl)methanone hydrochloride salt was dissolved in 2-propanol at saturating concentrations at 25° C., heated to 45-50° C. to dissolve the solids, and fast evaporated under 1.5 psi of $N_2$ flow at ambient temperature to produce Form E. In another embodiment, Form E was made by recrystallization via the procedure of Panel 3 (Tables 2 and 3) in Example 3) from 1-propanol/dioxane binary solvent mixture. Briefly, [2-(1H-indol-3-yl)-1H-imidazol-4-yl](3,4,5-trimethoxyphenyl)methanone hydrochloride salt was dissolved in 1-propanol/dioxane at saturating concentrations at 25° C., and solvent was slowly evaporated at ambient temperature to make Form E. In another embodiment, Form E was made by recrystallization via the procedure of Panel 4 (Tables 2 and 3) in Example 3 from ethanol. Briefly, [2-(1H-indol-3-yl)-1H-imidazol-4-yl](3,4,5-trimethoxyphenyl)methanone hydrochloride salt was dissolved in ethanol at saturating concentrations at 25° C., heated to 45-50° C. to dissolve any solids, and solvent was fast evaporated under 1.5 psi of $N_2$ flow at 40° C. to make Form E.

Form E1 only differed slightly from Form E in a few peaks in the in the 10-12° 2θ region of their XRD patterns suggesting very similar physical properties. In overview, Form E1 was relatively stable compared to Form A, Form B, Form $C_H$, Form D, and Form E as attested to by the results of non-competitive (Form B only) and competitive (all forms) slurry experiments.

Form E1 was made by two different recrystallization processes from 2-propanol/dichloromethane and 2-propanol/trichloromethane. In one embodiment, Form E1 was made by recrystallization via the procedure of Panel 4 (Tables 2 and 3) in Example 3 from 2-propanol/dichloromethane binary solvent mixture. Briefly, [2-(1H-indol-3-yl)-1H-imidazol-4-yl](3,4,5-trimethoxyphenyl)methanone hydrochloride salt was dissolved in 2-propanol/dichloromethane at saturating concentrations at 25° C., heated to 45-50° C. to dissolve the solids, and fast evaporated under 1.5 psi of $N_2$ flow at 40° C. to make Form E1. In another embodiment, Form E1 was made by recrystallization via the procedure of Panel 4 (Tables 2 and 3) in Example 3 from 2-propanol/trichloromethane binary solvent mixture. Briefly, [2-(1H-indol-3-yl)-1H-imidazol-4-yl](3,4,5-trimethoxyphenyl)methanone hydrochloride salt was dissolved in 2-propanol/trichloromethane at saturating concentrations at 25° C., heated to 45-50° C. to dissolve solids, and fast evaporated under 1.5 psi of $N_2$ flow at 40° C. to make Form E1.

Form E1 was made from non-competitive slurry experiments starting from Form B incubated in five distinct binary solvent systems (see Table 5 at rows 3, 5, and 7-9 of Example 4). In one embodiment, Form E1 was made by non-competitive slurries experiments in which Form B was slurried in the non-aqueous binary solvent system of ethanol/toluene for 11 days. Briefly, excess Form B was added to an ethanol/toluene mixture until saturated. The resulting suspension was agitated for eleven days at ambient temperature. The solids were vacuum filtered and analyzed by XRD to determine that Form E1 was made. To avoid possible desolvation or physical change after isolation, the samples were not further dried before X-ray analysis. In another embodiment, Form E1 was made by non-competitive slurries experiments in which Form B was slurried in the non-aqueous binary solvent system of acetonitrile (ACN)/acetone for 11 days. Briefly, excess Form B was added to an acetonitrile (ACN)/acetone mixture until saturated. The resulting suspension was agitated for eleven days at ambient temperature. The solids were vacuum filtered and analyzed by XRD to determine that Form E1 was made. To avoid possible desolvation or physical change after isolation, the samples were not further dried before X-ray analysis. In another embodiment, Form E1 was made by non-competitive slurries experiments in which Form B was slurried in a non-aqueous binary solvent system of ethanol/acetonitrile for 11 days. Briefly, excess Form B was added to an ethanol/acetonitrile mixture until saturated. The resulting suspension was agitated for eleven days at ambient temperature. The solids were vacuum filtered and analyzed by XRD to determine that Form E1 was made. To avoid possible desolvation or physical change after isolation, the samples were not further dried before X-ray analysis. In another embodiment, Form E1 was made by non-competitive slurries experiments in which Form B was slurried in the non-aqueous binary solvent system of 1-propanol/ethyl acetate (EtOAc) for 11 days. Briefly, excess Form B was added to a 1-propanol/ethyl acetate (EtOAc) mixture until saturated. The resulting suspension was agitated for eleven days at ambient temperature. The solids were vacuum filtered and analyzed by XRD to determine that Form E1 was made. To avoid possible desolvation or physical change after isolation, the samples were not further dried before X-ray analysis. In another embodiment, Form E1 was made by non-competitive slurries experiments in which Form B was slurried in the non-aqueous binary solvent system of 2-propanol/tetrahydrofuran (THF) for 11 days. Briefly, excess Form B was added to a 2-propanol/tetrahydrofuran (THF) mixture until saturated. The resulting suspension was agitated for eleven days at ambient temperature. The solids were vacuum filtered and analyzed by XRD to determine that Form E1 was made. To avoid possible desolvation or physical change after isolation, the samples were not further dried before X-ray analysis. These data in Example 4 demonstrated that Form E1 was more stable than Form B in many binary solvent systems, and supports Form E1 as a relatively stable polymorph of the [2-(1H-indol-3-yl)-1H-imidazol-4-yl](3,4,5-trimethoxyphenyl)methanone hydrochloride salt compared to Form B.

Form E1 was also made from four different competitive slurry experiments as described in Table 6 at rows 7 and 10-12 in Example 5 involving binary combinations of Form A, Form B, Form $C_H$, Form D, and Form E that were co-incubated in 1-propanol for about two weeks. This data demonstrated the increased stability of Form E1 relative to these other forms. In one embodiment, Form E1 was made when Form $C_H$ and Form B were co-incubated in 1-propanol for about 2 weeks (Table 6, row 7). Briefly, excess Form $C_H$ and Form B were added to neat 1-propanol until saturated. The resulting suspension was agitated for about two weeks at ambient temperature. The solids were vacuum filtered and analyzed by XRD to determine that Form E1 was made. To avoid possible desolvation or physical change after isolation, the samples were not further dried before X-ray analysis. In another embodiment, Form E1 was made when Form A and Form D were co-incubated in 1-propanol for about 2 weeks (Table 6, row 10). Briefly, excess Form A and Form D were added to neat 1-propanol until saturated. The resulting suspension was agitated for about two weeks at ambient temperature. The solids were vacuum filtered and analyzed by XRD to determine that Form E1 was made. To avoid possible desolvation or physical change after isolation, the samples were not further dried before X-ray analysis. In another embodiment, Form E1 was made when Form B and Form E were co-incubated in 1-propanol for about 2 weeks (Table 6, row 11). Briefly, excess Form B and Form E were added to neat 1-propanol until saturated. The resulting suspension was agitated for about two weeks at ambient temperature. The solids were vacuum filtered and analyzed by XRD to determine that Form E1 was made. To avoid possible desolvation or physical change after isolation, the samples were not further dried before X-ray analysis. In another embodiment, Form E1 was made when Form D and Form E were co-incubated in 1-propanol for about 2 weeks (Table 6, row 12). Briefly, excess Form D and Form E were added to neat 1-propanol until saturated. The resulting suspension was agitated for about two weeks at ambient temperature. The solids were vacuum filtered and analyzed by XRD to determine that Form E1 was made. To avoid possible desolvation or physical change after isolation, the samples were not further dried before X-ray analysis. In some embodiments, Form E and Form E1 are discussed together as apparently stable polymorphs. Data in this example may be interpreted as Form E1 having greater stability than Form E, but their physical characteristics are expected to be approximately similar. No data support either Form E or Form E1 as more stable than Form H which is believed to be the most stable polymorph.

Figure 31:
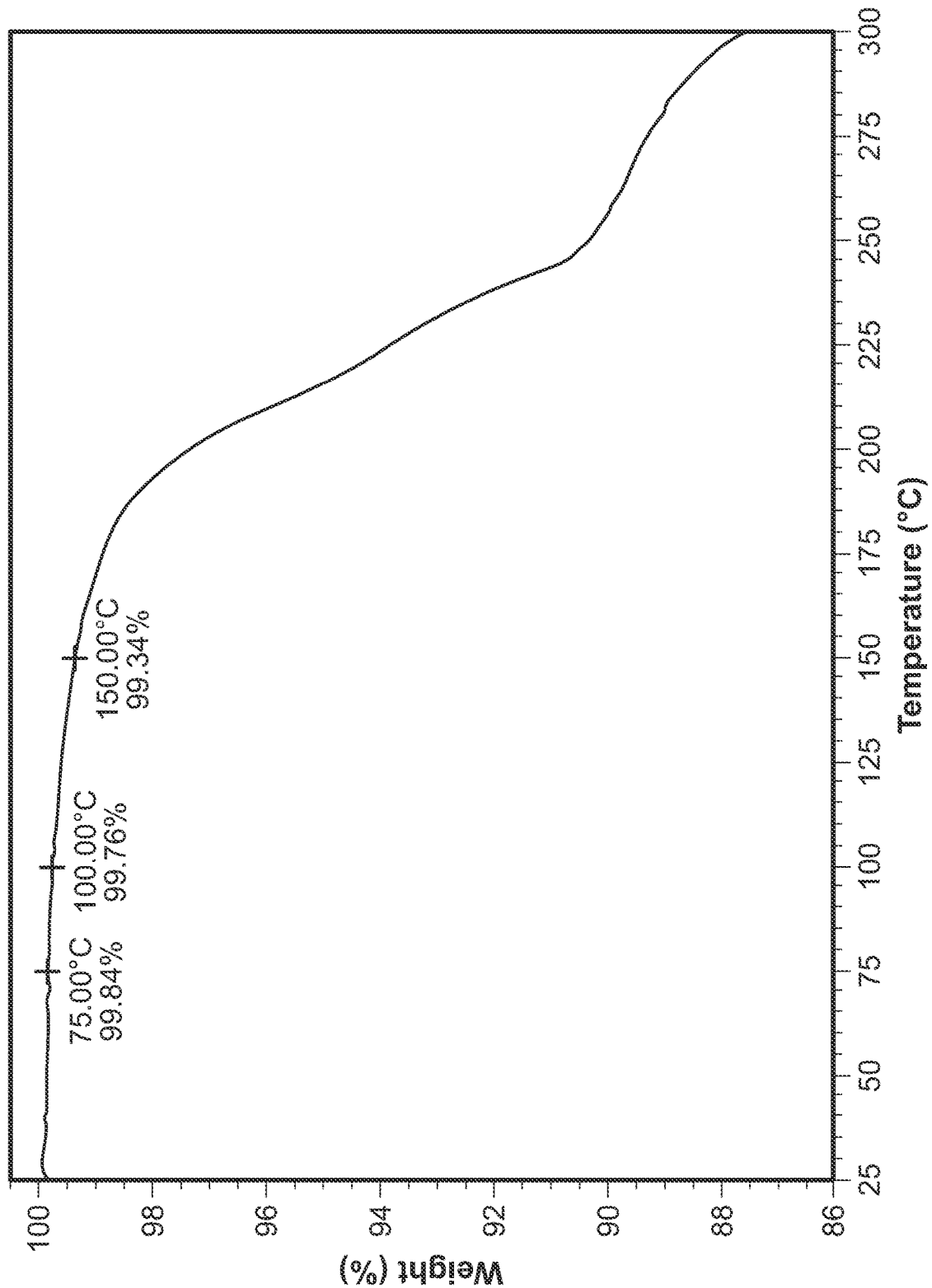
FIG. 31 illustrates the TGA thermogram of Form E that exhibited approximately 0.66% weight loss at 150° C.
Figure 33:
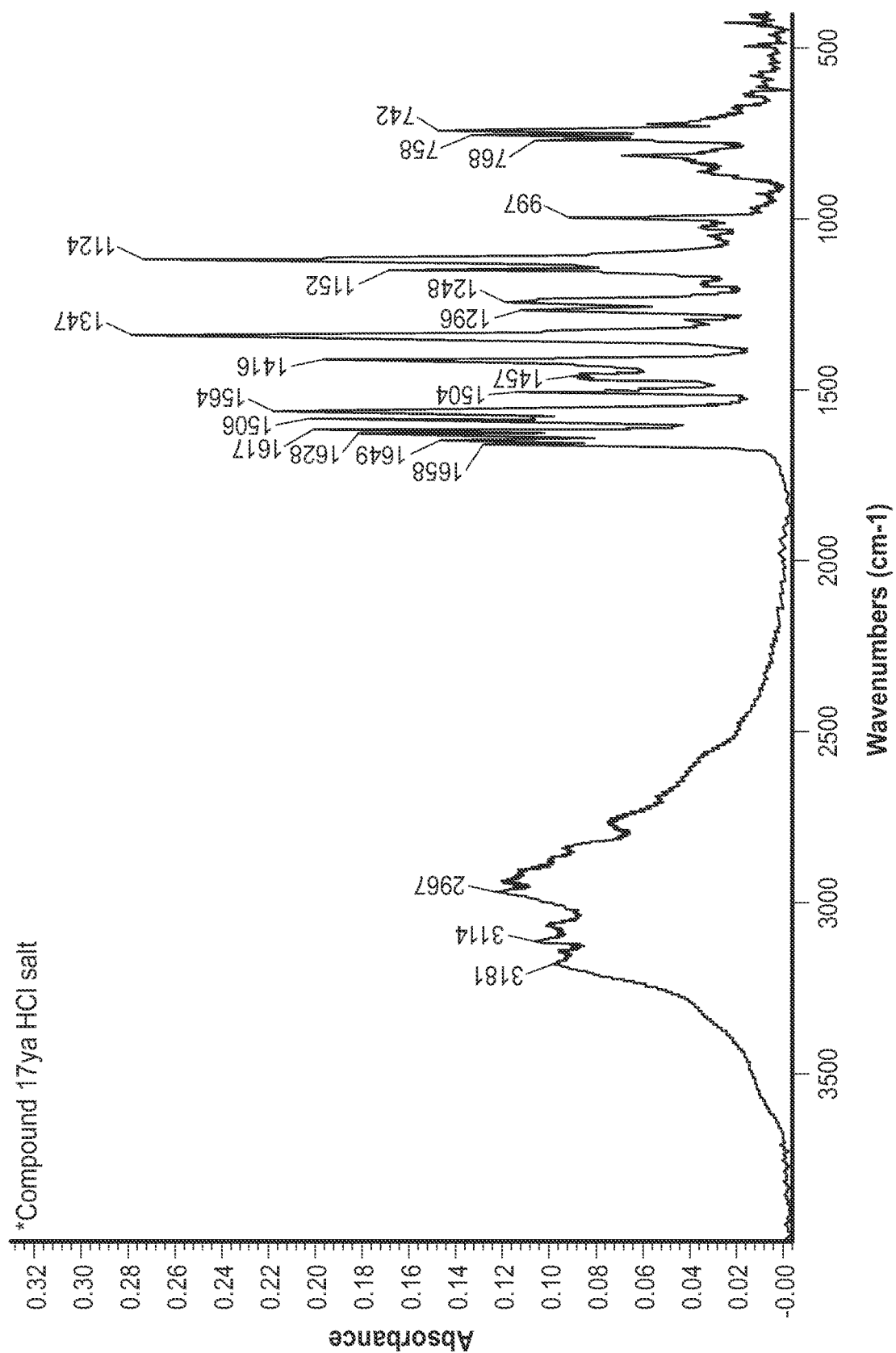
FIG. 33 illustrates the solid state FTIR spectrum of Form E.

The XRD patterns for [2-(1H-indol-3-yl)-1H-imidazol-4-yl](3,4,5-trimethoxyphenyl)methanone hydrochloride salt Form E and E1 demonstrated crystallinity and are illustrated in FIG. 29 and FIG. 30, respectively. The two diffraction patterns appear to be very similar except for minor differences between the two patterns in the 10-12° 2θ region. Form E was characterized by an XRD pattern having peaks at about 9.4, 17.3, 22.1, 23.4, and 24.8 2θ±0.2 2θ. Form E was further characterized by an XRD pattern having peaks at 12.9, 15.0, 18.1, 21.0, and 30.3 2θ±0.2 2θ. Form E1 was characterized by an XRD pattern having peaks at about 9.4, 10.9, 17.3, 22.1, and 23.2 2θ±0.2 2θ. Form E1 was further characterized by an XRD pattern having peaks at 13.0, 15.1, 18.1, 20.9, and 24.8 2θ±0.2 2θ. The TGA thermogram of Form E exhibited approximately 0.66% weight loss at 150° C., as illustrated in FIG. 31. The DSC thermogram of Form E exhibited a melting onset endotherm at approximately 239.6° C. immediately followed by a large, broad decomposition as illustrated in FIG. 32. The solid state FT-IR spectrum of Form E is illustrated in FIG. 33. The DSC thermogram of Form E1 exhibited a melting onset endotherm at approximately 243.2° C. immediately followed by a large, broad decomposition with unstable baseline, as illustrated in FIG. 34. The slightly higher temperature endotherm for Form E1 relative to Form E also suggests slightly more stability for Form E1, consistent with the slurry experiments described above.

[2-(1H-Indol-3-yl)-1H-imidazol-4-yl](3,4,5-trimethoxyphenyl)methanone hydrochloride salt Form $F_H$ (Form $F_H$) had diffraction characteristics different from the other polymorphic forms and was made in sample held at room temperature. Form $F_H$ was not observed in the polymorph screening efforts. Form $F_H$ had an XRD pattern that indicated it had a reproducible powder pattern, was crystalline, and was a hydrate, as illustrated in FIG. 38. Form $F_H$ was characterized by an XRD pattern having peaks at about 9.06, 10.4, 18.85, 25.48, and 27.97 2θ±0.2 2θ. Form $F_H$ was further characterized by an XRD pattern having peaks at 12.9, 20.9, and 26.14 2θ±0.2 2θ. The DSC thermogram of Form $F_H$ exhibited a large split endotherm with an onset of approximately 90.8° C. and peak maxima of 99.7° C. The KF moisture content of Form $F_H$ was 14% weight (not shown). The solution NMR spectrum of Form $F_H$ was consistent with the expected structure of the [2-(1H-indol-3-yl)-1H-imidazol-4-yl](3,4,5-trimethoxyphenyl)methanone hydrochloride salt (not shown).

Figure 41:
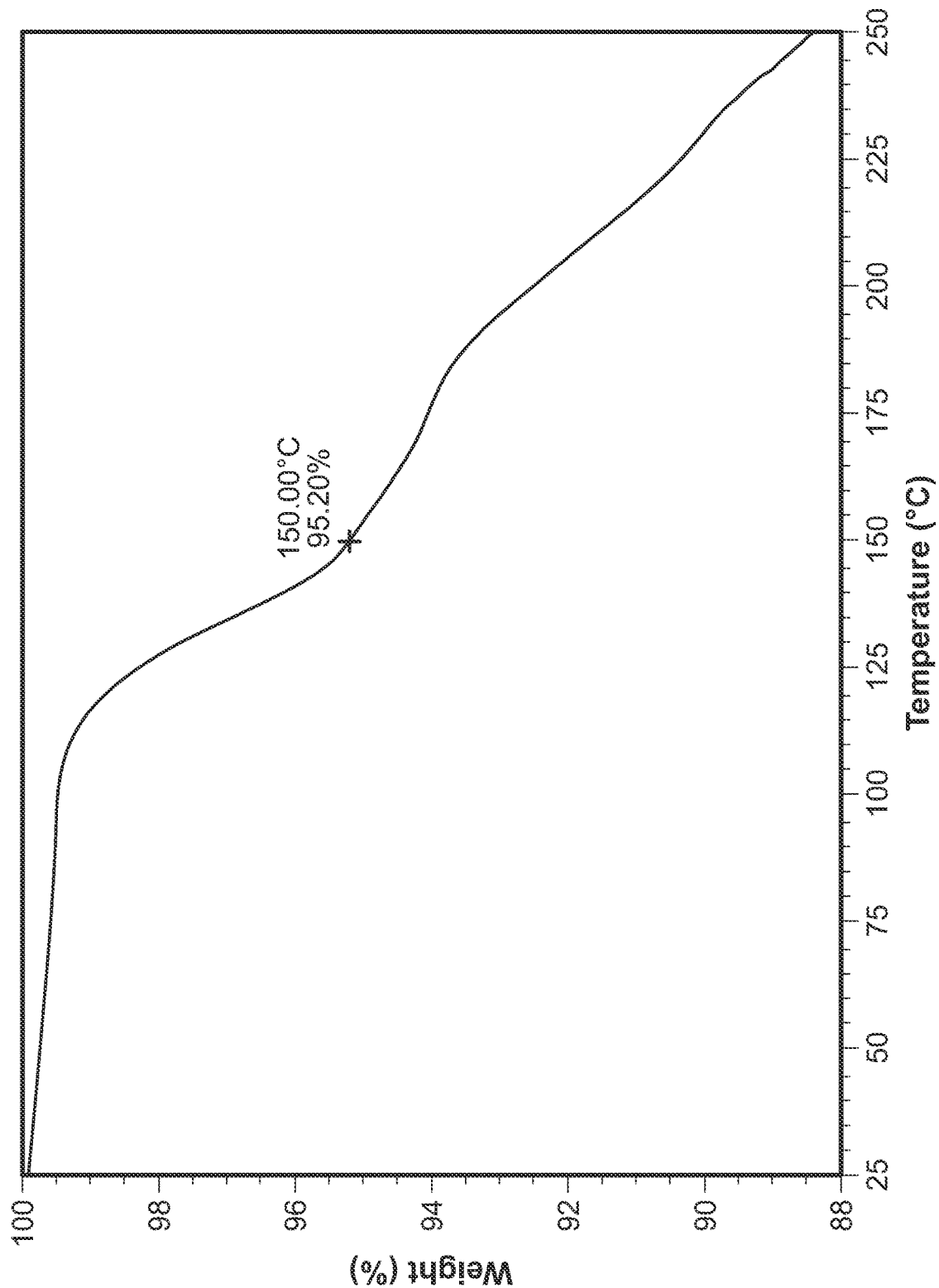
FIG. 41 illustrates the TGA thermogram of Form $G_H$.
Figure 42:
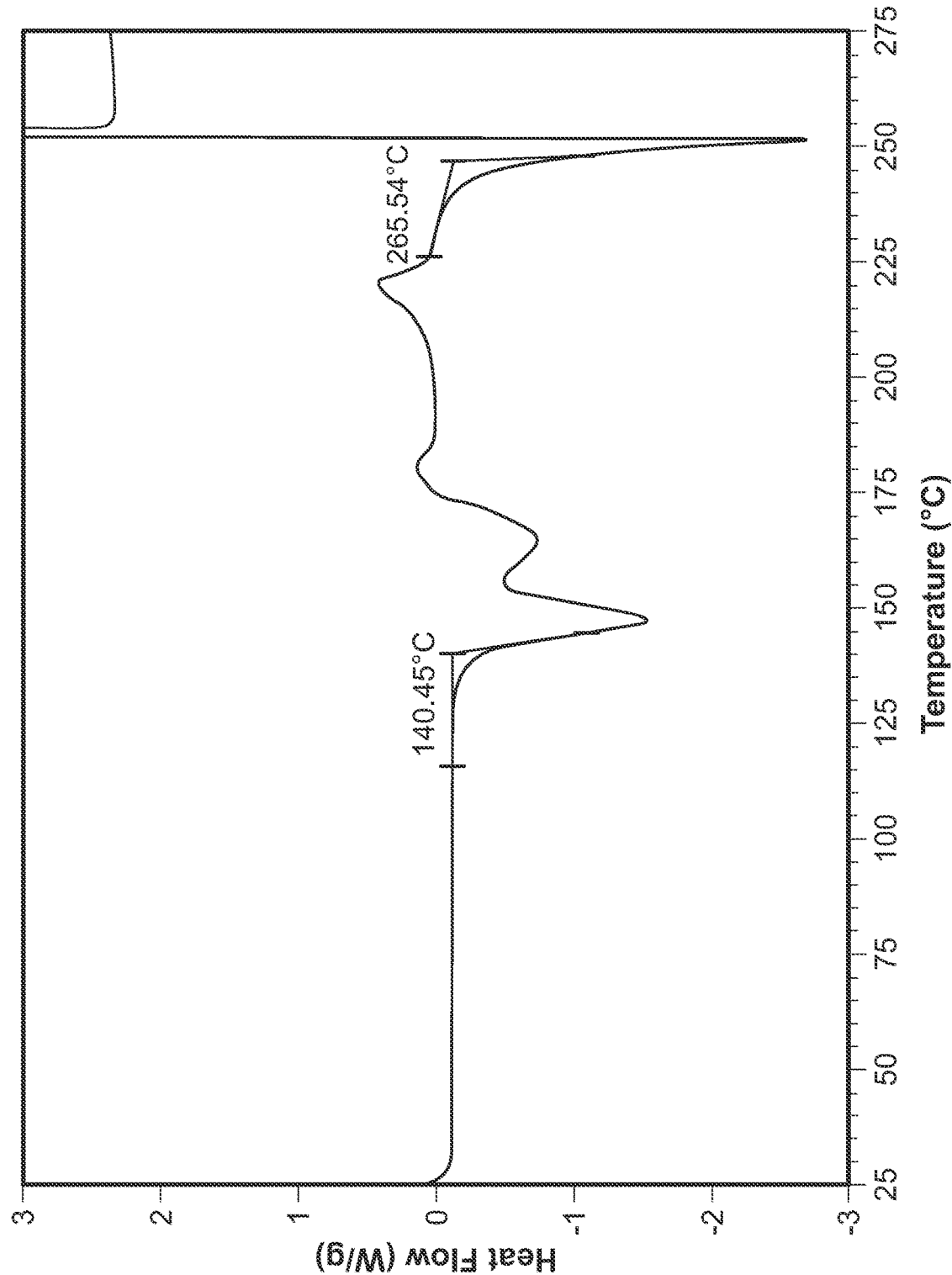
FIG. 42 illustrates the DSC thermogram of Form $G_H$.

[2-(1H-Indol-3-yl)-1H-imidazol-4-yl](3,4,5-trimethoxyphenyl)methanone hydrochloride salt Form $G_H$ (Form $G_H$) had diffraction characteristics different from the other polymorphic forms was made in samples held at room temperature, and was designated as a hydrate. The XRD pattern of Form $G_H$ indicated it had a reproducible powder pattern and was moderately crystalline, as illustrated in FIG. 40. Form $G_H$ was characterized by an XRD pattern having peaks at about 11.8, 14.5, 16.8, 23.1, and 28.5 2θ±0.2 2θ. Form $G_H$ was further characterized by an XRD pattern having peaks at 10.4, 22.3, 24.7, and 25.3 2θ±0.2 2θ. The TGA thermogram demonstrated that Form $G_H$ showed an average value of 4.8% weight loss at 150° C., as illustrated in FIG. 41. The DSC thermograms of Form $G_H$ exhibited two endotherms with extrapolated onsets of 140.5° C. and 246.5° C., as illustrated in FIG. 42. The KF moisture content of Form $G_H$ was 4.4% weight (not shown).

Figure 44:
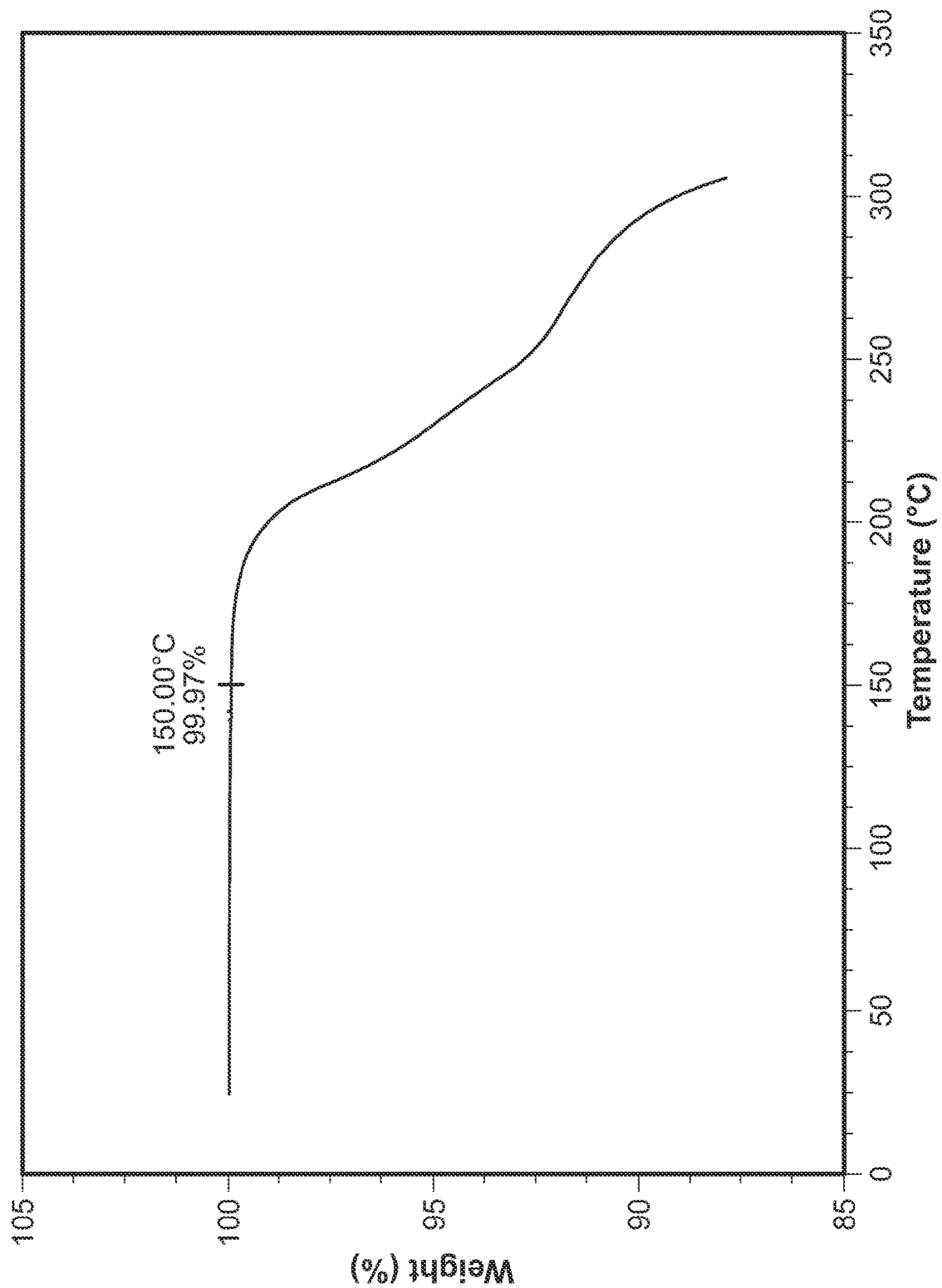
FIG. 44 illustrates the TGA thermogram of [2-(1H-indol-3-yl)-1H-imidazol-4-yl](3,4,5-trimethoxyphenyl)methanone hydrochloride salt of Form H.
Figure 45:
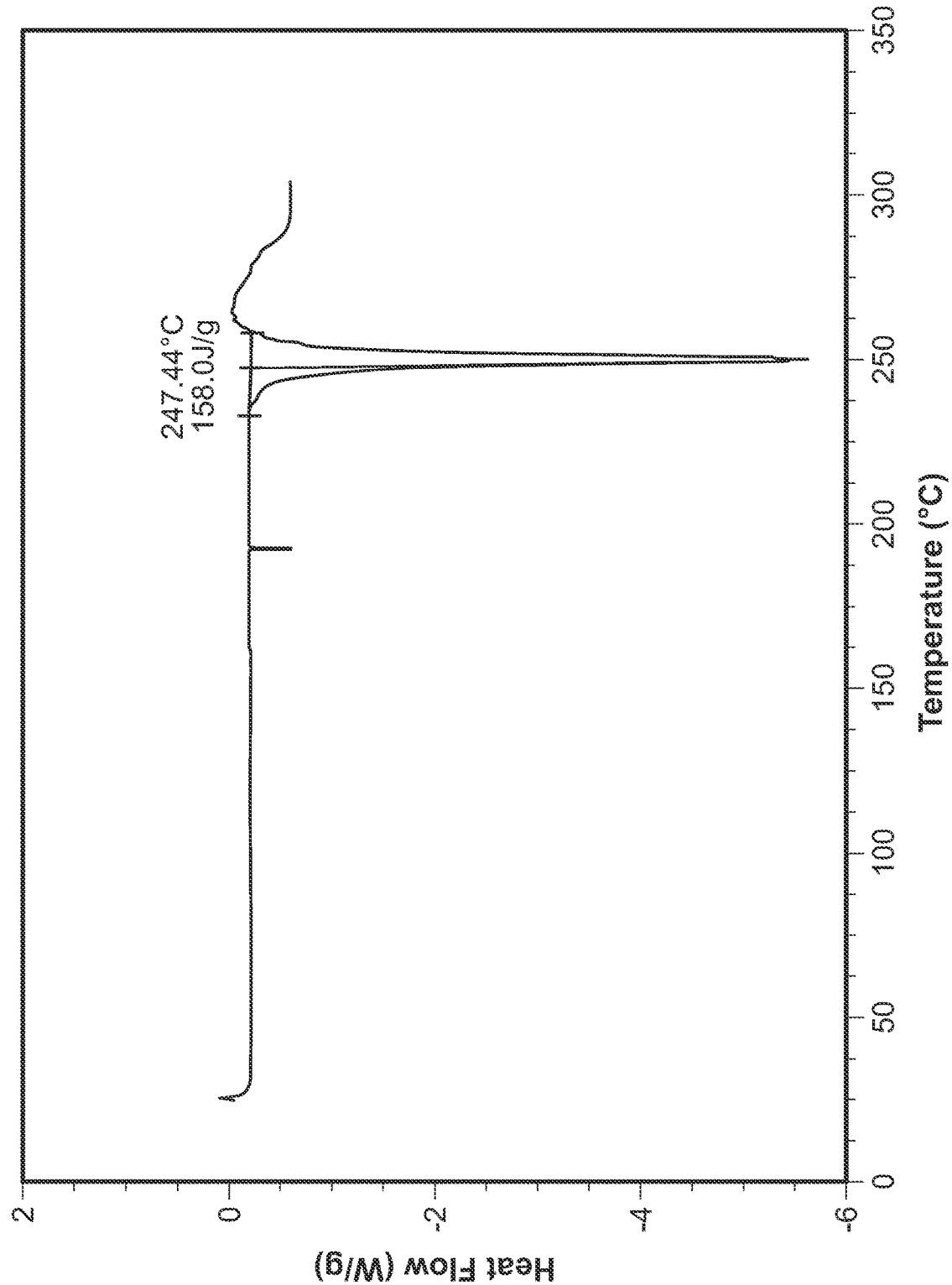
FIG. 45 illustrates the DSC thermogram of Form H.

[2-(1H-Indol-3-yl)-1H-imidazol-4-yl](3,4,5-trimethoxyphenyl)methanone hydrochloride salt Form H (Form H) was made in samples of Form E and Form E1 held at ambient conditions and was designated as a dry polymorphic form. Form H also was made by competitive slurry of Form E and Form H in 2-butanol or 2-propanol for 1 day (Table 6, row 13 and 14 of Example 5) suggesting that Form H is relatively stable compared to Form E. In one embodiment, Form H was made when Form E and Form H were co-incubated in 2-propanol for 1 day (Table 6, row 13). Briefly, excess Form E and Form H were added to neat 2-propanol until saturated. The resulting suspension was agitated for 1 day at ambient temperature. The solids were vacuum filtered and analyzed by XRD to determine that Form H was made. To avoid possible desolvation or physical change after isolation, the samples were not further dried before X-ray analysis. In another embodiment, Form H was made when Form E and Form H were co-incubated in 2-butanol for 1 day (Table 6, row 14). Briefly, excess Form E and Form H were added to neat 2-butanol until saturated. The resulting suspension was agitated for 1 day at ambient temperature. The solids were vacuum filtered and analyzed by XRD to determine that Form H was made. To avoid possible desolvation or physical change after isolation, the samples were not further dried before X-ray analysis. From the initial competitive slurry experiments (all samples except for the last two in Table 6) it appeared that Form E or Form E1 were the most stable form observed during the study. However, competitive slurries of Forms E and H in two different solvents showed that Form H was more stable than Form E. Based on these slurry experiments, large scale crystal seeding (Example 7), and DSC thermograms, Form H is expected to be the thermodynamically stable form. The XRD pattern of Form H indicated a crystalline powder pattern, as illustrated in FIG. 43. The XRD pattern of Form H indicates it was highly crystalline. Form H was characterized by an XRD pattern having peaks at about 11.8, 20.1, 23.6, 25.0, and 26.5 2θ±0.2 2θ. Form H was further characterized by an XRD pattern having peaks at 8.6, 12.5, 18.6, 21.2, and 28.1 2θ±0.2 2θ. The TGA thermogram indicated about 0.03 wt % loss at 150° C., as illustrated in FIG. 44. The DSC thermogram of Form H exhibited a melting onset endotherm with an onset of 247.5° C. with a peak maximum of 250.1° C. and an enthalpy of fusion of 158.0 J/g, as illustrated in FIG. 45. The KF moisture content of Form H was 0.21 wt % (not shown). The solution NMR spectrum of Form H is consistent with the expected structure of the [2-(1H-indol-3-yl)-1H-imidazol-4-yl](3,4,5-trimethoxyphenyl)methanone hydrochloride salt (not shown).

[2-(1H-Indol-3-yl)-1H-imidazol-4-yl](3,4,5-trimethoxyphenyl)methanone hydrochloride salt Form I (Form I) was made after slurrying in 1:1 ethanol/ethyl acetate (EtOH/EtOAc). Form I converted to a mixture of Form $C_H$ and Form H after a month of storage at ambient conditions, suggesting it is a relatively unstable polymorph. The XRD diffraction pattern for Form I is illustrated in FIG. 46. Form I of the HCl salt was characterized by an XRD pattern having peaks at about 10.0, 10.6, 16.6, 23.7, and 25.7 2θ±0.2 2θ. Form I was further characterized by an XRD pattern having peaks at 11.8, 15.9, 26.7, and 27.6 2θ±0.2 2θ as depicted in FIG. 46.

Figure 47:
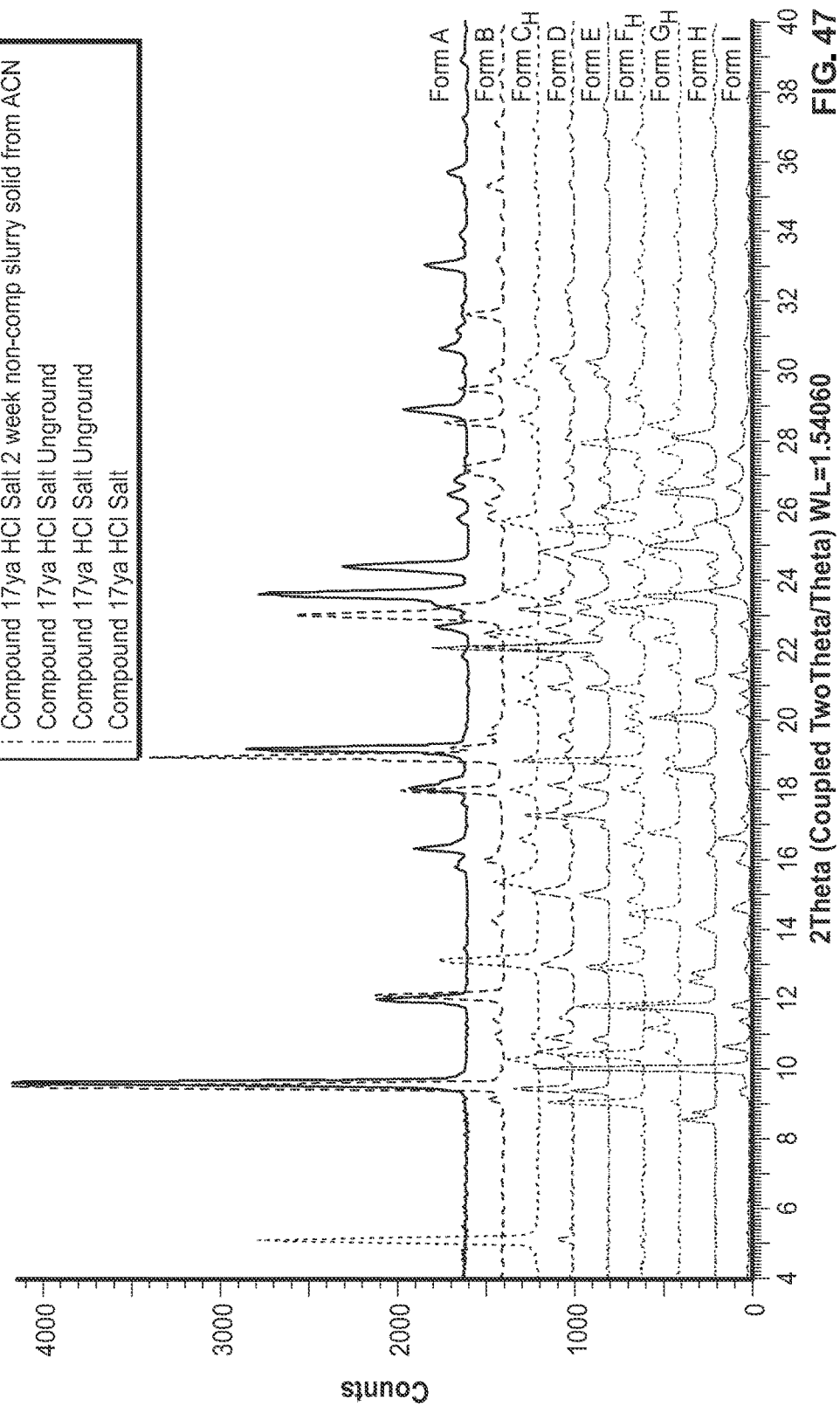
FIG. 47 illustrates the overlay of XRD diffraction patterns for Forms A, B, $C_H$, D, E, $F_H$, H and I.

Overall, Form E/E1 was initially observed in many recrystallization and slurry experiments, indicating it was the most stable form observed during these early studies. However, additional work showed that Form H was more stable than Form E and presumably Form E1 which shares many physical properties with Form E. Based on the data presented above, Form H was believed to be the thermodynamically stable form of the compound. Forms A, B, D, and I appear to be metastable polymorphic forms and Forms $C_H$, $F_H$, and $G_H$ are hydrates. A comparison of the XRD patterns of Forms A, B, $C_H$, D, E, $F_H$, $G_H$, H and I of the HCl salt of [2-(1H-indol-3-yl)-1H-imidazol-4-yl](3,4,5-trimethoxyphenyl)methanone, as were described in detailed above, is provided in FIG. 47.

Example 7: Large-Scale Synthesis of Form H of the HCl Salt of [2-(1H-Indol-3-yl)-1H-imidazol-4-yl](3,4,5-trimethoxyphenyl)methanone (API HCl) from an Intermediate C-5

The following process to make the [2-(1H-indol-3-yl)-1H-imidazol-4-yl](3,4,5-trimethoxyphenyl)methanone hydrochloride salt (API HCl) on the kilogram scale initially produced Form E or Form E1 of API HCl. The Form E and Form E1 preparations converted to Form H at ambient conditions, suggesting the relative stability of Form H.

Further, characterizations as in Examples 5 and 6, confirmed that Form H is the most stable of the polymorphic forms of API HCl. Importantly, Form H was not observed to convert to any other polymorphic form. Accordingly, the kilogram scale synthetic process below, at Step 2 and Step 17, employed seed crystals of Form H to rapidly and completely convert the crude API HCl product to pure API HCl with only Form H obtained. This product is suitable for use in pharmaceutical products.

Step 1—Pre-Processing Preparation

Prior to addition of any reagents, the reaction vessels were verified as acceptably clean, dry, and in the proper operating configuration. Prior to the first batch, the critical process instruments to be used on the reactor were verified in calibration and functioned properly. Pressurized the reaction system to at least 25-psig pressure with nitrogen. Pressure checked each part of the system and any interconnected piping with nitrogen. Included in the pressure check all lines out to the last valve. Held the system for at least 30 minutes with not more than 1 psig pressure loss. Repaired any leaks as necessary and retested. Vented the pressure to spot ventilation when complete. Pressurized the reactor again to at least 25-psig pressure with nitrogen. Pressure checked each part of the system and any interconnected piping with nitrogen. Included in the pressure check all lines out to the last valve. Held the vessel for at least 30 minutes with not more than 1 psig pressure loss. Repaired any leaks as necessary and retested. Vented the pressure to spot ventilation when complete. Vacuum checked the filter dryer to 27" Hg or less. Once at or below 27" Hg vacuum, isolated and held for at least 30 minutes. The filtration dryer passed if it did not lose 2" Hg or more over at least 30 minutes. Repaired any leaks as necessary and retested.

Step 2-[2-(1H-Indol-3-yl)-1H-imidazol-4-yl](3,4,5-trimethoxyphenyl)methanone Hydrochloride (API HCl) Reaction Step

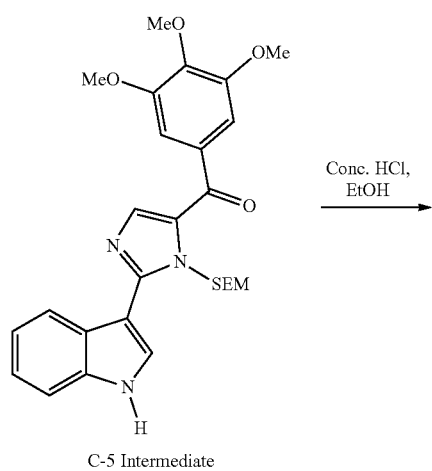

C-5 Intermediate

-continued

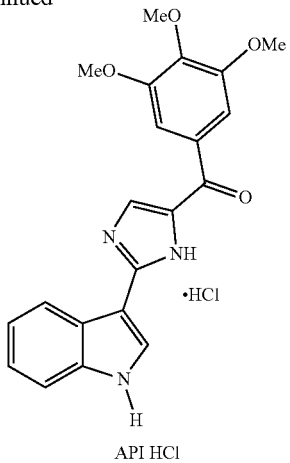

API HCl

Verified that reactor data acquisition system was turned on and that the date and time were correct. Started cooling water to the reactor's overhead condenser. Inerted the reactor with nitrogen and brought to atmospheric pressure at the end of the inerting process. Isolated the reactor from the condenser, started cooling media to the reactor jacket, and adjusted the jacket set point temperature to 22° C. Charged 1 kg of Intermediate C5 (shown above) to the reactor, taking care not to bury the agitator. Slowly inerted the reactor with nitrogen and left under vacuum at the end of the inerting process. Charged 9.152 kg of ethanol to the reactor, set the reactor agitator speed to its lowest setting, started the agitator, adjusted agitation to 100 RPM and agitated the mixture for at least 10 minutes. Then held temperature at 20-25° C. Charged 1.600 kg of conc HCl to the reactor and configured the reactor for the reaction, by confirming flow of cooling water through the reactor condenser, venting the reactor through the condenser, and starting a nitrogen sweep of reactor vent. Adjusted the reactor batch temperature to between 74° C. and 78° C. Held the reaction between 74° C. and 78° C. for 1 hour, and started cooling the batch to 20-25° C. over a period of between 1 and 2 hours. During this cooldown, once the batch was 65-70° C., collected a 1 oz sample of the reactor contents for analysis by HPLC. Charged approximately 0.010 kg (10 grams) of API HCl Form H seed crystals to the reactor and took care not to bury the agitator, then cooled the batch to 20-25° C. and held the batch at 20-25° C. for at least 12 hours. Then further cooled the batch to 0-5° C. and held the batch at 0-5° C. for at least 2 hours.

Step 3—API HCl Filtration

Prepared the filtration dryer for filtration by inerting it with nitrogen, ensuring the pressure relief drum was installed, ensuring the filter-dryer is grounded, ensuring the agitator in the filtration dryer was off and raised in the highest position. Filtered the slurry in the reactor through the filtration dryer and collected the filtrate in new drums. Initially charged the slurry slowly in small increments to allow the filter cake to establish. Near the start of the filtration, collected a sample of the filtrate and confirmed it was free of solids. Inspected the reactor for residual solids and rinsed any residual through the filtration dryer with ethanol. Charged 1.263 kg of ethyl acetate to the reactor to rinse the reactor and cooled the rinse to 0-5° C. Deliquored and smoothed out the wetcake, then drained the solvent in reactor to filtration dryer, and drained the filtration dryer to a new drum. Deliquored the wetcake.

Step 4—Crude API HCl Drying

Readied the APOVAC vacuum system by starting flow to the condensers, ensuring the ring liquid was full to overflow line, and ensuring the distillate receiver was empty. The operating parameters were the following: (1) cooling media: chilled water or glycol at 2-8° C.; (2) precondenser cooling media: chilled water or glycol at 2-8° C.; ring liquid cooler: 5 gpm (minimum); exhaust condenser: 2 gpm (minimum); charged ring liquid (if new or additional is needed): potable water. Slowly opened the vacuum block valve and pulled full vacuum (less than 27 "Hg vacuum) on filtration dryer, then started tempered water flow at 52-58° C. through the filtration dryer jacket, checking the filtration dryer every 4 hour (+/−30 minute). Continued to dry the product (jacket inlet temperature of 52-58° C., vacuum, nitrogen sweep) and after at least 12 hours of drying, the filter dryer contents were tested for volatiles by loss-on-drying using the TGA unit (105° C.). Continued to sample the dryer contents every ~8 hours until the residual volatiles content is less than or equal to 1 wt %. Once the wet cake was partially dried, started agitation on the filtration dryer to aid in the drying process and placed full cooling on filtration dryer and brought the dryer to atmospheric pressure using nitrogen. Held the dryer at 25-30° C. for at least 30 minutes before sampling for HPLC analysis. Discharged the Crude API HCl from filtration dryer into 15 L Curtec Keg. Submitted the 1 oz sample for HPLC to detect any chemical impurities, and XRPD analysis to ensure proper polymorphic form (Form H was desired). Residual solvents were also measured.

If impurities were found, additional processing steps were conducted in order to bring the batch material into target specification. E.g., acetone triturations (up to 2; Steps 5-10), ethanol:ethyl acetate trituration (Steps 11-13), or water trituration (Steps 14-16) were performed for impurities; and crystal form correction was performed (Steps 17-19) for any polymorphic crystal form other than Form H of API HCl. If no impurities and pure polymorph Form H of API HCl (per XRPD) was obtained, then no additional processing was required. I.e., optional steps 5-19 may be omitted.

Desired Targets:
Any Unknown impurity: ≤0.10%
Total impurity: ≤1.50%
ROI: ≤0.1%
Ethanol<5000 PPM
Ethyl Acetate<5000 PPM Step 5—Optional Acetone Trituration of Crude API HCl (if Impurities)

Impurities persisted, Steps 5-7 were executed and completed. Started cooling water to reactor overhead condenser, inerted the reactor with nitrogen, and brought to atmospheric pressure at the end of the inerting process. Then isolated the reactor from the condenser, started cooling media to reactor jacket, and adjusted the jacket set point temperature to 22° C. Charged all of the crude API HCl from Step 4 to the reactor, taking care not to bury the agitator, and inerted the reactor slowly with nitrogen to avoid dusting solids. Charged 11.887 kg of acetone per kg of crude API HCl added to the reactor. Set the reactor agitator speed to its lowest setting, started the agitator, adjusted agitation to 100 RPM, and agitated the mixture for at least 10 minutes. Adjusted the reactor batch temperature to between 54° C. and 58° C., and held batch temperature to between 54° C. and 58° C. for at least 12 hours. Cooled the batch to 20-24° C., and allowed the batch to mix for 15 minutes at 20-24° C.

Step 6—Triturated API Filtration

Prepared for filtration in filtration dryer by inerting dryer with nitrogen, ensuring the pressure relief drum is installed, ensuring the filter-dryer is grounded, and ensuring dryer agitator is off and raised in the highest position. Then filtered the slurry in reactor through the dryer and collected the filtrate in drums. Initially charged the slurry slowly in small increments to allow the filter cake to establish. Near the start of the filtration, collected a sample of the filtrate and confirmed it is free of solids. Inspected the reactor for solids and rinsed into dryer if present. Deliquored and smoothed out the wet cake in the dryer, then drained the solvent in the reactor to the dryer and drained dryer to new drums (labelled as Crude API HCl acetone rinse). Deliquored the wetcake.

Step 7—Triturated API Drying

Readied the APOVAC vacuum system by starting flow to the condensers, ensuring the ring liquid was full to overflow line, and ensuring the distillate receiver was empty. The operating parameters were the following: (1) cooling media: chilled water or glycol at 2-8° C.; precondenser cooling media: chilled water or glycol at 2-8° C.; ring liquid cooler: 5 gpm (minimum); exhaust condenser: 2 gpm (minimum); ring liquid (if new or additional is needed): potable water. Slowly opened the vacuum block valve and pulled full vacuum (less than 27 "Hg vacuum) on the dryer and started flow of tempered water at 47-53° C. through the dryer jacket. Checking progress of the dryer at 4 hour (+/−30 minutes) intervals. Continued to dry the product (jacket inlet temperature of 47-53° C., vacuum, nitrogen sweep), and after at least 12 hours of drying, sampled the filter dryer contents and tested the sample for volatiles by loss-on-drying using the TGA unit (105° C.). Continued to sample the dryer contents every ≥8 hours until the residual volatiles content was less than or equal to 1 wt %. Once the wet cake was partially dried, started agitation on the dryer to aid in the drying process. When the drying in-process control met the necessary requirements, placed full cooling on dryer and brought the dryer to atmospheric pressure using nitrogen, and held the dryer at 25-30° C. for at least 30 minutes before sampling. Collected a 1 oz sample from the dryer of the API HCl for HPLC analysis for purity testing, proper polymorphic form testing via XRPD, and residual solvents. Discharged the Crude API HCl from the dryer into 15 L Curtec Keg. In view results vs target ranges specified at the end of Step 4, additional processing in this batch record was sometimes necessary. If all results were within purity specifications and only polymorphic Form H of API HCl was obtained (per XRPD), then no additional processing was required. Otherwise, impurities can be eliminated by an optional second acetone trituration (Steps 8-10), an optional ethanol/ethyl acetate trituration (Steps 11-13), or an optional deionized water trituration (Steps 14-16) to remove impurities, or an optional API HCl form correction (Steps 17-19) to obtain Form H.

Step 8—Optional Second Acetone Trituration (if Impurities)

If impurities persisted, Steps 8-10 were executed and completed. As before, the reactor and the filtration dryer were cleaned, started cooling water to reactor overhead condenser, inerted the reactor with nitrogen, and brought reactor to atmospheric pressure at the end of the inerting process. Isolated the reactor from the condenser, started cooling media to reactor jacket, and adjusted the jacket set point temperature to 22° C. Charged all of the crude API HCl from Step 7 or any other drying step to the reactor, taking care not to bury the agitator. Slowly inerted the reactor with nitrogen to avoid dusting solids. Charged 11.887 kg of acetone per kg of crude API HCl to the reactor, set the reactor agitator speed to its lowest setting, started the agitator, adjusted agitation to 100 RPM, and agitated the mixture for at least 10 minutes. Then adjusted the reactor batch temperature to between 54° C. and 58° C. and held this temperature for at least 12 hours. Cooled the batch to 20-24° C. and allowed the batch to mix for 15 minutes at 20-24° C.

Step 9—Triturated API Filtration

Prepared for filtration in filtration dryer by inerting the dryer with nitrogen; ensuring the pressure relief drum was installed; ensuring the filter-dryer was grounded; ensuring dryer agitator was off and raised in the highest position. Filtered the slurry in the reactor through dryer and collected the filtrate in new drums. Initially charged the slurry slowly in small increments to allow the filter cake to establish. Near the start of the filtration, collected a sample of the filtrate and confirmed it is free of solids. If solids persisted in the filtrate, then refilter. Inspected the reactor for solids, and if significant solids remained, recycled filtrate and charged more acetone rinse to remove. Deliquored and smoothed out the wet cake in the filtration dryer. Drained the solvent in reactor to dryer, then drained dryer to new drums. Deliquored the wetcake.

Step 10—Triturated API Drying

Readied the APOVAC vacuum system by starting flow to the condensers; ensuring the ring liquid was full to overflow line; and ensuring the distillate receiver was empty. The operating parameters were the following: cooling media: chilled water or glycol at 2-8° C.; precondenser cooling media: chilled water or glycol at 2-8° C.; ring liquid cooler: 5 gpm (minimum); exhaust condenser: 2 gpm (minimum); and ring liquid (if new or additional is needed): potable water. Slowly opened the vacuum block valve and pulled full vacuum (less than 27 "Hg vacuum) on the dryer, started tempered water flow at 47-53° C. through the dryer jacket, began monitoring dryer every 4 hour (+/−30 minutes). Continued to dry the product (jacket inlet temperature of 47-53° C., vacuum, nitrogen sweep), and after at least 12 hours of drying, the contents of the filter dryer were sampled and tested for volatiles by loss-on-drying using the TGA unit (105° C.). Continued to sample the dryer contents every ≥8 hours until the residual volatiles content was less than or equal to 1 wt %. Once the wet cake was partially dried, started agitation on the dryer to aid in the drying process. When the drying in-process control met the necessary requirements, placed full cooling on the dryer, brought the dryer to atmospheric pressure using nitrogen, and held the dryer at 25-30° C. for at least 30 minutes before sampling. Collected a 1 oz sample from the dryer of the API HCl for HPLC analysis. Discharged the API HCl from dryer into 15 L Curtec Kegs. Submitted the 1 oz sample for HPLC purity testing, XRPD testing for desired polymorphic Form H, and residual solvents. If all results were within specifications and polymorphic Form H of API HCl was obtained (per XRPD), then no additional processing was required. Otherwise, impurities can be eliminated by an optional ethanol/ethyl acetate trituration (Steps 11-13) and/or an optional deionized water trituration (Steps 14-16) to remove impurities, or an optional API HCl form correction (Steps 17-19) to make Form H.

Step 11—Optional Ethanol/Ethyl Acetate Trituration (if Impurities)

If impurities persisted, Steps 11-13 were executed and completed. As before, the reactor and the filtration dryer were cleaned, started cooling water to reactor overhead condenser, inerted the reactor with nitrogen, and brought reactor to atmospheric pressure at the end of the inerting process. Isolated the reactor from the condenser, started cooling media to reactor jacket, and adjusted the jacket set point temperature to 22° C. Charged all of the crude API HCl from Step 10 or any other drying step to the reactor, taking care not to bury the agitator. Slowly inerted the reactor with nitrogen to avoid dusting solids. Charged 4.500 kg of ethyl acetate per kg of crude API HCl to the reactor, set the reactor agitator speed to its lowest setting, started the agitator, adjusted agitation to 100 RPM, and agitated the mixture for at least 10 minutes. Adjusted the reactor batch temperature to between 58° C. and 62° C. and held batch temperature to between 58° C. and 62° C. for at least 24 hours. Cooled the batch to 20-25° C. and allowed the batch to mix for 15 minutes at 20-24° C.

Step 12—Triturated API Filtration

Prepared for filtration in filtration dryer by inerting the dryer with nitrogen; ensuring the pressure relief drum was installed; ensuring the filter-dryer was grounded; ensuring dryer agitator was off and raised in the highest position. Filtered the slurry in the reactor through the dryer and collected the filtrate in new drums. Initially charged the slurry slowly in small increments to allow the filter cake to establish. Near the start of the filtration, collected a sample of the filtrate and confirmed it is free of solids. If solids persisted in the filtrate, then refiltered. Inspected the reactor for solids, and if significant solids remained, recycled filtrate. Then rinsed by adding to the reactor 0.900 kg of ethyl acetate per kg of crude API HCl and 0.790 kg of ethanol per kg of crude API HCl. Then set reactor agitator speed to its lowest setting, started the agitator, and adjusted agitation to 100 RPM. Adjusted the reactor contents to between 2° C. and 8° C. Deliquored and smoothed out the wet cake in the dryer, drained the solvent in reactor to the dryer, and then drained the dryer to new drums. Again, the wetcake was deliquored.

Step 13—Triturated API Drying

Readied the APOVAC vacuum system by starting flow to the condensers; ensuring the ring liquid was full to overflow line; and ensuring the distillate receiver was empty. The operating parameters are the following: cooling media: chilled water or glycol at 2-8° C.; precondenser cooling media: chilled water or glycol at 2-8° C.; ring liquid cooler: 5 gpm (minimum); exhaust condenser: 2 gpm (minimum); and ring liquid (if new or additional is needed): potable water. Slowly opened the vacuum block valve and pulled full vacuum (less than 27 "Hg vacuum) on the dryer, started tempered water flow at 52-58° C. through the dryer jacket, and began monitoring drying every 4 hours (+/−30 minutes). Continued to dry the product (jacket inlet temperature of 52-58° C., vacuum, nitrogen sweep), and after at least 12 hours of drying, the contents of the filter dryer were sampled and tested for volatiles by loss-on-drying using the TGA unit (105° C.). Continued to sample the dryer contents every ≥8 hours until the residual volatiles content was less than or equal to 1 wt %. Once the wet cake was partially dried, started agitation on the dryer to aid in the drying process. When the drying in-process control met the necessary requirements, placed full cooling on the dryer and brought the dryer to atmospheric pressure using nitrogen, and held the dryer at 25-30° C. for at least 30 minutes before sampling. Collected a 1 oz sample from the dryer of the API HCl for HPLC testing, XRPD testing and residual solvents testing. Discharged the API HCl from the dryer into 15 L Curtec Kegs. If all results were within specifications and only polymorphic Form H of API HCl was obtained (per XRPD), then no additional processing was required. Otherwise, impurities can be eliminated by an optional deionized water trituration (Steps 14-16), or Form H can be made by an optional API HCl form correction (Steps 17-19).

Step 14—Optional DI Water Trituration (if Impurities)

If impurities persisted, Steps 14-16 were executed and completed. As before, the reactor and the filtration dryer were cleaned, started cooling water to reactor overhead condenser, inerted the reactor with nitrogen, and brought reactor to atmospheric pressure at the end of the inerting process. Isolated the reactor from the condenser, started cooling media to reactor jacket, and adjusted the jacket set point temperature to 22° C. Charged all of the crude API HCl from Step 13 or any other drying step to the reactor, taking care not to bury the agitator. Slowly inerted the reactor with nitrogen to avoid dusting solids. Charged 10 kg of WFI (water for injection) quality water per kg of crude API HCl charged to the reactor, set the reactor agitator speed to its lowest setting, started the agitator, adjusted agitation to 100 RPM, and agitated the mixture for at least 10 minutes. Adjusted the reactor batch temperature to between 58° C. and 62° C. and held batch temperature to between 58° C. and 62° C. for at least 4 hours. Cooled the batch to 20-24° C. over the course of at least one hour.

Step 15—Triturated API Filtration

Prepared for filtration in filtration dryer by inerting the dryer with nitrogen; ensuring the pressure relief drum was installed; ensuring the filter-dryer was grounded; ensuring dryer agitator was off and raised in the highest position. Filtered the slurry in the reactor through dryer and collected the filtrate in new drums. Initially charged the slurry slowly in small increments to allow the filter cake to establish. Near the start of the filtration, collected a sample of the filtrate and confirmed it is free of solids. If solids persisted in the filtrate, then refiltered. Inspected the reactor for solids, and if significant solids remained, recycled filtrate. Then rinsed by adding to the reactor 10 kg of WFI quality water per kg of crude API HCl. Drained the solvent in reactor to the dryer, and then drained the dryer to new drums. The wetcake was deliquored.

Step 16—Triturated API Drying

Readied the APOVAC vacuum system by starting flow to the condensers; ensuring the ring liquid was full to overflow line; and ensuring the distillate receiver was empty. The operating parameters were the following: cooling media: chilled water or glycol at 2-8° C.; precondenser cooling media: chilled water or glycol at 2-8° C.; ring liquid cooler: 5 gpm (minimum); exhaust condenser: 2 gpm (minimum); and ring liquid (if new or additional is needed): potable water. Slowly opened the vacuum block valve and pulled full vacuum (less than 27 "Hg vacuum) on the dryer, started tempered water flow at 50-60° C. through the dryer jacket, and began monitoring drying every 4 hour (+/−30 minutes). Continued to dry the product (jacket inlet temperature of 50-60° C., vacuum, nitrogen sweep), and after at least 12 hours of drying, the contents of the filter dryer were sampled and tested for volatiles by loss-on-drying using the TGA unit (105° C.). Continued to sample the dryer contents every ≥8 hours until the residual volatiles content was less than or equal to 1 wt %. Once the wet cake was partially dried, started agitation on the dryer to aid in the drying process. When the drying in-process control met the necessary requirements, placed full cooling on the dryer, brought the dryer to atmospheric pressure using nitrogen, and held the dryer at 25-30° C. for at least 30 minutes before sampling. Collected a 1 oz sample from the dryer of the API HCl for HPLC testing, XRPD testing and residual solvents testing. Discharged the API HCl from the dryer into 15 L Curtec Kegs. If all results were within specifications and only polymorphic Form H of API HCl was obtained (per XRPD), then no additional processing was required. If Form H was not obtained, an optional API HCl form correction (Steps 17-19) was performed.

Step 17—API HCl Form Correction

If Form H was not observed in Step 16 or any of the dryer steps above, then Steps 17-19 were performed. Inerted the reactor with nitrogen and brought to atmospheric pressure at the end of the inerting process. Isolated the reactor from the condenser, started cooling media to reactor jacket, and adjusted the jacket set point temperature to 22° C. Charged all of the Crude API HCl from Step 16 or any previously executed trituration to the reactor, taking care not to bury the agitator. Slowly inerted the reactor with nitrogen to avoid dusting solids. Charged 3.945 kg of ethanol per kg of crude API HCl and 4.510 kg of ethyl acetate per kg of crude API HCl to the reactor, set the reactor agitator speed to its lowest setting, started the agitator, adjusted agitation to 100 RPM, and agitated the mixture for at least 10 minutes at 20-25° C. Charged 0.010 kg of Form H seed crystals of API HCl to the reactor, taking care not to bury the agitator. Closed the charge valve on the reactor once the charge was completed and configured the reactor by confirming flow of cooling water through the reactor condenser; venting the reactor through the condenser; and starting a nitrogen sweep of the reactor vent. Adjusted the reactor batch temperature to between 58° C. and 62° C. and began monitoring about every 2 hours (+/−30 minutes) until the form conversion was complete. Held the reaction at between 58° C. and 62° C. for at least 24 hours. Collected a 1 oz sample of the reactor contents by: (1) placed 5 psig nitrogen pressure on the reactor; (2) collected a 1 oz sample to flush the sample line; (3) collected a 1 oz sample of the reactor contents; and (4) vented the reactor to spot exhaust with a slow nitrogen purge on the vent. Analyzed the reactor contents sample (second sample) by XRPD to confirm the proper polymorph, Form H, was obtained. If Form H was not formed within the first 24 hours, then the reaction can be held at 58° C. and 62° C. and sampled for up to 2 additional 24 hour iterations until Form H forms. Once Form H is formed, cooled the batch to 20-25° C. and held for at least 20 minutes.

Step 18—Form H of API HCl Filtration

Prepared for filtration in filtration dryer by inerting the dryer with nitrogen; ensuring the pressure relief drum was installed; ensuring the filter was grounded; and ensuring the dryer agitator was off and raised in the highest position. Filtered the slurry in reactor through the dryer and collected the filtrate in new drums. Initially charged the slurry slowly in small increments to allow the filter cake to establish. Near the start of the filtration, collected a sample of the filtrate and confirmed it is free of solids. If solids persisted in the filtrate, then refiltered. Inspected the reactor for solids, and if significant solids remained, recycled filtrate. Then rinsed the reactor by adding to the reactor 0.789 kg of ethanol per kg of crude API HCl and 0.902 kg of ethyl acetate per kg of crude API HCl added to the reactor. Cooled the rinse to 2-8° C. Deliquored and smoothed out the wetcake. Drained the solvent in the reactor to the dryer, and then drained the dryer to new drums. The wetcake was again deliquored.

Step 19—API HCl Form H Drying

Readied the APOVAC vacuum system by starting flow to the condensers; ensuring the ring liquid was full to overflow line; and ensuring the distillate receiver was empty. The operating parameters were the following: cooling media: chilled water or glycol at 2-8° C.; precondenser cooling media: chilled water or glycol at 2-8° C.; ring liquid cooler: 5 gpm (minimum); exhaust condenser: 2 gpm (minimum); and ring liquid (if new or additional is needed): potable water. Slowly opened the vacuum block valve and pulled full vacuum (less than 27 "Hg vacuum) on the dryer, started tempered water flow at 52-58° C. through the dryer jacket, and began monitoring drying every 4 hour (+/−30 minutes). Continued to dry the product (jacket inlet temperature of 52-58° C., vacuum, nitrogen sweep), and after at least 12 hours of drying, the contents of the filter dryer were sampled and tested for volatiles by loss-on-drying using the TGA unit (105° C.). Continued to sample the dryer contents every ≥8 hours until the residual volatiles content was less than or equal to 1 wt %. Once the wet cake was partially dried, started agitation in the dryer to aid in the drying process. When the drying in-process control met the necessary requirements, placed full cooling on the dryer and brought the dryer to atmospheric pressure using nitrogen. Collected a 2 oz sample from the dryer of the API HCl for analysis by HPLC, Karl Fisher, appearance, XRPD and residual solvents testing. If GC results for residual solvents were higher than target, dried material for an additional time and re-tested. Discharged the API HCl from the dryer into 15 L Curtec Kegs. If all results were within specifications and only polymorphic Form H of API HCl was obtained (per XRPD), then no additional processing was required.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A crystalline polymorph Form H of the [2-(1H-indol-3-yl)-1H-imidazol-4-yl](3,4,5-trimethoxyphenyl) methanone hydrochloride salt characterized by an X-ray powder diffraction (XRD) pattern having peaks at 11.8, 20.1, 23.6, 25.0, and 26.5 2θ±0.2 2θ.

2. The crystalline polymorph Form H of the [2-(1H-indol-3-yl)-1H-imidazol-4-yl](3,4,5-trimethoxyphenyl) methanone hydrochloride salt according to claim 1 further characterized by XRD peaks at 8.6, 12.5, 18.6, 21.2, and 28.1 2θ±0.2 2θ.

3. The crystalline polymorph Form H of the [2-(1H-indol-3-yl)-1H-imidazol-4-yl](3,4,5-trimethoxyphenyl) methanone hydrochloride salt according to claim 1 further characterized by an XRD pattern as depicted in FIG. 43.

4. The crystalline polymorph Form H of the [2-(1H-indol-3-yl)-1H-imidazol-4-yl](3,4,5-trimethoxyphenyl) methanone hydrochloride salt according to claim 1 having a thermogravimetric analysis (TGA) thermogram with an average value of 0.03% weight loss at 150° C.

5. The crystalline polymorph Form H of the [2-(1H-indol-3-yl)-1H-imidazol-4-yl](3,4,5-trimethoxyphenyl) methanone hydrochloride salt according to claim 1 having a differential scanning calorimetry (DSC) thermogram with a melting endotherm with an onset of 247.5° C. with a peak maximum of 250.1° C.

6. A process to make Form H of the [2-(1H-indol-3-yl)-1H-imidazol-4-yl](3,4,5-trimethoxyphenyl) methanone hydrochloride salt by incubation of Form E or Form E1 at ambient temperatures.

7. A process to make Form H of the [2-(1H-indol-3-yl)-1H-imidazol-4-yl](3,4,5-trimethoxyphenyl) methanone hydrochloride salt by competitive slurry of Form E and Form H in 2-butanol or 2-propanol for 1 day, wherein to avoid possible desolvation or physical change after isolation, the samples were not further dried before X-ray analysis of the resulting Form H,
wherein Form E is characterized by an X-ray powder diffraction (XRD) pattern having peaks at 9.4, 17.3, 22.1, 23.4, and 24.8 2θ±0.2 2θ, or as further characterized by an XRD pattern as depicted in FIG. 29; and
wherein Form H is characterized by an X-ray powder diffraction (XRD) pattern having peaks at 11.8, 20.1, 23.6, 25.0, and 26.5 2θ±0.2 2θ, or further characterized by an XRD pattern as depicted in FIG. 43.

8. The process of claim 7, whereby said Form H is synthesized by co-incubation of Form E and Form H in 2-butanol for 1 day, wherein said co-incubation involves adding said Form E and said Form H to neat 2-butanol until saturated, agitating the resulting suspension for 1 day at ambient temperature, and vacuum filtering the solids to produce Form H.

9. The process of claim 7, whereby said Form H is synthesized by co-incubation of Form E and Form H in 2-propanol for 1 day, wherein said co-incubation involves adding said Form E and said Form H to neat 2-propanol until saturated, agitating the resulting suspension for 1 day at ambient temperature, and vacuum filtering the solids to produce Form H.

10. A process to make Form H of the [2-(1H-indol-3-yl)-1H-imidazol-4-yl](3,4,5-trimethoxyphenyl) methanone hydrochloride salt by seeding of Form H crystals into the synthesis of other polymorphic forms of said salt.

11. The process of claim 10, whereby said other polymorphic forms is said Form E, wherein Form E is characterized by an XRD pattern having peaks at 9.4, 17.3, 22.1, 23.4, and 24.8 2θ±0.2 2θ, or as further characterized by an XRD pattern as depicted in FIG. 29.

12. The process of claim 10, whereby said other polymorphic forms is said Form E1, wherein Form E1 is characterized by an XRD pattern having peaks at 9.4, 10.9, 17.3, 22.1, and 23.2 2θ±0.2 2θ, or as further characterized by an XRD pattern as depicted in FIG. 30.

* * * * *